United States Patent
Kehe et al.

(10) Patent No.: US 12,115,197 B2
(45) Date of Patent: Oct. 15, 2024

(54) MICROBIAL COMPOSITIONS FOR THE TREATMENT OF SKIN DISEASES

(71) Applicant: Concerto Biosciences, Inc., Cambridge, MA (US)

(72) Inventors: Jared Kehe, Cambridge, MA (US); Bernardo Cervantes, Cambridge, MA (US); Cheri Ackerman, Somerville, MA (US); Abdulrahman Hassaballah, Boston, MA (US); Keaton Armentrout, Seattle, WA (US)

(73) Assignee: Concerto Biosciences, Inc., Cambridge, MA (US)

( * ) Notice: Subject to any disclaimer, the term of this patent is extended or adjusted under 35 U.S.C. 154(b) by 0 days.

(21) Appl. No.: 18/589,539

(22) Filed: Feb. 28, 2024

(65) Prior Publication Data
US 2024/0189369 A1    Jun. 13, 2024

Related U.S. Application Data

(63) Continuation of application No. PCT/US2022/079637, filed on Nov. 10, 2022.

(60) Provisional application No. 63/278,134, filed on Nov. 11, 2021.

(51) Int. Cl.
| | |
|---|---|
| *A61K 35/741* | (2015.01) |
| *A61K 31/51* | (2006.01) |
| *A61P 31/04* | (2006.01) |
| *C12N 1/20* | (2006.01) |
| *C12R 1/07* | (2006.01) |

(52) U.S. Cl.
CPC ............ *A61K 35/741* (2013.01); *A61K 31/51* (2013.01); *A61P 31/04* (2018.01); *C12N 1/20* (2013.01); *C12R 2001/07* (2021.05)

(58) Field of Classification Search
None
See application file for complete search history.

(56) References Cited

U.S. PATENT DOCUMENTS

| | | |
|---|---|---|
| 8,383,097 B2 | 2/2013 | Frodyma |
| 11,760,969 B2 | 9/2023 | Farmer |
| 2014/0328803 A1 | 11/2014 | McKenzie |
| 2020/0246397 A1 | 8/2020 | Nakatsuji |
| 2022/0088091 A1 | 3/2022 | Ochrombel |
| 2022/0096574 A1 | 3/2022 | Skolnick |
| 2022/0168363 A1 | 6/2022 | Stannek-Göbel |
| 2022/0211036 A1 | 7/2022 | Hänsel |
| 2022/0211046 A1 | 7/2022 | Malang |
| 2022/0280579 A1 | 9/2022 | Cutting |
| 2022/0304920 A1 | 9/2022 | Farmer |
| 2023/0151324 A1 | 5/2023 | Waugh |
| 2023/0292764 A1 | 9/2023 | Jorge |
| 2023/0390346 A1 | 12/2023 | Gangaiah |
| 2024/0009254 A1 | 1/2024 | Lee |
| 2024/0050491 A1 | 2/2024 | Shemesh |

FOREIGN PATENT DOCUMENTS

| | | |
|---|---|---|
| EP | 4255580 A1 | 10/2023 |
| WO | 2014178032 A1 | 11/2014 |
| WO | 2020214843 A1 | 10/2020 |
| WO | 2022226376 A2 | 10/2022 |

OTHER PUBLICATIONS

Genbank Accession No. MG020358. Bacillus amyloliquefaciens strain BBC023 16S ribosomal RNA gene, partial sequence, Sep. 2, 2018; retrieved from internet: <URL: https://www.ncbi.nlm.nih.gov/nuccore/MG020358>, 2 pages.
Genbank Accession No. CP053289. Bacillus cereus strain WPySW2 chromosone, complete genome, May 18, 2020, retrieved from internet: <URL: http://www.ncbi.nlm.nih.gov/nuccore/CP053289>, 3 pages.
International Search Report mailed Apr. 6, 2023 for International Application No. PCT/US2022/079637.
Kizhakkekalam, V.K., et al., Antibacterial and wound healing potential of topical formulation of marine symbiotic Bacillus. Arch Microbiol. Sep. 27, 2022;204(10):648. doi: 10.1007/s00203-022-03246-5.
Piewngam, P. et al., "Probiotic for pathogen-specific *Staphylococcus aureus* decolonisation in Thailand: a phase 2, double-blind, randomised, placebo-controlled trial", The Lancet Microbe, vol. 4, Issue 2, E75-E83, Feb. 2023, doi: https://doi.org/10.1016/S2666-5247(22)00322-6.
Concerto Biosciences, Topical ENS-002 for Atopic Dermatitis in Adults (EnSync); ClinicalTrials.gov ID: NCT06469385 [online]. U.S. National Institute of Health. National Library of Medicine; National Center for Biotechnology Information Jun. 26, 2024 [retrieved on Jul. 10, 2024]. Retrieved from the internet.

*Primary Examiner* — Oluwatosin A Ogunbiyi
(74) *Attorney, Agent, or Firm* — Greenberg Traurig, LLP

(57) ABSTRACT

Provided herein are compositions, methods, kits, and devices for the treatment of skin diseases. Also provided herein are isolated and purified bacteria, excipients, carriers, dosage forms and routes of administration for such bacteria. Furthermore, provided herein are isolated and purified mixtures of bacteria, excipients, carriers, dosage forms and routes of administration for such mixtures. Also provided herein are conditions for treatment with bacteria and bacterial mixtures.

27 Claims, 24 Drawing Sheets
Specification includes a Sequence Listing.

Inhibition of agr and psmA (2 functions)  3.8%

Inhibition of agr and psmA and sigB (3 functions)  1.1%

S. aureus 10-fold dilution series | CFU/mL

TSB + PBS (control)  1.7E10 ± 8E9

TSB + 5% N sup  1.9E10 ± 1.2E10

TSB + 10% N sup  0.0 ± 0.0

SEQUENCE LISTING

```
Sequence total quantity: 21
SEQ ID NO: 1              moltype = DNA   length = 1196
FEATURE                   Location/Qualifiers
source                    1..1196
                          mol_type = other DNA
                          organism = synthetic construct
SEQUENCE: 1
tcttatgaag ttagcggcgg acgggtgagt aacacgtggg taacctgccc ataagactgg   60
gataactccg ggaaaccggg gctaataccg gataacattt tgaaccgcat ggttcgaaat   120
tgaaaggcgg cttcggctgt cacttatgga tggacccgcg tcgcattagc tagttggtga   180
ggtaacggct caccaaggca acgatgcgta gccgacctga gagggtgatc ggccacactg   240
ggactgagac acggcccaga ctcctacggg aggcagcagt agggaatctt ccgcaatgga   300
cgaaagtctg acggagcaac gccgcgtgag tgatgaaggc tttcgggtcg taaaactctg   360
ttgttaggga agaacaagtg ctagttgaat aagctggcac cttgacggta cctaaccaga   420
aagccacggc taactacgtg ccagcagccg cggtaatacg taggtggcaa gcgttatccg   480
```

```
gaattattgg gcgtaaagcg cgcgcaggtg gtttcttaag tctgatgtga agcccacgg    540
ctcaaccgtg gagggtcatt ggaaactggg agacttgagt gcagaagagg aaagtggaat   600
tccatgtgta gcggtgaaat gcgtagagat atggaggaac accagtggcg aaggcgactt   660
tctggtctgt aactgacact gaggcgcgaa agcgtgggga gcaaacagga ttagataccc   720
tggtagtcca cgccgtaaac gatgagtgct aagtgttaga ggtttccgcc ctttagtgc    780
tgaagttaac gcattaagca ctccgcctgg ggagtacggc cgcaaggctg aaactcaaag   840
gaattgacgg gggcccgcac aagcggtgga gcatgtggtt taattcgaag caacgcgaag   900
aaccttacca ggtcttgaca tcctctgaaa accctagaga tagggcttct ccttcggag    960
cagagtgaca ggtggtgcat ggttgtcgtc agctcgtgtc gtgagatgtt gggttaagtc  1020
ccgcaacgag cgcaacccct gatcttagtt gccatcatta gttgggcac tctaaggtga   1080
ctgccggtga caaccggag gaaggtgggg atgacgtcaa atcatcatgc ccctatgac    1140
ctgggctaca cacgtgctac aatggacggt acaaagagct gcaagaccgc gaggtg       1196

SEQ ID NO: 2              moltype = DNA   length = 1134
FEATURE                   Location/Qualifiers
source                    1..1134
                          mol_type = other DNA
                          organism = synthetic construct
SEQUENCE: 2
cgagcgaaca gaaaaggaag ntgctccttt gacgttagcg gcggacgggt gagtaacacg    60
tgggcaacct acccctanta gtttgggata actccgggaa nccggggcta ataccgaata   120
atctctttg cttcatggtn aaagactgaa agacggtttc ggctgtcgct ataggatggg    180
cccgcggcgc attagctagt tggtgaggta acggctcacc aaggcgacga tgcgtagccg   240
acctgagagg gtgatcggcc acactgggac tgagacaccg cccagactc ctacgggagg    300
cagcagtagg gaatcttcca caatgggcga aagcctgatg agcaacgcc gcgtgagtga    360
agaaggtttt cggatcgtaa aactctgttg taagggaaga acaagtacag tagtaactgg   420
ctgtaccttg acggtacctt attagaaagc cacggctaac tacgtgccag cagccgcggt   480
aatacgtagg tggcaagcgt tgtccggaat tattgggcgt aaagcgcgcg caggcggtcc   540
tttaagtctg atgtgaaagc ccacggctca accgtggagg gtcattggaa actggggac    600
ttgagtgcag aagaggaaag tggaattcca agtgtagcgg tgaaatgcgt agagatttgg   660
aggaacacca gtggcgaagg cgactttctg gtctgtaact gacgctgagg cgcgaaagcg   720
tggggagcaa acaggattag ataccctggt agtccacgcc gtaaacgatg agtgctaagt   780
gttagggggt ttccgcccct tagtgctgca gctaacgcat taagcactcc gcctggggag   840
tacggtcgca agactgaaac tcaaaggaat tgacggggg ccgcacaag ggtggagcat    900
gtggtttaat tcgaagcaac gcgaagaacc ttaccaggtc ttgacatccc gttgaccact   960
gtagagatat agtttcccct tcgggggcaa cggtgacagg tggnggcatg gttgtcgtca  1020
gctcgtgtcg tgagatgntg gggttaagtc ccgcaacgag cgcaacccct gatcttagtt  1080
gccatcattt agttgggcac tctaaggtga ctgccggtga caaccggag gagg          1134

SEQ ID NO: 3              moltype = DNA   length = 1230
FEATURE                   Location/Qualifiers
source                    1..1230
                          mol_type = other DNA
                          organism = synthetic construct
SEQUENCE: 3
aatacatgca agtcgagcga atggattaag agcttgctct tatgaagtta gcggcggacg    60
ggtgagtaac acgtgggtaa cctgcccata agactgggat aactccggga aaccggggct   120
aataccggat aacatttga accgcatggt tcgaaattga aaggcggctt cggctgtcac    180
ttatggatgg acccgcgtcg cattagctag ttggtgaggt aacggctcac caaggcaacg   240
atgcgtagcc gacctgagag ggtgatcggc cacactggga ctgagacacg gcccagactc   300
ctacgggagg cagcagtagg gaatcttccg caatgggacga aagtctgacg gagcaacgcc   360
gcgtgagtga tgaaggcttt cgggtcgtaa aactctgttg ttagggaaga acaagtgcta   420
gttgaataag ctggcaccttt gacggtacct aaccagaaag ccacggctaa ctacgtgcca   480
gcagccgcgg taatacgtag gtggcaagcg ttatccggaa ttattgggcg taaagcgcgc   540
gcaggtggtt tcttaagtct gatgtgaaag cccacgggctc aaccgtggga ggtcattgga   600
aactgggaga cttgagtgca gaagaggaaa gtggaattcc atgtgtagcg gtgaaatgcg   660
tagagatatg gaggaacacc agtggcgaag gcgactttct ggtctgtaac tgacactgag   720
gcgcgaaagc gtggggagca aacaggatta gataccctgg tagtccacgc cgtaaacgat   780
gagtgctaag tgttagaggg tttccgccct tagtgctgca agttaacgca ttaagcactc   840
cgcctgggga gtacggccgc aaggctgaaa ctcaaaggaa ttgacggggg cccgcacaag   900
cggtggagca tgtggtttaa ttcgaagcaa cgcgaagaac cttaccaggt cttgacatcc   960
tctgacaacc ctagagatag gcttctcct cgggagcag agtgacaggt ggtgcatggt  1020
tgtcgtcagc tcgtgtcgtg agatgttggg ttaagtcccg caacgagcgc aacccttgat  1080
cttagttgcc atcattaagt tgggcactct aaggtgactg ccggtgacaa accggaggaa  1140
ggtggggatg acgtcaaatc atcatgcccc ttatgacctg ggctacacac gtgctacaat  1200
ggacggtaca aagagctgca agaccgcgag                                   1230

SEQ ID NO: 4              moltype = DNA   length = 1197
FEATURE                   Location/Qualifiers
source                    1..1197
                          mol_type = other DNA
                          organism = synthetic construct
SEQUENCE: 4
ggatggttgt ttgaaccgca tggttcagac ataaaaggtg gcttcggcta ccacttacag    60
atggaccccgc ggcgcattag ctagttggtg aggtaacggc tcaccaaggc aacgatgcgt   120
agccgacctg agagggtgat cggccacact gggactgaga cacggcccag actcctacg    180
gaggcagcag tagggaatct tccgcaatgg acgaaagtct gacggagcaa cgccgcgtga   240
gtgatgaagg ttttcggatc gtaaagctct gttgttaggg aagaacaagt gccgttcaaa   300
tagggcggca ccttgacggt acctaaccag aaagccacgc taactacgt gccagcagcc    360
```

```
gcggtaatac gtaggtggca agcgttgtcc ggaattattg ggcgtaaagg gctcgcaggc    420
ggtttcttaa gtctgatgtg aaagcccccg gctcaaccgg ggagggtcat tggaaactgg    480
ggaacttgag tgcagaagag gagagtggaa ttccacgtgt agcggtgaaa tgcgtagaga    540
tgtggaggaa caccagtggc gaaggcgact ctctggtctg taactgacgc tgaggagcga    600
aagcggtgggg agcgaacagg attagatacc ctggtagtcc acgccgtaaa cgatgagtgc    660
taagtgttag ggggtttccg ccccttagtg ctgcagctaa cgcattaagc actccgcctg    720
gggagtacgg tcgcaagact gaaactcaaa ggaattgacg gggcccgca caagcggtgg    780
agcatgtggt ttaattcgaa gcaacgcgaa gaaccttacc aggtcttgac atcctctgac    840
aatcctagag ataggacgtc cccttcgggg gcagagtgac aggtggtgca tggttgtcgt    900
cagctcgtgt cgtgagatgt tgggttaagt cccgcaacg agcgcaaccc ttgatcttag    960
ttgccagcat tcagttgggc actctaaggt gactgccggt gacaaaccgg aggaagggtg   1020
ggggatgacg tcaaatcatc atgcccctta tgacctgggc tacacacgtg ctacaatgga   1080
cagaacaaag ggcagcgaaa ccgcgaggtt aagccaatcc cacaaatctg ttctcagttc   1140
ggatcgcagt ctgcaactcg actgcgtgaa gctggaatcg ctagtaatcg cggatca     1197

SEQ ID NO: 5             moltype = DNA   length = 1253
FEATURE                  Location/Qualifiers
source                   1..1253
                         mol_type = other DNA
                         organism = synthetic construct
SEQUENCE: 5
cgtgggtaac ctgcctgtaa gactgggata actccgggaa accggggcta ataccggatg     60
gttgtttgaa ccgcatggtt cagacataaa aggtggcttc ggctaccact tacagatgga    120
cccgcggcgc attagctagt tggtgaggta acggctcacc aagcaacga tgcgtagccg    180
acctgagagg gtgatcggcc acactgggac tgagacacgg cccagactcc tacgggaggc    240
agcagtaggg aatcttccgc aatggacgaa agtctgacgg agcaacgccg cgtgagtgat    300
gaaggttttc ggatcgtaaa gctctgttgt tagggaagaa caagtgccgt tcaaataggg    360
cggcaccttg acggtaccta accagaaagc cacggctaac tacgtgccag cagccgcggt    420
aatacgtagg tggcaagcgt tgtccggaat tattgggcgt aaagggctcg caggcggttt    480
cttaagtctg atgtgaaagc cccggctca accggggagg gtcattggaa actggggaac    540
ttgagtgcag aagaggagag tggaattcca cgtgtagcgg tgaaatgcgt agagatgtgg    600
aggaacacca gtggcgaagg cgactctctg gtctgtaact gacgctgagg agcgaaagcg    660
tggggagcga acaggattag ataccctggt agtccacgcc gtaaacgatg agtgctaagt    720
gttagggggt ttccgcccct tagtgctgca gctaacgcat taagcactcc gcctggggag    780
tacggtcgca agactgaaac tcaaaggaat tgacggggc ccgcacaagc ggtggagcat    840
gtggtttaat tcgaagcaac gcgaagaacc ttaccaggtc ttgacatcct ctgacaatcc    900
tagagatagg acgtcccctt cggggcaga gtgacaggtg gtgcatggtt gtcgtcagct    960
cgtgtcgtga gatgttgggg ttaagtcccg caacgagcgc aacccttgat cttagttgcc   1020
agcattcagt tgggcactct aaggtgactg ccggtgacaa accggaggaa gggtggggg   1080
atgacgtcaa atcatcatgc cccttatgac ctgggctaca cacgtgctac aatggacaga   1140
acaaagggca gcgaaaccgc gaggttaagc caatcccaca aatctgttct cagttcggat   1200
cgcagtctgc aactcgactg cgtgaagctg gaatcgctag taatcgcgga tca         1253

SEQ ID NO: 6             moltype = DNA   length = 1131
FEATURE                  Location/Qualifiers
source                   1..1131
                         mol_type = other DNA
                         organism = synthetic construct
SEQUENCE: 6
taacctacct ataagactgg gataacttcg ggaaaccgga gntaataccg gataacatgt     60
tgaaccgcat ggttcaacag tgaaagacgg tcttgctgtc acttatagat ggatccgcgc    120
cgcattagct agttggtaag gtaacggctt accaaggcaa cgatgcgtag ccgacctgag    180
agggtgatcg gccacactgg aactgagaca cggtccagac tcctacggga ggcagcagta    240
gggaatcttc gcaatgggc gaaagcctga cggagcaacg ccgcgtgagt gaagaaggtc    300
ttcggatcgt aaaactctgt tattagggaa gaacaaatgt gtaagtaact atgcacgtct    360
tgacggtacc taatcagaaa gccacggcta actacgtgcc agcagccgcg gtaatacgta    420
ggtggcaagc gttatccgga attattgggt gtaaagcgcg cgtaggcggt tttttaagtg    480
tgatgtgaaa gcccacggct caaccgtgga gggtcattgg aaactggaaa acttgagtgc    540
agaagaggaa agtggaattc catgtgtagc ggtgaaatgc gcagagatat ggaggaacac    600
cagtggcgaa ggcgactttc tggtctgtaa ctgacgctga gtgcgaaag cgtggggatc    660
aaacaggatt agataccctg gtagtccacg ccgtaaacga tgagtgctaa gtgttagggg    720
gtttccgccc cttagtgctg cagctaacgc attaagcact ccgcctgggg agtacgaccg    780
caaggttgaa actcaaagga attgacgggg acccgcacaa gcggtggagc atgtggttta    840
attcgaagca acgcgaagaa ccttaccaaa tcttgacatc ctctgacccc tctagagata    900
gagttttccc cttcggggga cagagtgaca ggtggtgcat ggttgtcgtc agctcgtgtc    960
gtgagatgtt gggttaagtc ccgcaacgag cgcaaccctt aagcttagtt gccatcatta   1020
agttgggcac tctaagttga ctgccggtga caaaccggag gaaggtgggg atgacgtcna   1080
atcatcntgc ncttatgat tngggctaca cacgtgctac aatggacaat a             1131

SEQ ID NO: 7             moltype = DNA   length = 1200
FEATURE                  Location/Qualifiers
source                   1..1200
                         mol_type = other DNA
                         organism = synthetic construct
SEQUENCE: 7
ttctatcacc aaaaacaggt caattaacag taggggatac acaagacttc cagttggtag     60
aaaacctgtc ggatgggagc aatcaagacc aaacaggaaa tacaacattt actgttagcg    120
attcatccat tgccacaata caaaacaaca actaacagc ggttgctcca gggaccgtga    180
cggtaacggc aaccctatgg tagctcatcc gacacagcaac aattacggtg aaaaagccta    240
```

```
caccagttcc gccatcgta ccacagcctg taaatccagt ggaaccaaag ccttcaggtg    300
caatagacat tattcgtact gttgaacaag gtatcgtgaa gtatcgagca gacgtatcat    360
tgaatcatgt ccaaatgcta gtacaacaaa tgactaatca agatgcacga acaattcgtc    420
tcgtgtaccc agcagaaaca gcaactgcaa aggcttattt gaatctttt agaaacgcag     480
gattgttttt atacaatcaa aatacggatc ttttcataca aacagagtta gcacaaatga    540
ggattccttt taaatcattc gatggcgtga cagaggatgt gtacttccat ctagctcctg    600
tcaagggacc acaacaggat atgattcata cgaatgccct aaacaatgaa caaatccaga    660
aagcaatgcc agatagagcg ataatttcat tactaggtac acccgtaaga atcgaaacga    720
atctacaaaa tcgcccagta atgattacgt taccgatttc gtctgagtta acagaagatc    780
aaattgcctc actacttatc tatgttgagc atagtgacga acaacggaa gtaaaacatg      840
ggcgtatagt ggagtttgta cctggggtga aaggtttcca gtttgaagtt gatcacttct    900
caacatatag cttagtatat acttcagaag ttcaagaagc tgaggaagaa gtagagcaaa    960
tagcaccata tattcaaggt ttcccagatg gcacatttaa accaaatgct tcggttacac    1020
gtgcacaaat ggcaacaatg ttagcacgtt ttttaacgaa tggtgacata ccaacggcaa    1080
gtgcaacttt taaagataca aagaatcatc cttctaaaga tgcgattgaa ttagtgaaag    1140
aaattggttt atttaacggt ataacggata caacatttaa tccaaatggg acgattacaa    1200

SEQ ID NO: 8           moltype = DNA   length = 1200
FEATURE                Location/Qualifiers
source                 1..1200
                       mol_type = other DNA
                       organism = synthetic construct
SEQUENCE: 8
cgctactggc gttaccgggg ctactggtgt tactggcgct accggcgcta ccggcgctac    60
cggcgttact ggcgttactg gttctacggg tgtaaccggc gctactggtt ctaccggcgc    120
taccggcgtt actggagtaa ctggggctac tggtgttgct ggttctacgg cgctactggc    180
cgcaatcgga cctactggcg ctactggcgt tactggcgct accggggcta ctggggtaac    240
tggggctacc ggcgttactg gggtaaccgg cgctactggc gctactggtg taaccggggc    300
taccggggct actggcttga ctggcgcaat cggacctact ggcaccactg gataactgg    360
ggctaccggc gttactggcg ttactggcgc taccggcgct ggggggctac cgggtgaaca    420
tggcgctact ggggtaactg gggctaccgg tgttgctggg gctacgggcg ctacgggcgt    480
tactggcgca atcggaccta ctggcgctac tggtgtaacc gggctaccg gcgttactgg     540
cgttactggg gctaccggcg ttactggggt aaccggcgct actggcttga ctggtgcaat    600
cggacctact ggcgctactg gagtaaccgg ggctaccggc gttactgggg ctactggcgt    660
tactgggta actgggctaa ccggcgttac tggcgttacc ggcgttgctg ggtctaccgc     720
cgttaccggc gttactggcg ctactggcgt tactggttct acgggagtga ccggcgctac    780
tggtattact ggttctacgg gtgtaaccgg ggctactggc gctactggtt ctactggggt    840
aaccggcgtt actggttcta cgggtgagac tggggtaact ggggctaccg gcattactgg    900
agtaaccggc gctactggca ttactggagt aaccggcgct actggcacta ctggagtaac    960
tggcgctacc ggcgttactg gcgctaccgg cgttgctggg gctacgggtg agaccggcgc    1020
tactggcact actggagtaa ctggggctac cggtgttgct ggttctacgg gcgcgactgg    1080
cgcaatcgga cctactggcg ttactggtgt aactgggct accggcgcaa tcggacctac    1140
tggcgttact ggagctaccg gcgttgctgg ggtaactggg gctactggcg ttactggtgc    1200

SEQ ID NO: 9           moltype = DNA   length = 1200
FEATURE                Location/Qualifiers
source                 1..1200
                       mol_type = other DNA
                       organism = synthetic construct
SEQUENCE: 9
tataaatcca gtaatgcttt ttctttttgt tcgtttacat tcataaaatc gtgtaacctt    60
ttaagctttt tccctttctg ctcttctaca ttgctttgaa gttttaatgt aacatactgc    120
cctttttca cgagtaaatc aataataaat ctacgaaaat catgatattg aataggtaca     180
tgatttacac aaccatactt tcctgctctt ctatactgtg agcactttaa atatttccat    240
tcagtccgtt caccattctt cttttcgaaga taggattgta cgataaccat atttgaacca    300
caaatcgcgc attttgctaa attacgaaat tcattccaag ctgtgatttt tgttttactc    360
ataataatgt cttttgatt tgctcgattc catatctctt catctacaat tttgggatgg     420
tgattaggaa aaacaaacca cttttctctc ggattgcgaa tttgtttttt cctaccgttc    480
acctgaccg aggtatattg attaaaata aacgtcccta tgtaaattgg attttgaaga      540
atacgctgaa cggatgttat ttgccaattt tttttagttt tagattttat ccccatttta    600
tttaactcat ttgaaatttt tttatatccc caccattga tatccaact atatatcctt      660
cgaacaaact tagattcctc ttcattaata atcaacttt gattaatacg gtcatacca      720
tacggtactt taccaatatg ctcacctctt cttactttca ccgccaaagc agcagtaata    780
ctcgaagata atgtccgact atactgcgcc gaaaataaag accataacta aaatgccata    840
tcatttttcc cagcttttac agaatcatag ccttcttcca cagaaacaat tctaacatta    900
tgagctaaaa gcacttctct tatctctaat gagtcctta aatcacgcgc taaacgagaa      960
atagacttaa agacaaccat atcaatttct ttcgccttcg ccttttgtaa taataattga    1020
atagcaggac gatccataaa taagtacca ctcatcccct catctttaaa aacacatttt     1080
tcattccaca taaatccatt acgctccaac caattcctac aaaatatctat ttggttttca    1140
atcgaggaaa cttgttcatc acgatctgtt gatacgcgaa cataaacagc ataagattcc    1200

SEQ ID NO: 10          moltype = DNA   length = 1200
FEATURE                Location/Qualifiers
source                 1..1200
                       mol_type = other DNA
                       organism = synthetic construct
SEQUENCE: 10
ctgtttagt cctcctaagt aatatttcat aacttcatat tttgcatgtg tatcatcaga     60
tagtagaatg tcaatttcat attctaaaat cggcaactta tgatatatga agtcgaaaaa    120
```

-continued

```
atctgtttcg gttgtgaatt caaattgttt taaagtatct ttgaaaaatc tttctcgatt    180
gagtaataat tgcaacaaat gattttctaa atgctttatt tctcgcattt ttttatgtat    240
ggcttttttgt ttagctattt cttttttgcat gtttttatta tttagattta catctaaatt   300
caattctttt aaaagaaaag attctgcttg tttgtgcgtc catccatgca atatcatcag    360
acctgaaaat tggtctattg gtcttctatt cccgcaccct gcgaaacaat aacagttgtt    420
gtctgatacg ttcacaacca tgctatcttt gttatctgca tggaagggac acttgcacat    480
gtaattttt ccccgctttc taacagttac cccgcaatag cttctaaga aatttataat      540
aggaagttta cttttaatta gatcgctttt ttgcatatca tcacacttct ttatctttga    600
aaataattt gatatgttta gcttggtttt ttcctcgttg atagaaaaca tctgtaagac     660
ctttttcctc caaacctttg aaggctcgtc caacgctaga gcgtgataaa ttgcaatgtc    720
ctattacatc ttcaatctta atttttcgt gttgttctgc acaaccttgc tgatgtagat     780
agagcaatac aagtttttca gtaggtgttg tttcttggac ttcgaaaatg tctttttatcg   840
tcaatattct gctcctcctg tcaaatttct ttatgaattt aactttaaca gatatttcat    900
tatgcgtcaa tatgacacat aagaattata taacgaaaat aattaaatcc tttaatataa    960
acgatttcta gcgagtaata aaaacgattc cttgattcat tttcggaaac acctgacgtc   1020
ttccctacga ttccttatat tttttgcggg gattattcat gtttctttgt caatcagcaa   1080
ggacaaacaa tcctcgctat tttgagagtg tattttcata ttccttcatg attttgtaga   1140
atgatgtttt tttgagattt agcatttgac tgaattctac accttgatt tctttgcttt    1200

SEQ ID NO: 11           moltype = DNA    length = 1200
FEATURE                 Location/Qualifiers
source                  1..1200
                        mol_type = other DNA
                        organism = synthetic construct
SEQUENCE: 11
gtttctcccg ttgctccggt tactcctgtt gccccagttg ggccggttgc tccgattgaa     60
cctgttgctc cggttggacc ggtctctccc gttgggccga tttctccagt tacaccggtt    120
gcgccggttt ctcccgttga accaattgag ccggttactc ctgttgcccc tgttgctcca    180
gttacaccag tcaagccggt tgggcctgtt attcctgtta ttcctgttgc tccggttgaa    240
ccggatgcac ccgtcgcccc ggtttctcct gtcgatccgg ttggaccagt ctccccagtt    300
gacccggttg atcctgtcgc gcctgttact cccgttgggc ctgttgggcc tgttgagccg    360
gtcgttcccg ttgctcctgt cggcccggtt attcctgtcg caccggtttc tccggttact    420
cccgtcgccc cggttactcc agttgaaccc gtttctcctg tcgatcctgt tgatccggtt    480
acaccagttg agcccgtgac cccagtcggg ccagtcaccc ctgttgatcc tgttgcacca    540
gttactccgg ttgggcctgt tgaacctgtc gatcccgttg cgccggttgg gcctgctgcg    600
ccagttgagc cggttgagcc agttggcccg atttctccag ttgaaccggt cgctcctgtc    660
tccccggtcg ctcctgttgg gccgatcggg ccagtagccc ctgtggctcc cgttatcccc    720
gttgccccag tcactccagt tggacccgtt tctcccgttg agccagttgc tcctgtttct    780
cctgttggac cagtctcccc agttgaccccg gttgatccgg tttctcctgt cgatcccgtt    840
gcgccggtta ttcctgttac accggtctct cctattgcgc cggttgggcc tgttactcca    900
gtcgctccgg ttggaccggt ttccggttgaacccgtgg ttccgccggttg gtcctgttggtc    960
ccagttactc ccgttgaacc agttgatccc gttataccag ttaccccagt cgctcctgtc   1020
gatcccattg cacccgttga gccggtggct cctgttactc ccgttgctcc ggttgagccg   1080
gttgggccgg ttgggccggt tacacccgtg accccagtcg ggccagtaac tcctgttgcc   1140
cctgttactc cggtcgatcc cgtttctcct gttgcacctg ttactccggt ctctcctgtt   1200

SEQ ID NO: 12           moltype = DNA    length = 1200
FEATURE                 Location/Qualifiers
source                  1..1200
                        mol_type = other DNA
                        organism = synthetic construct
SEQUENCE: 12
aaaactgtca gtgtaatgga tacacctgat ttcccggaga ttttattcc aacagctaaa      60
ggccaaggtc gtaacttgca agaactaaag gaaacttctg atattaactg gacatttatc    120
agtccttcag cggtatttga cccagacggg aaaagaactg gatttttatca gtcaggaaaa   180
gatcatcttc ttgtgaattc gaaaggcgaa agttatatca gctatgcaga ctatgccaatt    240
gcagtattgg atgaaattga aaatccaaaa catataaatg aacgctttac agttgttgga    300
gaagctgaat aagtgattga gtagaaacaa agggtaccat tagtgtcatc gctaatggta    360
tcttccttct aagaatgtac ggagacattg aaaactttgc aatcagagta gctgattatt    420
aaaaagggga tttatcacgt tccaatgaat attatcgagc tgatgacaga gtaggtgctt    480
agtgagttgg accaaaaaaa tatgtatgtg tataaaaagc tctgactaag acctttttgga    540
ttagttagag cttctttatt tgactgtgtt acccagtgta atcctccgta ttgtttaata    600
cactttagtt tgaaaatccg ggaaactctt ctacagttcc tatttcgtgt ttaaagtgtg    660
aatattccag cggggaactt tactgaaatg aggggtattt tcgaaaacac accagtatgc    720
tctatgacct gccgtcaatg acattaaaga aatgatttga tgtaaaaagg agcgatattc    780
gttaaaattct aggtagtagc catacatagc catataaaac acatgattaa ttctaaattc    840
tttactgatc gttcttaaat ttgatatact tgaaatacgt tagatctaac tgttttgcta    900
ctcaaatgag aatgatcgtt cttttaattat ttaagaatga gggagggatg aatgcatcaa   960
tgattctcagg gccttttctca gaataaaaga gtaatacatt ctaaggtggg attacatggc   1020
tagaaataaa gaatttgatg aaaaaaaaagc attaagaaaa gcaatggatc ttttctggga   1080
acagggttat gaaaaaacat ccatgcaaga cttggtggac catatgggca ttcaccgcag   1140
aagtatttat gatacatttg gcgacaaaca tactttattt atgcgagcct taagtcagta    1200

SEQ ID NO: 13           moltype = DNA    length = 1200
FEATURE                 Location/Qualifiers
source                  1..1200
                        mol_type = other DNA
                        organism = synthetic construct
SEQUENCE: 13
```

```
gtttctcccg ttgctccggt tactcctgtt gccccagttg ggccggttgc tccgattgaa    60
cctgttgctc cggttggacc ggtctctccc gttgggccga tttctccagt tacaccggtt   120
gcgccggttt ctcccgttga accaattgag ccggttactc ctgttgcccc tgttgctcca   180
gttacaccag tcaagccggt tgggcctgtt attcctgtta ttcctgttgc tccggttgaa   240
ccggatgcac ccgtcgcccc ggtttctcct gtcgatcccg ttggaccagt ctccccagtt   300
gaccggttg atcctgtcgc gcctgttact cccgttgggc ctgttgggcc tgttgagccg   360
gtcgttcccg ttgctcctgt cggcccggtt attcctgtcg caccggtttc tccggttact   420
cccgtcgccc cggttactcc agttgaaccc gtttctcctg tcgatcctgt tgatccggtt   480
acaccagttg agcccgtgac cccagtcggg ccagtcactc ctgttgatcc tgttgcacca   540
gttactccgg ttgggcctgt tgaacctgtc gatcccgttg cgccggttgg gcctgctcga   600
ccagttgagc cggttgagcc agttggcccg atttctccag ttgaaccggt cgctcctgtc   660
tccccggtcg ctcctgttgg gccgatcggg ccagtagccc ctgtggctcc cgttatcccc   720
gttgcccag tcactccagt tggacccgtt tctcccgttg agccagttgc tcctgtttct   780
cctgttggac cagtctcccc agttgacccg gttgatcccg tttctcctgt cgatcccgtt   840
gcgccggtta ttcctgttac accggtctct cctattgcgc cggttgggcc tgttactcca   900
gtcgctccgg ttggaccggt ttctccggtt gaaccagttg accctgctgc tcctgttggt   960
ccagttactc ccgttgaacc agttgatccc gttataccag ttaccccagt cgctcctgtc  1020
gatcccattg cacccgttga gccggtggct cctgttactc ccgttgctcc cggttgagccg  1080
gttgggccgg ttgggccggt tacacccgtg accccagtcg ggccagtaac tcctgttgcc  1140
cctgttactc cggtcgatcc cgtttctcct gttgcacctg ttactccggt ctctcctgtt  1200

SEQ ID NO: 14        moltype = DNA  length = 1200
FEATURE              Location/Qualifiers
source               1..1200
                     mol_type = other DNA
                     organism = synthetic construct
SEQUENCE: 14
aatataaaca aattgtgcta aatccgcttt atagtataag taacaaaacg atagataaac    60
aaacaacaca agttcattca tcgttttaaa ttaattaact cacgcattat cacatttac   120
tgaaggagtg tttgtaatgg aaaaattatt cgacgcaatt agaaacacag tcgatgctgg   180
aatcaaccaa gattggacaa aattaggaac tagcattgtt gacatcgttg acaatggtgt   240
aaaagttatt tctaaattta ttggtgcata attcagatta ttaatatcgt tttaataata   300
aaggagagat tataatgcaa aaattagcag aagcaatcgc aaacacagta aaagcaggac   360
aagaccatga ttggacaaaa ttaggtacaa gcatcgttga tatcgtagaa acggtgtaa   420
gtgcattaac taaagtattc ggtggttaat tttcgataaa taagaactta attataaata   480
aaataaacta aaggagagac tataatgact aaattagcag aagcaatcgc aaacgcagta   540
aaagcaggac aagaccaaga ttgggcaaaa ttaggtacaa gcatcgtagg tatcgcagaa   600
aacggaatcg gtttattagg taaagtattc ggattctaat atatgattag atggaccagg   660
gcaagcgctc tggtcttttt ttatttgcag attatttgtt attattaaaa agaataagaa   720
gtttgttcat taaaatttga aacggggata aattgtgaca tataaacata tcttattaga   780
tttcgatgat acaatagttg atttttacga tgcagaggaa aaggcatttt ataatatggc   840
aaaacattac ggtcattttc cgactaaaca agatttccaa catttagaa aggtcaatca   900
agcacactgg gaagctttc aacaaaatga attgacgaaa gaacaagttt tatctcatcg   960
atttattaat tatttcaatg attattacat agaagtagat ggtaaagaag cggatgagat  1020
atttagagat gaattagcta aagcgccgct taaattttc gatcaaacga ttgaaactat  1080
taaccagctg aaagataaac attcattata tattgttacg aatggtgtga caatcacgca  1140
acagcgtcgt attgctcaga caaatttaa tgatatattt aatggaatat ttatttcaga  1200

SEQ ID NO: 15        moltype = DNA  length = 1200
FEATURE              Location/Qualifiers
source               1..1200
                     mol_type = other DNA
                     organism = synthetic construct
SEQUENCE: 15
cactcgtgcc aagagctaat gatagcccaa gccctgtaac aattacttca actaatgatg    60
gagttgtcgt aatttgcgta attgcttgaa taacgatagg tgctccgagt gagattaaac   120
tcgatccagt acctggtaca ggtactccat tcacttggat tgtaagacct cctaatagac   180
ttgcagttgc agtgttagcg ataacagtga ttttatagaa tccagtttca ctaattacga   240
aagtatcagc atctaattga gaaattgctg taccaaactg tccaaca agatccaaca gtattaaatg   300
gtactggatc attaattcct aaatctaaag aaatcccacc ggagttaaat gcgtatagtc   360
ctgctgaaag tcctagtcct gatggtccag tcggtccagt cggtccagta gcccccagtcg   420
gtccagtagc tccagtagct ccagtgtcac cagtcggccc gtaggtccca gtagctccag   480
tgtcaccagt cggccccgta ggtccagtag ccccagtgtc accagtcggc cccgtaggtc   540
cagtagcccc agtgtcacca gtcggccccg taggtccagt agtcccagtg tcaccagtcg   600
gtccagtcgg ccccgtaggt ccagtcggcc cagtcggccc gtaggtccag tcggtccagt   660
ttggcccggt aggtacagtc ggccccgtag gtccagtcgg cccagtcggc ccggtcggcc   720
cagtcggaag ggtaaacggt ggtatcggtg gtaatgtagg tcctacaaga ttagggtcaa   780
atgcactagc tgataaagat tcatcgggat ttaatccatt tgaataatta ttatttgaca   840
taaattcacc tccataaagc gttcattata tagtagatgc aaaaccgaaa gaaaatgaca   900
cggacatttg aattattgaa aagaaatctt aaactacttg aacaatttaa aaaaatggaa   960
agtttagtat atgtataaca tatgattgat ttggaagagg gtgattatgt tgaacaagca  1020
aggaattaca attagtttat gtatgattgt tcgagatgag gaggagacaa tagcccgttg  1080
tttagacaca gttgaaaaaa ttgtggatga aattatagtg ttgatacag gctccgtcga  1140
tcgaacgaaa gaaatcgtag agaaatacac ttctaacata tatgatttcc agtggattga  1200

SEQ ID NO: 16        moltype = DNA  length = 1212
FEATURE              Location/Qualifiers
source               1..1212
                     mol_type = other DNA
```

```
                        organism = synthetic construct
SEQUENCE: 16
aatacatgca agtcgagcga acagataagg agcttgctcc tttgacgtta gcggcggacg    60
ggtgagtaac acgtgggtaa cctacntata agactggaat aactccggga aaccggggct   120
aatgccggat aacatttaga accgcatggt tctaaagtga aagatggttt tgctatcact   180
tatagatgga cccgcgccgt attagctagt tggtaaggta acggcttacc aaggcaacga   240
tacgtagccg acctgagagg gtgatcggcc acactggaac tgagacacgg tccagactcc   300
tacgggaggc agcagtaggg aatcttccgc aatgggcgaa agcctgacgg agcaacgccg   360
cgtgagtgat gaaggtcttc ggatcgtaaa actctgttat taggaagaa caaatgtgta   420
agtaactatg cacgtcttga cggtacctaa tcagaaagcc acggctaact acgtgccagc   480
agccgcggta atacgtaggt ggcaagcgtt atccggaatt attgggcgta aagcgcgcgt   540
aggcggtttc ttaagtctga tgtgaaagcc cacggctcnn ccgtggaggg tcattggaaa   600
ctgggaaact tgagtgcaga agaggaaagt ggaattccat gtgtagcggt gaaatgcgca   660
gagatatgga ggaacaccag tggcgaaggc gactttctgg tctgtaactg acgctgatga   720
gcgaaagcgt ggggatcaaa caggattaga taccctggta gtccacgccg taaacgatga   780
gtgctaagtg ttagggggtt tccgcccctt agtgctgcag ctaacgcatt aagcactccg   840
cctggggagt acgaccgcaa ggttgaaact caaaggaatt gacggggacc cgcacaagcg   900
gtggagcatg tggtttaatt cgaagcaacg cgaagaacct taccaaatct tgacatccTT   960
tgacaactct agagatagag ccttcccctt cggggacaa agtgacaggt ggtgcatggt  1020
tgtcgtcagc tcgtgtcgtg agatgttggg ttaagtcccg caacgagcgc aaccccttaaa  1080
cttagttgcc agcatttagt tgggcactct aagttgactg ccggtgacaa accggaggaa  1140
ggtggggatg acgtcaaatc atcatgcccc ttatgatttg ggctacacac gtgctacaat  1200
ggacaataca aa                                                     1212

SEQ ID NO: 17          moltype = DNA  length = 1116
FEATURE                Location/Qualifiers
source                 1..1116
                       mol_type = other DNA
                       organism = synthetic construct
SEQUENCE: 17
cgcattagct agttggtaag gtaacggctt accaaggcaa cgatgcgtag ccgacctgag    60
agggtgatcg gccacactgg aactgagaca cggtccagac tcctacggga ggcagcagta   120
gggaatcttc cgcaatgggc gaaagcctga cggagcaacg ccgcgtgagt gaagaaggtc   180
ttcggatcgt aaaactctgt tattagggaa gaacaaatgt gtaagtaact atgcacgtct   240
tgacggtacc taatcagaaa gccaccgcta actacgtgcc agcagccgcg gtaatacgta   300
ggtggcaagc gttatccgga attattgggc gtaaagcgcg cgtaggcggt tttttaagtc   360
tgatgtgaaa gcccacggct caaccgtgga gggtcattgg aaactggaaa acttgagtgc   420
agaagaggaa agtggaattc catgtgtagc ggtgaaatgc gcagagatat ggaggaacac   480
cagtggcgaa ggcgactttc tggtctgtaa ctgacgctgt gtgcgaaag cgtggggatc   540
aaacaggatt agataccctg gtagtccacg ccgtaaacga tgagtgctaa gtgttagggg   600
gtttcgcccc cttagtgctg cagctaacgc attaagcact ccgcctgggg agtacgaccg   660
caaggttgaa actcaaagga attgacgggg acccgcacaca gcggtggagc atgtggttta   720
attcgaagca acgcgaagaa ccttaccaaa tcttgacatc ctctgatccc tctagagata   780
gagttttccc cttcggggga cagagtgaca ggtggtgcat ggttgtcgtc agctcgtgtc   840
gtgagatgtt gggttaagtc ccgcaacgag cgcaaccctt aagcttagtt gccatcatta   900
agttgggcac tctaagttga ctgccggtga caaaccggag gaaggtgggg atgacgtcaa   960
atcatcatgc cccttatgat ttgggctaca cactgctac aatggacaat acaaagggta  1020
gcaaaaccgc gaggtcaagc aaatcccata aagttgttct cagttcggat tgtagtctgc  1080
aactcgacta catgaagctg gaatcgctag taatcg                             1116

SEQ ID NO: 18          moltype = DNA  length = 670
FEATURE                Location/Qualifiers
source                 1..670
                       mol_type = other DNA
                       organism = synthetic construct
SEQUENCE: 18
ctgagagggt gatcgccac actgggactg agacacggcc cagactccta cgggaggcag    60
cagtagggaa tcttccgcaa tggacgaaag tctgacggag caacgccgcg tgagtgatga   120
aggctttcgg gtcgtaaaac tctgttgtta gggaagaacta agtgctagtt gaataagcta   180
gcaccttgac ggtacctaac cagaaagcca cggctaacta cgtgccagca gccgcggtaa   240
tacgtaggtg gcaagcgtta tccggaatta ttgggcgtaa agcgcgcgca ggtggtttct   300
taagtctgat gtgaaagccc acggctcaac cgtggagggt cattggaaac tgggagactt   360
gagtgcagaa gaggaaagtg gaattccatg tgtagcggtg aaatgcgtag agatatggag   420
gaacaccagt ggcgaaggcg actttctggt ctgtaactga cgctgaggcg aaagcgtggg   480
gagcaaac aggattagat accctggtag tccacgccgt aaacgatgag tgctaagtgt   540
tagagggttt ccgccccta gtgctgaagt taacgcatta agcactccgc ctggggagta   600
cggccgcaag gctgaaactc aaaggaattg acggggcccg cacaagcgg tggagcatgt   660
ggtttaattc                                                         670

SEQ ID NO: 19          moltype = DNA  length = 1068
FEATURE                Location/Qualifiers
source                 1..1068
                       mol_type = other DNA
                       organism = synthetic construct
SEQUENCE: 19
catggttcga aattgaaagg cggcttcggc tgtcacttat ggatggaccc gcgtcgcatt    60
agctagttgg tgaggtaacg gctcaccaag gcaacgatgc gtagccgacc tgagagggtg   120
atcggccaca ctgggactga gacacggccc agactcctac gggaggcagc agtagggaat   180
cttccgcaat ggacgaaagt ctgacggagc aacgccgcgt gagtgatgaa ggctttcggg   240
```

```
tcgtaaaact ctgttgttag ggaagaacaa gtgctagttg aataagctgg caccttgacg    300
gtacctaacc agaaagccac ggctaactac gtgccagcag ccgcggtaat acgtaggtgg    360
caagcgttat ccggaattat tgggcgtaaa gcgcgcgcag gtggtttctt aagtctgatg    420
tgaaagccca cggctcaacc gtggagggtc attggaaact gggagacttg agtgcagaag    480
aggaaagtgg aattccatgt gtagcggtga aatgcgtaga gatatggagg aacaccagtg    540
gcgaaggcga ctttctggtc tgtaactgac actgaggcgc gaaagcgtgg ggagcaaaca    600
ggattagata ccctggtagt ccacgccgta aacgatgagt gctaagtgtt agagggtttc    660
cgcccttag tgctgaagtt aacgcattaa gcactccgcc tggggagtac ggccgcaagg     720
ctgaaactca aaggaattga cggggcccg cacaagcggt ggagcatgtg gtttaattcg     780
aagcaacgcg aagaaccta ccaggtcttg acatcctctg aaaaccctag agataggct     840
tctccttcgg gagcagagtg acaggtggtg catggttgtc gtcagctcgt gtcgtgagat    900
gttgggttaa gtcccgcaac gagcgcaacc cttgatctta gttgccatca ttaagttggg    960
cactctaagg tgactgccgg tgacaaaccg gaggaaggtg gggatgacgt caaatcatca    1020
tgcccttat gacctgggct acacacgtgc tacaatggac ggtacaaa                  1068

SEQ ID NO: 20           moltype = DNA   length = 1144
FEATURE                 Location/Qualifiers
source                  1..1144
                        mol_type = other DNA
                        organism = synthetic construct
SEQUENCE: 20
aaccggggct aataccgaat aacactttg acctcatggt cgaatgttaa aagacggttt     60
cggctgtcac tacaggatgg gcccgcggcg cattagctag ttggtgaggt aacggctcac    120
caaggcaacg atgcgtagcc gacctgagag ggtgatcggc cacactggga ctgagacacg    180
gcccagactc ctacggagg cagcagtagg gaatcttcca caatgacga aagtctgatg     240
gagcaacgcc gcgtgagtga agaaggattt cggttcgtaa aactctgttg caagggaaga   300
acaagtagcg tagtaactgg cgctaccttg acggtacctt gttagaaagc cacggctaac   360
tacgtgccag cagccgcggt aatacgtagg tggcaagcgt tgtccggaat tattgggcgt   420
aaagcgcgcg caggtggttt cttaagtctg atgtgaaagc ccacggctca accgtggagg   480
gtcattggaa actgggaaac ttgagtgcag aagaggatag tggaattcca agtgtagcgg   540
tgaaatgcgt agagatttgg aggaacacca gtggcgaagg cgactatctg gtctgtaact   600
gacactgagg cgcgaaagcg tggggagcaa acaggattag ataccctggt agtccacgcc   660
gtaaacgatg agtgctaagt gttgggggt tccgcccct cagtgctgca gctaacgcat    720
taagcactcc gcctggggag tacggtcgca agactgaaac tcaaaggaat tgacgggggc   780
ccgcacaagc ggtggagcat gtggtttaat tcgaagcaac gcgaagaacc ttaccaggtc   840
ttgacatccc attgaccact gtagagatac agttttccct tcggggacaa cggtgacagg   900
tggtgcatgg ttgtcgtcag ctcgtgtcgt gagatgttgg gttaagtccc gcaacgagcg   960
caacccttat tcttagttgc catcatttag ttgggcactc taaggagact gccggtgaca   1020
aaccggagga aggtggggat gacgtcaaat catcatgccc cttatgacct gggctacaca   1080
cgtgctacaa tggacggtac aaacgttgc caacccgcga gggggagcta atccgataaa    1140
accg                                                                 1144

SEQ ID NO: 21           moltype = DNA   length = 977
FEATURE                 Location/Qualifiers
source                  1..977
                        mol_type = other DNA
                        organism = synthetic construct
SEQUENCE: 21
tgtggatggg ctcacggcct atcagcttgt tggtggggta atggcctacc aaggcgacga    60
cgggtagccg gcctgagagg gtgaccggcc acactgggac tgagacacgg cccagactcc    120
tacgggaggc agcagtgggg aatattgcac aatgggcgca agcctgatgc agcgacgccg    180
cgtgagggat gacggccttc gggttgtaaa cctctttcag cacggaagaa gcgaaagtga    240
cggtacgtgc agaagaagcg ccggctaact acgtgccagc agccgcggta atacgtaggg    300
cgcaagcgtt gtccggaatt attgggcgta aagagctcgt aggcggtttg tcgcgtctgc    360
tgtgaaagcc cggggcttaa ccccgggtgt gcagtggata cgggcagact tgagtgcagt    420
agggggagact ggaactcctg gtgtagcggt gaaatgcgca gatatcagga agaacaccga    480
tggcgaaggc aggtctctgg gctgttactg acgctgagga gcgaaagcat ggggagcgaa   540
caggattaga taccctggta gtccatgccg taaacgttgg gcactaggtg tgggggacat    600
tccacgtttt ccgcgccgta gctaacgcat taagtgcccc gcctggggag tacggccgca    660
aggctaaaac tcaaaggaat tgacgggggc ccgcacaagc ggcggagcat gcggattaat    720
tcgatgcaac gcgaagaacc ttaccaaggc ttgacataca ccggatcggc tcagagatga    780
gttttcctcc ttgtggggct ggtgtacagg tggtgcatgg ttgtcgtcag ctcgtgtcgt    840
gagatgttgg gttaagtccc gcaacgagcg caaccctcgt tctatgttgc cagcacgtga    900
tggtggggac tcataggaga ctgccggggt caactcggag gaaggtgggg atgacgtcaa    960
atcatcatgc cccttat                                                    977
```

MICROBIAL COMPOSITIONS FOR THE TREATMENT OF SKIN DISEASES

CROSS-REFERENCE

This application is a continuation of International Application No. PCT/US2022/079637, filed Nov. 10, 2022, which claims the benefit of U.S. Provisional Application No. 63/278,134, filed Nov. 11, 2021, the disclosures of which are incorporated herein by reference in their entirety.

SEQUENCE LISTING

The application contains a Sequence Listing which has been submitted electronically in XML format and is hereby incorporated by reference in its entirety. Said XML copy was created on Jan. 16, 2024, is named as 202421-701301-SL and is 43,274 bytes in size.

SUMMARY OF THE INVENTION

Disclosed herein are compositions. In some embodiments, a composition comprises: bacterial strains that are purified, wherein the bacterial strains comprise: a first strain, which comprises a 16s rRNA sequence with at least 97% sequence identity to SEQ ID NO: 4; a second strain, which comprises a 16s rRNA sequence with at least 97% sequence identity to SEQ ID NO: 1; and a third strain, which comprises a 16s rRNA sequence with at least 97% sequence identity to SEQ ID NO: 2; and wherein (a) the bacterial strains are lyophilized; or (b) the composition is formulated for delivery to a skin. In some embodiments, the first strain comprises the 16s rRNA sequence with at least 97% sequence identity over at least 1000 bases to SEQ ID NO: 4. In some embodiments, the second strain comprises the 16s rRNA sequence with at least 97% sequence identity over at least 1000 bases to SEQ ID NO: 1. In some embodiments, the third strain comprises the 16s rRNA sequence with at least 97% sequence identity over at least 1000 bases to SEQ ID NO: 2. In some embodiments, the first strain further comprises a sequence with at least 95% sequence identity to SEQ ID NO: 11, SEQ ID NO: 12, or both. In some embodiments, the first strain further comprises having a sequence of SEQ ID NO: 11, SEQ ID NO: 12, or both. In some embodiments, the second strain further comprises a sequence with at least 95% sequence identity to SEQ ID NO: 15. In some embodiments, the second strain further comprises having a sequence of SEQ ID NO: 15. In some embodiments, the third strain further comprises sequence with at least 95% sequence identity to SEQ ID NO: 7, SEQ ID NO: 8, or both. In some embodiments, the third strain further comprises having a sequence of SEQ ID NO: 7, SEQ ID NO: 8, or both. In some embodiments, the composition is formulated as: a suspension, an emulsion, a cream, a lotion, a tincture, a gel, a foam, a powder, an ointment, a paste, or an oil. In some embodiments, the composition further comprises a fourth bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial strains are grown in aerobic conditions. In some embodiments, the bacterial strains are grown without animal products. In some embodiments, the bacterial strains are grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: bacterial strains that are purified, wherein the bacterial strains comprise: a first strain, which comprises a 16s rRNA sequence with at least 97% sequence identity to SEQ ID NO: 5; a second strain, which comprises a 16s rRNA sequence with at least 97% sequence identity to SEQ ID NO: 1; and a third strain, which comprises a 16s rRNA sequence with at least 97% sequence identity to SEQ ID NO: 2; and wherein (a) the bacterial strains are lyophilized; or (b) the composition is formulated for delivery to a skin. In some embodiments, the first strain comprises the 16s rRNA sequence with at least 97% sequence identity over at least 1000 bases to SEQ ID NO: 5. In some embodiments, the second strain comprises the 16s rRNA sequence with at least 97% sequence identity over at least 1000 bases to SEQ ID NO: 1. In some embodiments, the third strain comprises the 16s rRNA sequence with at least 97% sequence identity over at least 1000 bases to SEQ ID NO: 2. In some embodiments, the first strain further comprises a sequence with at least 95% sequence identity to SEQ ID NO: 13. In some embodiments, the first strain further comprises having a sequence of SEQ ID NO: 13. In some embodiments, the second strain further comprises a sequence with at least 95% sequence identity to SEQ ID NO: 15. In some embodiments, the second strain further comprises having a sequence of SEQ ID NO: 15. In some embodiments, the third strain further comprises a sequence with at least 95% sequence identity to SEQ ID NO: 7, SEQ ID NO: 8, or both. In some embodiments, the third strain further comprises having a sequence of SEQ ID NO: 7, SEQ ID NO: 8, or both. In some embodiments, the composition is formulated as: a suspension, an emulsion, a cream, a lotion, a tincture, a gel, a foam, a powder, an ointment, a paste, or an oil. In some embodiments, the composition further comprises a fourth bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial strains are grown in aerobic conditions. In some embodiments, the bacterial strains are grown without animal products. In some embodiments, the bacterial strains are grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: bacterial strains that are purified, wherein the bacterial strains comprise: a first strain, which comprises a 16s rRNA sequence with at least 97% sequence identity to SEQ ID NO: 5; a second strain, which comprises a 16s rRNA sequence with at least 97% sequence identity to SEQ ID NO: 3; and a third strain, which comprises a 16s rRNA sequence with at least 97% sequence identity to SEQ ID NO: 6; and wherein (a) the bacterial strains are lyophilized; or (b) the composition is formulated for delivery to a skin. In some embodiments, the first strain comprises the 16s rRNA sequence with at least 97% sequence identity over at least 1000 bases to SEQ ID NO: 5. In some embodiments, the second strain comprises the 16s rRNA sequence with at least 97% sequence identity over at least 1000 bases to SEQ ID NO: 3. In some embodiments, the third strain comprises the 16s rRNA sequence with at least 97% sequence identity over at least 1000 bases to SEQ ID NO: 6. In some embodiments, the first strain further comprises a sequence with at least 95% sequence identity to SEQ ID NO: 13. In some embodiments, the first strain further comprises having a sequence of SEQ ID NO: 13. In some embodiments, the second strain further comprises a sequence with at least 95% sequence identity to SEQ ID NO: 9, SEQ ID NO: 10, or both. In some embodiments, the second strain further comprises having a sequence of SEQ ID NO: 9, SEQ ID NO: 10, or both. In some embodiments, the third strain further comprises a sequence with at least 95% sequence identity to SEQ ID NO: 14. In some embodiments, the third strain further comprises having a sequence of SEQ ID NO: 14. In some embodiments, the composition is formulated as: a suspension, an emulsion, a cream, a lotion, a tincture, a gel, a foam, a powder, an ointment, a paste, or an oil. In some embodiments, the composition further comprising a fourth bacterial strain. In some embodiments, the composition comprises at least 10^3 colony forming units (cfu) per gram of bacteria. In some embodiments, the composition comprises 10^3 to 10^2 colony forming units (cfu) per gram of bacteria. In some embodiments, the bacterial strains are grown in aerobic conditions. In some embodiments, the bacterial strains are grown without animal products. In some embodiments, the bacterial strains are grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: bacterial strains that are purified, wherein the bacterial strains comprise at least two of the following bacterial strains: a first strain, which comprises a 16s rRNA sequence with at least 97% sequence identity to SEQ ID NO: 4; a second strain, which comprises a 16s rRNA sequence with at least 97% sequence identity to SEQ ID NO: 1; a third strain, which comprises a 16s rRNA sequence with at least 97% sequence identity to SEQ ID NO: 2; a fourth strain, which comprises a 16s rRNA sequence with at least 97% sequence identity to SEQ ID NO: 5; a fifth strain, which comprises a 16s rRNA sequence with at least 97% sequence identity to SEQ ID NO: 6; and a sixth strain, which comprises a 16s rRNA sequence with at least 97% sequence identity to SEQ ID NO: 3; and wherein (a) the at least two bacterial strains are lyophilized; or (b) the composition is formulated for delivery to a skin. In some embodiments, the first strain further comprises a sequence with at least 95% sequence identity to SEQ ID NO: 11, SEQ ID NO: 12, or both. In some embodiments, the first strain further comprises having a sequence of SEQ ID NO: 11, SEQ ID NO: 12, or both. In some embodiments, the second strain further comprises a sequence with at least 95% sequence identity to SEQ ID NO: 15. In some embodiments, the second strain further having a sequence of SEQ ID NO: 15. In some embodiments, the third strain further comprises a sequence with at least 95% sequence identity to SEQ ID NO: 7, SEQ ID NO: 8, or both. In some embodiments, the third strain further comprises having a sequence of SEQ ID NO: 7, SEQ ID NO: 8, or both. In some embodiments, the fourth strain further comprises a sequence with at least 95% sequence identity to SEQ ID NO: 13. In some embodiments, the fourth strain further comprises having a sequence of SEQ ID NO: 13. In some embodiments, the fifth strain further comprises a sequence with at least 95% sequence identity to SEQ ID NO: 14. In some embodiments, the fifth strain further comprises having a sequence of SEQ ID NO: 14. In some embodiments, the sixth strain further comprises a sequence with at least 95% sequence identity to SEQ ID NO: 9, SEQ ID NO: 10, or both. In some embodiments, the sixth strain further comprises having a sequence of SEQ ID NO: 9, SEQ ID NO: 10, or both. In some embodiments, the composition is formulated as: a suspension, an emulsion, a cream, a lotion, a tincture, a gel, a foam, a powder, an ointment, a paste, or an oil. In some embodiments, the first strain comprises the 16s rRNA sequence with at least 97% sequence identity over at least 1000 bases to SEQ ID NO: 4. In some embodiments, the first strain comprises the 16s rRNA sequence with at least 97% sequence identity over at least 1000 bases to SEQ ID NO: 1. In some embodiments, the first strain comprises the 16s rRNA sequence with at least 97% sequence identity over at least 1000 bases to SEQ ID NO: 2. In some embodiments, the fourth strain comprises the 16s rRNA sequence with at least 97% sequence identity over at least 1000 bases to SEQ ID NO: 4. In some embodiments, the fifth strain comprises the 16s rRNA sequence with at least 97% sequence identity over at least 1000 bases to SEQ ID NO: 1. In some embodiments, the sixth strain comprises the 16s rRNA sequence with at least 97% sequence identity over at least 1000 bases to SEQ ID NO: 2. In some embodiments, the bacterial strains comprise bacterial strains the first strain and the second strain. In some embodiments, the bacterial strains comprise the fourth strain and the second strain. In some embodiments, the bacterial strains comprise the fourth strain and the sixth strain. In some embodiments, the bacterial strains comprise the first strain and the third strain. In some embodiments, the bacterial strains comprise the second strain and the third strain. In some embodiments, the bacterial strains comprise the fifth strain and the sixth strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial strains are grown in aerobic conditions. In some embodiments, the bacterial strains are grown without animal products. In some embodiments, the bacterial strains are grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: a bacterial strain that is purified, wherein the bacterial strain comprises: a 16s rRNA sequence with at least 97% sequence identity to SEQ ID NO: 4; and wherein (a) the bacterial strain is lyophilized; or (b) the composition is formulated for delivery to a skin. In some embodiments, the bacterial strain comprises the 16s rRNA sequence with at least 97% sequence identity over at least 1000 bases to SEQ ID NO: 4. In some embodiments, the bacterial strain further comprises a sequence with at least 95% sequence identity to SEQ ID NO: 11, SEQ ID NO: 12, or both. In some embodiments, the bacterial strain further comprises having a sequence of SEQ ID NO: 11, SEQ ID NO: 12, or both. In some embodiments, the composition is formulated as: a suspension, an emulsion, a cream, a lotion, a tincture, a gel, a foam, a powder, an ointment, a paste, or an oil. In some embodiments, the composition further comprises a second bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, a bacterial strain is grown in aerobic conditions. In some embodiments, a bacterial strain is grown without animal products. In some embodiments, a bacterial strain is grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: a bacterial strain that is purified, wherein the bacterial strain comprises: a 16s rRNA sequence with at least 97% sequence identity to SEQ ID NO: 1; and wherein (a) the bacterial strain is lyophilized; or (b) the composition is formulated for delivery to a skin. In some embodiments, the bacterial strain comprises the 16s rRNA sequence with at least 97% sequence identity over at least 1000 bases to SEQ ID NO: 1. In some embodiments, the bacterial strain further comprises a sequence with at least 95% sequence identity to SEQ ID NO: 15. In some embodiments, the bacterial strain further comprises having a sequence of SEQ ID NO: 15. In some embodiments, the composition is formulated as: a suspension, an emulsion, a cream, a lotion, a tincture, a gel, a foam, a powder, an ointment, a paste, or an oil. In some embodiments, the composition further comprises a second bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, a bacterial strain is grown in aerobic conditions. In some embodiments, a bacterial strain is grown without animal products. In some embodiments, a bacterial strain is grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: a bacterial strain that is purified, wherein the bacterial strain comprises: a 16s rRNA sequence with at least 97% sequence identity to SEQ ID NO: 2; and wherein (a) the bacterial strain is lyophilized; or (b) the composition is formulated for delivery to a skin. In some embodiments, the bacterial strain comprises the 16s rRNA sequence with at least 97% sequence identity over at least 1000 bases to SEQ ID NO: 2. In some embodiments, the bacterial strain further comprises a sequence with at least 95% sequence identity to SEQ ID NO: 7, SEQ ID NO: 8, or both. In some embodiments, the bacterial strain further comprises having a sequence of SEQ ID NO: 7, SEQ ID NO: 8, or both. In some embodiments, the composition is formulated as: a suspension, an emulsion, a cream, a lotion, a tincture, a gel, a foam, a powder, an ointment, a paste, or an oil. In some embodiments, the composition further comprises a second bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, a bacterial strain is grown in aerobic conditions. In some embodiments, a bacterial strain is grown without animal products. In some embodiments, a bacterial strain is grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: a bacterial strain that is purified, wherein the bacterial strain comprises: a 16s rRNA sequence with at least 97% sequence identity to SEQ ID NO: 5; and wherein (a) the bacterial strain is lyophilized; or (b) the composition is formulated for delivery to a skin. In some embodiments, the bacterial strain comprises the 16s rRNA sequence with at least 97% sequence identity over at least 1000 bases to SEQ ID NO: 5. In some embodiments, the bacterial strain further comprises a sequence with at least 95% sequence identity to SEQ ID NO: 13. In some embodiments, the bacterial strain further comprises having a sequence of SEQ ID NO: 13. In some embodiments, the composition is formulated as: a suspension, an emulsion, a cream, a lotion, a tincture, a gel, a foam, a powder, an ointment, a paste, or an oil. In some embodiments, the composition further comprises a second bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, a bacterial strain is grown in aerobic conditions. In some embodiments, a bacterial strain is grown without animal products. In some embodiments, a bacterial strain is grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: a bacterial strain that is purified, wherein the bacterial strain comprises: a 16s rRNA sequence with at least 97% sequence identity to SEQ ID NO: 6; and wherein (a) the bacterial strain is lyophilized; or (b) the composition is formulated for delivery to a skin. In some embodiments, the bacterial strain comprises the 16s rRNA sequence with at least 97% sequence identity over at least 1000 bases to SEQ ID NO: 6. In some embodiments, the bacterial strain further comprises a sequence with at least 95% sequence identity to SEQ ID NO: 14. In some embodiments, the bacterial strain further comprises having a sequence of SEQ ID NO: 14. In some embodiments, the composition is formulated as: a suspension, an emulsion, a cream, a lotion, a tincture, a gel, a foam, a powder, an ointment, a paste, or an oil. In some embodiments, the composition further comprises a second bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, a bacterial strain is grown in aerobic conditions. In some embodiments, a bacterial strain is grown without animal products. In some embodiments, a bacterial strain is grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with *S. aureus* cause a reduction in expression of at least one of the following genes: gmk, agr, psma, saeR, ccpA, and SigB in *S. aureus*, wherein the reduction in expression is measured by a fluorescence reporter assay. In some embodiments, the bacterial strains are present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

In some embodiments, a composition comprises: a bacterial strain that is purified, wherein the bacterial strain comprises: a 16s rRNA sequence with at least 97% sequence identity to SEQ ID NO: 3; and wherein (a) the bacterial strain is lyophilized; or (b) the composition is formulated for delivery to a skin. In some embodiments, the bacterial strain comprises the 16s rRNA sequence with at least 97% sequence identity over at least 1000 bases to SEQ ID NO: 3. In some embodiments, the bacterial strain further comprises a sequence with at least 95% sequence identity to SEQ ID NO: 9, SEQ ID NO: 10, or both. In some embodiments, the bacterial strain further comprises having a sequence of SEQ ID NO: 9, SEQ ID NO: 10, or both. In some embodiments, the composition is formulated as: a suspension, an emulsion, a cream, a lotion, a tincture, a gel, a foam, a powder, an ointment, a paste, or an oil. In some embodiments, the composition further comprises a second bacterial strain. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, a bacterial strain is grown in aerobic conditions. In some embodiments, a bacterial strain is grown without animal products. In some embodiments, a bacterial strain is grown in Tryptic Soy Broth (TSB). In some embodiments, the composition when stored in a sealed container placed at 20° C. retains at least about: 10^4 cfu after 6 months, as measured by cfu counts. In some embodiments, the composition further comprises an excipient. In some embodiments, the composition further comprises a lyoprotectant. In some embodiments, the composition further comprises an emollient. In some embodiments, the composition further comprises or a salt thereof. In some embodiments, the bacterial strains when contacted with S. aureus cause a reduction in expression of at least one of the following genes: gmk, agr, psma, saeR, ccpA, and SigB in S. aureus, wherein the reduction in expression is measured by a fluorescence reporter assay. In some embodiments, the bacterial strains are present in an amount effective to suppress virulence of S. aureus as measured by a reduction in expression of at least one of the following genes: gmk, agr, psma, saeR, ccpA, and SigB in S. aureus wherein the reduction in expression is measured by a fluorescence reporter assay.

Also disclosed herein are methods of administering the composition described above. In some embodiments, a method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, a method comprises administering an amount sufficient to reduce symptoms associated with atopic dermatitis. In some embodiments, a method comprises administering the composition to a subject who has an eczema prone microbiome prior to the administration. In some embodiments, a method comprises administering an amount sufficient to reduce symptoms associated with dry skin.

Also disclosed herein are methods of administering a composition described above. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, a method comprises administering an amount sufficient to suppress virulence of S. aureus as measured by a reduction in expression of at least one of the following genes: gmk, agr, psma, saeR, ccpA, and SigB in S. aureus, wherein the reduction in expression is measured by a fluorescence reporter assay. In some embodiments, the method of administering is topical administration.

Also disclosed herein are compositions, such as the compositions disclosed above, for use in the treatment of a skin condition. Disclosed herein are compositions for use in the treatment of inflammation.

Also disclosed herein are method for treatment of inflammation, comprising: topically administering a composition comprising a bacterial strain, which comprises a 16s rRNA sequence with at least 97% sequence identity to SEQ ID NO: 1 to a subject in need thereof, wherein the bacterial strain is purified, and wherein the bacterial strain is present in an amount sufficient for treatment of inflammation.

Also disclosed herein are methods for reducing growth of Staphylococcus aureus on skin of a subject, comprising: topically administering to a skin of the subject a pharmaceutical composition comprising: a first bacterial strain, which comprises a 16s rRNA sequence with at least 97% sequence identity to SEQ ID NO: 5; a second bacterial strain, which comprises a 16s rRNA sequence with at least 97% sequence identity to SEQ ID NO: 1; and a third bacterial strain, which comprises a 16s rRNA sequence with at least 97% sequence identity to SEQ ID NO: 2, wherein the bacterial strains are purified, and wherein the bacterial strains are viable, and present in an amount sufficient for reduction of S. aureus on a skin of the subject in need thereof.

Also disclosed herein are methods for reduction of symptoms associated with atopic dermatitis, comprising: topically administering a composition comprising a bacterial strain, which comprises a 16s rRNA sequence with at least 97% sequence identity to SEQ ID NO: 5, to a subject in need thereof, wherein the bacterial strain is purified, and wherein the bacterial strain is present in an amount sufficient for the reduction of symptoms associated with atopic dermatitis.

Also disclosed herein are methods for reducing an incidence of a condition associated with inflammation comprising: topically administering a composition comprising: a first bacterial strain, which comprises a 16s rRNA sequence with at least 97% sequence identity to SEQ ID NO: 1; and a second bacterial strain, which comprises a 16s rRNA sequence with at least 97% sequence identity to SEQ ID NO: 6, to a subject in need thereof, wherein the bacterial strains are purified, wherein the bacterial strains are present in an amount sufficient for a reduction of the incidence of a condition associated with inflammation and wherein the condition associated with inflammation comprises an itch, a rash, a redness, a pain, a swelling, a blistering, or a scaling.

Also disclosed herein are methods of administering the compositions described above. In some embodiments, a method can comprise administering an amount sufficient to treat a condition selected from the group consisting of: pruritis, an aesthetic condition, and body odor. In some embodiments, the aesthetic condition comprises wrinkles or appearance of aging.

Also disclosed herein are methods for reducing growth of Staphylococcus aureus on skin of a subject, comprising: topically administering to a skin of the subject, a composition comprising: a first bacterial strain, which comprises a 16s rRNA sequence with at least 97% sequence identity to SEQ ID NO: 5; a second bacterial strain, which comprises a 16s rRNA sequence with at least 97% sequence identity to SEQ ID NO: 1; and a third bacterial strain, which comprises a 16s rRNA sequence with at least 97% sequence identity to SEQ ID NO: 2, wherein the bacterial strains are purified, and wherein the bacterial strains are viable, and present in an amount sufficient for enhancing skin appearance of the subject. In some embodiments, the enhancing skin appearance of the subject comprises reducing wrinkles, decreasing lesion size, decreasing pore size, decreasing pore density, decreasing wrinkle occurrence, decreasing wrinkle depth, decreasing age spots, or increasing skin elasticity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows percent of two strain combinations that inhibit expression of agr and psmA (left) or inhibit expression agr, psmA, and sigB (right) of *Staphylococcus aureus*. Combinations of strains that inhibit multiple functions of *S. aureus* are rare.

FIG. 2 shows inhibition of different *S. aureus* promoter-reporter constructs when reporter strains of *S. aureus* were mixed with single strain, two strains or three strains of Strain jl.83, Strain jl.27 and Strain jl.77.

FIG. 3 shows inhibition of different *S. aureus* promoter-reporter constructs when reporter strains of *S. aureus* were mixed with single strain, two strains or three strains of Strain jl.21, Strain jl.68, and Strain jl.121.

FIG. 4 shows inhibition of different *S. aureus* promoter-reporter constructs when the reporter strains of *S. aureus* were mixed with single strain, two strains or three strains of Strain jl.27, Strain jl.68, and Strain jl.121.

FIG. 5 shows inhibition of different *S. aureus* promoter-reporter constructs (agr, psmA, GMK) when the reporter strains of *S. aureus* were mixed with the three-strain mixture of Strain jl.83, Strain jl.27 and Strain jl.77 in the presence of additional environmental conditions (e.g., different nutrients). This data shows the strain combination retained *S. aureus* inhibition function across different nutrients.

FIG. 6 shows inhibition of different *S. aureus* promoter-reporter constructs (agr, psmA, GMK) when the reporter strains of *S. aureus* were mixed with the three-strain mixture of Strain jl.21, Strain jl.68, and Strain jl.121 in the presence of additional environmental conditions (e.g., different nutrients). This data shows the strain combination retained *S. aureus* inhibition function across different nutrients.

FIG. 7 shows inhibition of different *S. aureus* promoter-reporter constructs (agr, psmA, GMK) when the reporter strains of *S. aureus* were mixed with the three-strain mixture of Strain jl.27, Strain jl.68, and Strain jl.121 in the presence of additional environmental conditions (e.g., different nutrients). This data shows the strain combination retained *S. aureus* inhibition function across different nutrients.

FIG. 8 shows inhibition of different *S. aureus* promoter-reporter constructs (agr, psmA, GMK) when the reporter strains of *S. aureus* were mixed with the three-strain mixture of Strain jl.83, Strain jl.27 and Strain jl.77 in the presence of thiamine. The presence of thiamine enhances the inhibition of *S. aureus* by the three-strain mixture.

FIG. 9 shows growth of different skin isolates in animal free media compared to animal-based medium. This figure shows increased growth for most isolated strains in animal-free media.

FIG. 10 shows inhibition of different *S. aureus* strains when grown with the strains Strain jl.83, Strain jl.27 and Strain jl.77. This figure shows the combination of the isolates are able to inhibit growth of numerous *S. aureus* isolates.

FIG. 11 shows inhibition of different *S. aureus* strains when grown with the strains Strain jl.21, Strain jl.68, and Strain jl.121. This figure shows the combination of the isolates are able to inhibit growth of numerous *S. aureus* isolates.

FIG. 12 shows inhibition of different *S. aureus* strains when grown with the strains Strain jl.27, Strain jl.68, and Strain jl.121. This figure shows the combination of the isolates are able to inhibit growth of numerous *S. aureus* isolates.

FIG. 13 shows inhibition of different *S. aureus* promoter-reporter constructs when the reporter strains of *S. aureus* were mixed with strain combinations of Strain jl.27.

FIG. 17A shows a zoomed-out picture of the plate. FIG. 17B shows a zoomed-in picture of the plate.

FIG. 18A shows the CFU of *S. aureus* and the expression of GMK and agr in a *S. aureus* monoculture. FIG. 18B shows the CFU of *S. aureus* and the expression of GMK and agr in 1:1 coculture with a WT strain of *S. aureus* (not having the agr/GMK reporter). FIG. 18C shows the CFU of *S. aureus* and the expression of GMK and agr in 1:1 coculture with the three-strain mix of Strain jl.27, Strain jl.68, and Strain jl.77. FIG. 18D shows the CFU of *S. aureus* and the expression of GMK and agr in 1:1 coculture with the single Strain jl.68. FIG. 18E shows the CFU of *S. aureus* and the expression of GMK and agr in culture with supernatant from a three-strain mix of Strain jl.27, Strain jl.68, and Strain jl.77.

FIG. 18F shows the CFU of *S. aureus* and the expression of GMK and agr in culture with supernatant from Strain jl.68.

FIG. 19A shows the expression of GMK after the addition of supernatant. FIG. 19B shows the expression of agr after the addition of supernatant.

DETAILED DESCRIPTION OF THE INVENTION

Figure 1:
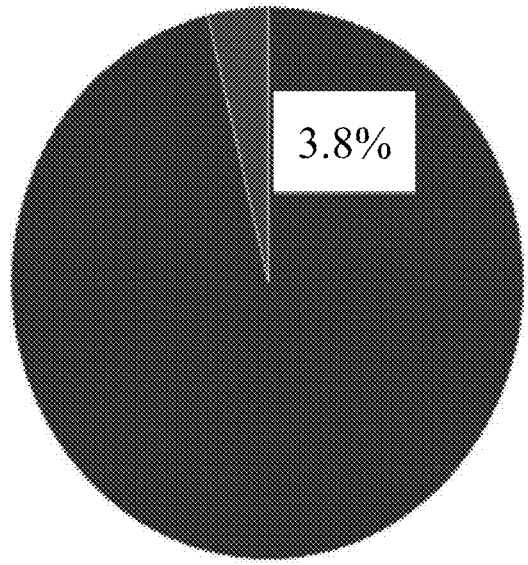
FIG. 1, is a pie chart that summaries the number of strain combinations tested that inhibited different *S. aureus* genes.
Figure 1:
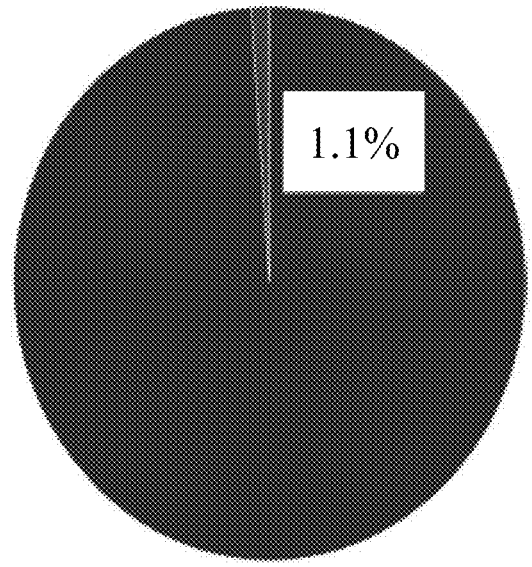

Provided herein are compositions, methods, kits and devices for the treatment of skin diseases. Furthermore, provided herein are (1) mixtures of bacteria (2) excipients, dosage forms and routes of administration for such mixtures, (3) and conditions for treatment with such bacterial mixtures.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included, unless the context clearly dictates otherwise.

The terminology used herein is for the purpose of describing particular instances only and is not intended to be limiting of any embodiment. As used herein, the singular forms "a," "an" and "the" are intended to include the plural forms as well, unless the context clearly indicates otherwise. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The term "subject" as used herein includes human and non-human mammals, including for example: a primate, cow, horse, pig, sheep, goat, dog, cat, or rodent, capable of being colonized by other organisms.

In some embodiments, provided herein are compositions which include bacteria having a percent identity based on 16S rRNA bacterial genetic sequence, a hypervariable region of the 16S rRNA, or whole genome comparison to a reference strain. Typically, comparison of the 16S rRNA bacterial genetic sequence allows a strain to be identified as within the same species as another strain by comparing sequences with known bacterial DNA sequences using NCBI BLAST search. The level of identity in relation to a nucleotide sequence may be determined for at least 20 contiguous nucleotides, for at least 30 contiguous nucleotides, for at least at least 40 contiguous nucleotides, for at least 50 contiguous nucleotides, for at least 60 contiguous nucleotides, for at least 100 contiguous nucleotides, for at least 200 contiguous nucleotides, for at least 300 contiguous nucleotides, for at least 400 contiguous nucleotides, for at least 500 contiguous nucleotides, for at least 600 contiguous nucleotides, for at least 700 contiguous nucleotides, for at least 800 contiguous nucleotides, for at least 900 contiguous nucleotides, for at least 1000 contiguous nucleotides, for at least 1100 contiguous nucleotides, for at least 1200 contiguous nucleotides, for at least 1300 contiguous nucleotides, for at least 1400 contiguous nucleotides, or for at least 1500 contiguous nucleotides. In some embodiments, the level of identity in relation to a nucleotide sequence is determined for the entire sequence searched. Percent identity may be at least 70%, 80%, 85%, 90%, 91%, 92%, 93%, 94%, 95%, 96%, 97%, 98%, 99%, or 100% to a reference bacterial 16S rRNA sequence, 16S rRNA V4 region sequence, or whole genome sequence. Percent identity may be at least 70%, 80%, 85%, 90%, 91%, 92%, 93%, 94%, 95%, 96%, 97%, 98%, 99%, or 100% to a reference bacteria 16S rRNA: V1 region, V2 region, V3 region, V5 region, V6 region, V7 region, V8 region or V9 region sequence. Percent identity may be at least 70%, 80%, 85%, 90%, 91%, 92%, 93%, 94%, 95%, 96%, 97%, 98%, 99%, or 100% to a reference bacterial sequence.

As used herein, a substance is "pure" or "substantially pure" if it is substantially free of other components of the sample source from which the substance is obtained. The terms "purify," "purifying" and "purified", when applied to a bacterium or bacteria, can refer to a bacterium that has been separated from at least some of the components with which it was associated either when initially produced or generated, or during any time after its initial production. A bacterium or a bacterial population may be considered purified if it is isolated at or after production, such as from a material or environment containing the bacterium or bacterial population, or by passage through culture. A purified bacterium or bacterial population may contain other materials up to at least about 10%, about 20%, about 30%, about 40%, about 50%, about 60%, about 70%, about 80%, about 90%, or above about 90% and still be considered purified. A purified bacterium or bacterial population may contain a single type of strain present in at least about 5, 10, 15, 20, 25, 30, 35, 40, 45, 50% or more of the bacteria present in a composition and still be considered purified.

Bacterial Mixtures

The skin of a human provides many environments for the microbiome. In healthy individuals, both the microbiome of the skin and the host environment of the skin are important for maintaining skin health. However, dysbiosis of the skin microbiome and replacement of commensal bacterial species with pathogenic bacterial species can cause disease. To this end, perturbation of a damaged skin microbiome with bacterial isolates from healthy individuals can restore function and diversity of a skin microbiome. For example, restoration and/or modification of a damaged microbiome can be used to treat a disease. Compositions described herein are used for treatment of a damaged skin microbiome and contain bacterial species that are purified. In some embodiments, the bacterial species comprise at least one, two, or three of the following bacterial species: *Bacillus velezensis, Bacillus wiedmannii, Lysinibacillus macrolides, Bacillus amyloliquefaciens, Staphylococcus caprae,* and *Bacillus tropicus.* In some embodiments, a composition comprises at least one, two, or three of the following bacterial species: *Bacillus cereus, Staphylococcus epidermidis, Bacillus nakamurai, Bacillus vallismortis, Lysinibacillus boronitolerans, Bacillus paranthracis, Bacillus thuringiensis, Psychrobacillus* sp. INOPO1, *Lysinibacillus* sp. FN11, *Bacillus* sp. Lzh-5, or *Staphylococcus capitis.* The bacterial species are lyophilized and/or formulated for delivery to the skin. A composition can be formulated as a suspension, an emulsion, a cream, a lotion, a tincture, a gel, a foam, a powder, an ointment, a paste, or an oil. Administration of the bacterial species are used to treat inflammation of the skin, a skin disorder, such as atopic dermatitis, or a symptom associated with inflammation of the skin or a skin disorder.

Additionally, compositions described herein are used for treatment of a damaged skin microbiome and contain bacterial strains that are purified. In some embodiments, the bacterial strains comprise at least one, two, or three of the following bacterial strains: Strain jl.121, Strain jl.21, Strain jl. 27, Strain jl.68, Strain jl.83, or Strain jl.77. The bacterial strains are lyophilized and/or formulated for delivery to the skin. A composition can be formulated as a suspension, an emulsion, a cream, a lotion, a tincture, a gel, a foam, a powder, an ointment, a paste, or an oil. Administration of the bacterial strains are used to treat inflammation of the skin, a skin disorder, such as atopic dermatitis, or a symptom associated with inflammation of the skin or a skin disorder Bacteria described herein and mixtures of the bacteria described herein are used to treat or inhibit, reduce, and/or eliminate pathogenic bacteria from colonizing or inducing inflammation of the skin. Bacteria described herein and mixtures of the bacteria described herein are used to suppress the growth of pathogenic bacteria. Bacteria described herein are used to modulate the expression of a gene in a pathogenic microorganism. Bacteria described herein are used to modulate the expression of a protein in a pathogenic microorganism. Bacteria described herein are isolated from the skin of a healthy individual. In some embodiments, bacteria described herein are purified. For example, a bacterial isolate described herein can be purified by one or more passages on an agar medium. In some cases, a healthy individual is a subject without one or more diseases of the skin. In some cases, bacteria are isolated from the epidermis of the skin. In some cases, bacteria are isolated from the skin of a foot, a leg, an arm, a torso, a hand, a groin, an armpit, a back, a neck, a head, an ear, a nose, a face or any region of the body covered in skin. In some embodiments, bacteria described herein are in a composition. In some embodiments, bacteria described herein are administered to treat a disease. In some cases, compositions described herein are lyophilized. In some cases, compositions described herein are formulated for delivery to a skin.

In some embodiments, a composition comprises live bacteria. In some cases, a live bacterium comprises a bacterium that retains membrane stability. In some cases, a live bacterium comprises a bacterium that is capable of transcription and translation. In some cases, a live bacterium comprises a bacterium that is capable of cell division. In some cases, live bacteria are determined by a culture dependent or a culture independent technique. In some cases, live bacteria comprise an individual or a group of bacteria that can produce a colony-forming unit (cfu) when plated on stable growth media. In some embodiments, live and/or dead bacteria are determined by imaging, for example with a live/dead stain. In some cases, a viability PCR based method can be used to determine live bacteria. In some cases, a metabolomic assay is used to determine live bacteria.

In some embodiments, bacteria described herein are grown in aerobic conditions. In some cases, bacteria described herein are grown in anaerobic conditions. In some cases, bacteria described herein can be an obligate aerobe, an obligate anaerobe, a facultative anaerobe, a microaerophile, or an aerotolerant organism and can be grown in any condition applicable for growth, (e.g., 0-40% O2, and/or 0-40% CO2). Bacteria described herein are grown at room temperature or in an incubator. For example, bacteria described herein can be grown in any temperature conducive for growth. In some instances, bacteria described herein are grown at about 1° C. to 50° C. In some instances, bacteria described herein are grown at 30° C. In some instances, bacteria described herein are grown at 37° C. Bacteria described herein are grown in liquid culture or on a solid media, such as agar supplemented with nutrients. In some cases, bacteria are grown in a medium with or without animal products. In some cases, bacteria are grown in a medium without animal products. In some instances, bacteria are grown in Tryptic Soy Broth (TSB).

In some cases, bacteria and/or a composition described herein are stored in a container. In some cases, a container is glass, plastic, metal, or any solid material. In some cases, a container is comprised in a kit. In some instances, when a sealed container containing bacteria or a composition described herein is placed at about: −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., or 38° C., the bacteria can retain greater than about: 0.1%, 1%, 10%, 20%, 30%, 40%, 50%, 60%, 70%, 80%, 90% or 99% culture viability after 3 months, 6 months, or 12 months, as measured by cfu counts. In some instances, when a sealed container containing bacteria or a composition described herein is placed at about: −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., or 38° C., the bacteria can retain greater than about: about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, about $10^{12}$ cfu after 3 months, 6 months, or 12 months, as measured by cfu counts. In some cases, the compositions disclosed herein are stable in a freezer (e.g., −80° C. to about −20° C.), a refrigerator (e.g. 4° C.), or at room temperature.

In some embodiments, provided herein are compositions of bacterial species. In some cases, a composition described herein comprises one or more bacterial species. For example, a composition described herein comprises 2, 3, 4, 5, 6, 7, 8, 9, 10 or more bacterial species. In some cases, a composition described herein comprises one bacterial species. In some cases, a composition described herein comprises two bacterial species. In some cases, a composition described herein comprises three bacterial species. In some cases, a composition described herein comprises four bacterial species. Provided herein are mixtures of bacteria comprising one or more a bacterial species of Table 1. In some embodiments, a composition described herein comprises 1, 2, 3, 4, 5, 6, 7, 8, 9, 10 or more bacterial species in Table 1.

TABLE 1

| Bacterial Species |
| --- |
| Species name |
| *Staphylococcus capitis* |
| *Staphylococcus caprae* |
| *Staphylococcus cohnii* |
| *Staphylococcus epidermidis* |
| *Staphylococcus intermedius* |
| *Staphylococcus lugdunensis* |
| *Staphylococcus pasteuri* |
| *Staphylococcus saprophyticus* |
| *Staphylococcus warneri* |
| *Bacillus velezensis* |
| *Bacillus amyloliquefaciens* |
| *Bacillus cecembensis* |
| *Bacillus cereus* |
| *Bacillus* sp. Lzh-5 |
| *Bacillus* sp. KbaL1 |
| *Bacillus* sp. SJ-10 |
| *Bacillus mediterraneensis* |
| *Bacillus mycoides* |
| *Bacillus nakamurai* |
| *Bacillus thuringiensis* |
| *Bacillus tropicus* |

TABLE 1-continued

Bacterial Species

Species name

Bacillus paranthracis
Bacillus vallismortis
Micrococcus aloeverae
Psychrobacillus sp. INOP01
Paenibacillus lentimorbus
Paenibacillus elgii
Bacillus wiedmannii
Brevibacillus parabrevis
Dermacoccus nishinomiyaensis
Kocuria marina
Lysinibacillus boronitolerans
Lysinibacillus macroides
Lysinibacillus sp. FN11
Lysinibacillus sp. UBA5994
Lysinibacillus sp. PB300
Lysinibacillus sp. YS11
Lysinibacillus boronitolerans
Lysinibacillus fusiformis
Macrococcus goetzii In some cases, a composition described herein comprises one or more bacterial strains. For example, a composition described herein comprises 2, 3, 4, 5, 6, 7, 8, 9, 10 or more bacterial strains. In some cases, a composition described herein comprises one bacterial strain. In some cases, a composition described herein comprises two bacterial strains. In some cases, a composition described herein comprises three bacterial strains. In some cases, a composition described herein comprises four bacterial strains. Provided herein are mixtures of bacteria comprising a one or more bacterial strains of Table 2. In some embodiments, a composition described herein comprises 1, 2, 3, 4, 5, 6, 7, 8, 9, 10 or more bacterial strains in Table 2.

TABLE 2

Bacterial Strains

| Strain Number | Strain Name |
| --- | --- |
| Strain 1 | Strain jl.19 |
| Strain 2 | Strain jl.39 |
| Strain 3 | Strain jl.121 |
| Strain 4 | Strain jl.21 |
| Strain 5 | Strain jl.26 |
| Strain 6 | Strain jl.27 |
| Strain 7 | Bacillus mediterraneensis jl.44 |
| Strain 8 | Strain jl.68 |
| Strain 9 | Strain jl.83 |
| Strain 10 | Strain jl.116 |
| Strain 11 | Strain jl.119 |
| Strain 12 | Strain jl.45 |
| Strain 13 | Strain jl.77 |

In some cases, a bacterial strain comprises Strain jl.83, Strain jl.27, Strain jl.77, Strain jl.68, Strain jl.121, or Strain jl.21. In some instances, the bacterial strains herein are identified by a 16s rRNA sequence. In some cases, Strain jl.83 comprises the 16s rRNA sequence of SEQ ID NO: 4. In some cases, Strain jl.83 comprises a 16s rRNA sequence with at least: 95%, 96%, 97%, 98%, or 99% sequence identity to SEQ ID NO: 4. In some cases, Strain jl.27 comprises the 16s rRNA sequence of SEQ ID NO: 1. In some cases, Strain jl.27 comprises a 16s rRNA sequence with at least: 95%, 96%, 97%, 98%, or 99% sequence identity to SEQ ID NO: 1. In some cases, Strain jl.77 comprises the 16s rRNA sequence of SEQ ID NO: 2. In some cases, Strain jl.77 comprises a 16s rRNA sequence with at least: 95, 96%, 97%, 98%, or 99% sequence identity to SEQ ID NO: 2. In some cases, Strain jl.68 comprises the 16s rRNA sequence of SEQ ID NO: 5. In some cases, Strain jl.68 comprises a 16s rRNA sequence with at least: 95%, 96%, 97% 98%, or 99% sequence identity to SEQ ID NO: 5. In some cases, Strain jl.121 comprises the 16s rRNA sequence of SEQ ID NO: 6. In some cases, Strain jl.121 comprises a 16s rRNA sequence with at least: 959, 96%, 97%, 98%, or 99% sequence identity to SEQ ID NO: 6. In some cases, Strain jl.21 comprises the 16s rRNA sequence of SEQ ID NO: 3. In some cases, Strain jl.21 comprises a 16s rRNA sequence with at least: 95%, 96%, 97%, 98%, or 99% sequence identity to SEQ ID NO: 3.

In some cases, a bacterial strain comprises Strain jl.19, Strain jl.39, Strain jl.26, Strain jl.116, Strain jl.119, or Strain jl.45. In some cases, Strain jl.19 comprises the 16s rRNA sequence of SEQ ID NO: 16. In some cases, Strain jl.19 comprises a 16s rRNA sequence with at least: 95%, 96%, 97%, 98%, or 99% sequence identity to SEQ ID NO: 16. In some cases, Strain jl.39 comprises the 16s rRNA sequence of SEQ ID NO: 17. In some cases, Strain jl.39 comprises a 16s rRNA sequence with at least: 95%, 96%, 97%, 98%, or 99% sequence identity to SEQ ID NO: 17. In some cases, Strain jl.26 comprises the 16s rRNA sequence of SEQ ID NO: 18. In some cases, Strain jl.26 comprises a 16s rRNA sequence with at least: 95%, 96%, 97%, 98%, or 99% sequence identity to SEQ ID NO: 18. In some cases, Strain jl.116 comprises the 16s rRNA sequence of SEQ ID NO: 19. In some cases, Strain jl.116 comprises a 16s rRNA sequence with at least: 95%, 96%, 97%, 98%, or 99% sequence identity to SEQ ID NO: 19. In some cases, Strain jl.119 comprises the 16s rRNA sequence of SEQ ID NO: 20. In some cases, Strain jl.119 comprises a 16s rRNA sequence with at least: 95%, 96%, 97%, 98%, or 99% sequence identity to SEQ ID NO: 20. In some cases, Strain jl.45 comprises the 16s rRNA sequence of SEQ ID NO: 21. In some cases, Strain jl.45 comprises a 16s rRNA sequence with at least: 95%, 96%, 97%, 98%, or 99% sequence identity to SEQ ID NO: 21. In some cases, a bacterial strain herein comprises a 16s rRNA sequence with at least: 95%, 96%, 97%, 98%, or 99% sequence identity over at least 500 bases, 600 bases, 700 bases, 800 bases, 900 bases, 1000 bases, or 1100 bases to any one of SEQ ID NOS: 1-6 or 16-21. In some cases, a bacterial strain herein comprises a 16s rRNA sequence with 100% sequence identity over at least 500 bases, 600 bases, 700 bases, 800 bases, 900 bases, 1000 bases, or 1100 bases to any one of SEQ ID NOS: 1-6 or 16-21.

In some instances, the bacterial strains herein are identified by an identifier sequence. For example, an identifier sequence is a sequence found in the genome and/or accessory genome such as a plasmid that is used to identify a bacterial strain. In some cases, Strain jl.83 comprises the identifier sequence of SEQ ID NO: 11, SEQ ID NO: 12, or both. In some cases, Strain jl.83 comprises an identifier sequence with at least: 90%, 91%, 92%, 93%, 94%, 95%, 96%, 97%, 98%, or 99% sequence identity to SEQ ID NO: 11. In some cases, Strain jl.83 comprises an identifier sequence with at least: 90%, 91%, 92%, 93%, 94%, 95%, 96%, 97%, 98%, or 99% sequence identity to SEQ ID NO: 12. In some cases, Strain jl.27 comprises the identifier sequence of SEQ ID NO: 15. In some cases, Strain jl.27 comprises an identifier sequence with at least: 90%, 91%, 92%, 93%, 94%, 95%, 96%, 97%, 98%, or 99% sequence identity to SEQ ID NO: 15. In some cases, Strain jl.77 comprises the identifier sequence of SEQ ID NO: 7, SEQ ID NO: 8, or both. In some cases, Strain jl.77 comprises an identifier sequence with at least: 90%, 91%, 92%, 93%, 94%, 95%, 96%, 97%, 98%, or 99% sequence identity to SEQ ID NO: 7. In some cases, Strain jl.77 comprises an identifier sequence with at least: 90%, 91%, 92%, 93%, 94%, 95%, 96%, 97%, 98%, or 99% sequence identity to SEQ ID NO: 8. In some cases, Strain jl.68 comprises the identifier sequence of SEQ ID NO: 13. In some cases, Strain jl.68 comprises an identifier sequence with at least: 90%, 91%, 92%, 93%, 94%, 95%, 96%, 97%, 98%, or 99% sequence identity to SEQ ID NO: 13. In some cases, Strain jl.121 comprises the identifier sequence of SEQ ID NO: 14. In some cases, Strain jl.121 comprises an identifier sequence with at least: 90%, 91%, 92%, 93%, 94%, 95%, 96%, 97%, 98%, or 99% sequence identity to SEQ ID NO: 14. In some cases, Strain jl.21 comprises the identifier sequence of SEQ ID NO: 9, SEQ ID NO: 10, or both. In some cases, Strain jl.21 comprises an identifier sequence with at least: 90%, 91%, 92%, 93%, 94%, 95%, 96%, 97%, 98%, or 99% sequence identity to SEQ ID NO: 9. In some cases, Strain jl.21 comprises an identifier sequence with at least: 90%, 91%, 92%, 93%, 94%, 95%, 96%, 97%, 98%, or 99% sequence identity to SEQ ID NO: 10. In some cases, a bacterial strain herein comprises an identifier sequence with at least: 95%, 96%, 97%, 98%, or 99% sequence identity over at least 500 bases, 600 bases, 700 bases, 800 bases, 900 bases, 1000 bases, 1100 bases, or 1200 bases to any one of SEQ ID NOS: 7-15. In some cases, a bacterial strain herein comprises an identifier sequence with 100% sequence identity over at least 500 bases, 600 bases, 700 bases, 800 bases, 900 bases, 1000 bases, 1100 bases or 1200 bases to any one of SEQ ID NOS: 7-15.

In some embodiments, provided herein are bacteria comprising a sequence of SEQ ID NO: 11, SEQ ID NO: 12, or both. In some cases, provided herein are bacteria comprising a sequence with at least: 90%, 91%, 92%, 93%, 94%, 95%, 96%, 97%, 98%, or 99% sequence identity to SEQ ID NO: 11. In some cases, provided herein are bacteria comprising a sequence with at least: 90%, 91%, 92%, 93%, 94%, 95%, 96%, 97%, 98%, or 99% sequence identity to SEQ ID NO: 12. In some cases, provided herein are bacteria comprising a sequence of SEQ ID NO: 15. In some cases, provided herein are bacteria comprising a sequence with at least: 90%, 91%, 92%, 93%, 94%, 95%, 96%, 97%, 98%, or 99% sequence identity to SEQ ID NO: 15. In some cases, provided herein are bacteria comprising a sequence of SEQ ID NO: 7, SEQ ID NO: 8, or both. In some cases, provided herein are bacteria comprising a sequence with at least: 90%, 91%, 92%, 93%, 94%, 95%, 96%, 97%, 98%, or 99% sequence identity to SEQ ID NO: 7. In some cases, provided herein are bacteria comprising a sequence with at least: 90%, 91%, 92%, 93%, 94%, 95%, 96%, 97%, 98%, or 99% sequence identity to SEQ ID NO: 8. In some cases, provided herein are bacteria comprising a sequence of SEQ ID NO: 13. In some cases, provided herein are bacteria comprising a sequence with at least: 90%, 91%, 92%, 93%, 94%, 95%, 96%, 97%, 98%, or 99% sequence identity to SEQ ID NO: 13. In some cases, provided herein are bacteria comprising a sequence of SEQ ID NO: 14. In some cases, provided herein are bacteria comprising a sequence with at least: 90%, 91%, 92%, 93%, 94%, 95%, 96%, 97%, 98%, or 99% sequence identity to SEQ ID NO: 14. In some cases provided herein are bacteria comprising a sequence of SEQ ID NO: 9, SEQ ID NO: 10, or both. In some cases, provided herein are bacteria comprising a sequence with at least: 90%, 91%, 92%, 93%, 94%, 95%, 96%, 97%, 98%, or 99% sequence identity to SEQ ID NO: 9. In some cases, provided herein are bacteria comprising a sequence with at least: 90%, 91%, 92%, 93%, 94%, 95%, 96%, 97%, 98%, or 99% sequence identity to SEQ ID NO: 10.

In some embodiments, a composition herein can comprise cell free components, such as supernatant from any one of the strains listed in Table 2. In some cases, a composition herein can comprise cell free components, from any combination of strains listed in Table 2. In some cases, a composition herein can comprise cell free components from one or more bacterial strains with at least 95%, 96%, 97%, 98%, or 99% sequence identity to any one of SEQ ID NOS: 1-6 or 16-21. In some cases, a composition herein can comprise cell free components from one or more bacterial strains comprising any one of SEQ ID NOS: 1-6 or 16-21. In some cases, a composition herein can comprise cell free components from a bacterial strain with at least 95%, 96%, 97%, 98%, or 99% sequence identity to SEQ ID NO: 5. In some cases, a composition herein can comprise cell free components from a bacterial strain comprising SEQ ID NO: 5.

In some cases, a composition described herein comprises one or more bacterial strains and one or more bacterial species. For example, a composition described herein comprises two bacterial species and one bacterial strain.

In some embodiments, a composition comprises two or more bacterial species or strains. In some embodiments, a composition comprises at least two of the following bacterial species: *Staphylococcus cohnii, Staphylococcus capitis, Staphylococcus caprae, Bacillus tropicus, Bacillus mycoides, Bacillus wiedmannii, Bacillus mediterraneensis, Bacillus amyloliquefaciens, Bacillus velezensis, Bacillus cereus, Bacillus cecembensis, Kocuria marina,* and *Lysinibacillus macroides*. In some embodiments, a composition comprises at least two of the following bacterial species: *Bacillus cereus, Staphylococcus epidermidis, Bacillus nakamurai, Bacillus vallismortis, Lysinibacillus boronitolerans, Bacillus paranthracis, Bacillus thuringiensis, Psychrobacillus* sp. INOPO1, *Lysinibacillus* sp. FNI1, *Bacillus* sp. Lzh-5, or *Staphylococcus capitis*. In some embodiments, a composition comprises at least two of the following bacterial species: *Bacillus velezensis, Bacillus wiedmannii, Lysinibacillus macrolides, Bacillus amyloliquefaciens, Staphylococcus caprae,* and *Bacillus tropicus*. In some embodiments, a composition comprises at least two of the following bacterial strains: Strain jl.83, Strain jl.27, Strain jl.77, Strain jl.68, Strain jl.121, and Strain jl.21. In some cases, a composition comprises bacterial strains Strain jl.83, and Strain jl.27. In some cases, a composition comprises bacterial strains Strain jl.68, and Strain jl.27. In some cases, a composition comprises bacterial strains Strain jl.68, and Strain jl.21. In some cases, a composition comprises bacterial strains Strain jl.83, and Strain jl.77. In some cases, a composition comprises bacterial strains Strain jl.27 and Strain jl.121. In some cases, a composition comprises bacterial strains Strain jl.21 and Strain jl.121.

In some embodiments, a composition comprises three or more bacterial species or strains. In some embodiments, a composition comprises at least three of the following bacterial species: *Staphylococcus cohnii, Staphylococcus capitis, Staphylococcus caprae, Bacillus tropicus, Bacillus mycoides, Bacillus wiedmannii, Bacillus mediterraneensis, Bacillus amyloliquefaciens, Bacillus velezensis, Bacillus cereus, Bacillus cecembensis, Kocuria marina,* and *Lysinibacillus macroides*. In some embodiments, a composition comprises at least three of the following bacterial species: *Bacillus velezensis, Bacillus wiedmannii, Lysinibacillus macrolides, Bacillus amyloliquefaciens, Staphylococcus caprae,* and *Bacillus tropicus*. In some embodiments, a composition comprises at least three of the following bacterial strains: Strain jl.83, Strain jl.27, Strain jl.77, Strain jl.68, Strain jl.121, and Strain jl.21.

In some embodiments, a composition described herein comprises three bacterial species or strains. In some embodiments, a composition comprises a bacterial species *Bacillus velezensis*, *Bacillus wiedmannii*, and *Lysinibacillus macrolides*. In some cases, a composition comprises bacterial strains Strain jl.83, Strain jl.27, and Strain jl.77. In some embodiments, a composition comprises a bacterial species *Bacillus amyloliquefaciens*, *Bacillus wiedmannii*, and *Staphylococcus caprae*. In some cases, a composition comprises bacterial strains Strain jl.68, Strain jl.27, and Strain jl.121. In some embodiments, a composition comprises a bacterial species *Bacillus amyloliquefaciens*, *Bacillus tropicus*, and *Staphylococcus caprae*. In some cases, a composition comprises bacterial strains Strain jl.68, Strain jl.21, and Strain jl.121. In some embodiments, a composition comprises a bacterial species combination from Table 3. In some embodiments, a composition is a bacterial species combination from Table 3. In some embodiments, a composition comprises a bacterial strain combination from Table 4. In some embodiments, a composition is a bacterial strain combination from Table 4.

TABLE 3

Three bacterial species combinations

| Combination Number | Bacterial species names |
| --- | --- |
| Combination 1 | *Bacillus amyloliquefaciens* |
| | *Staphylococcus cohnii* |
| | *Bacillus cereus* |
| Combination 2 | *Bacillus amyloliquefaciens* |
| | *Bacillus tropicus* |
| | *Staphylococcus caprae* |
| Combination 3 | *Bacillus amyloliquefaciens* |
| | *Bacillus wiedmannii* |
| | *Bacillus cecembensis* |
| Combination 4 | *Bacillus velezensis* |
| | *Bacillus mycoides* |
| | *Kocuria marina* |
| Combination 5 | *Bacillus velezensis* |
| | *Bacillus mycoides* |
| | *Lysinibacillus macroides* |
| Combination 6 | *Bacillus velezensis* |
| | *Bacillus wiedmannii* |
| | *Bacillus mediterraneensis* |
| Combination 7 | *Bacillus amyloliquefaciens* |
| | *Bacillus wiedmannii* |
| | *Staphylococcus caprae* |
| Combination 8 | *Bacillus amyloliquefaciens* |
| | *Staphylococcus capitis* |
| | *Bacillus cecembensis* |
| Combination 9 | *Bacillus velezensis* |
| | *Staphylococcus capitis* |
| | *Bacillus mediterraneensis* |
| Combination 10 | *Bacillus amyloliquefaciens* |
| | *Staphylococcus capitis* |
| | *Staphylococcus caprae* |
| Combination 11 | *Bacillus velezensis* |
| | *Bacillus wiedmannii* |
| | *Lysinibacillus macroides* |

TABLE 4

Three bacterial strain combinations

| Combination Number | Bacterial strain names |
| --- | --- |
| Combination 1 | Strain jl.68 |
| | Strain jl.19 |
| | Strain jl.116 |
| Combination 2 | Strain jl.68 |
| | Strain jl.21 |
| | Strain jl.121 |
| Combination 3 | Strain jl.68 |
| | Strain jl.27 |
| | Strain jl.119 |
| Combination 4 | Strain jl.83 |
| | Strain jl.26 |
| | Strain jl.45 |
| Combination 5 | Strain jl.83 |
| | Strain jl.26 |
| | Strain jl.77 |
| Combination 6 | Strain jl.83 |
| | Strain jl.27 |
| | *Bacillus mediterraneensis* jl.44 |
| Combination 7 | Strain jl.68 |
| | Strain jl.27 |
| | Strain jl.121 |
| Combination 8 | Strain jl.68 |
| | Strain jl.39 |
| | Strain jl.119 |
| Combination 9 | Strain jl.83 |
| | Strain jl.39 |
| | *Bacillus mediterraneensis* jl.44 |
| Combination 10 | Strain jl.68 |
| | Strain jl.39 |
| | Strain jl.121 |
| Combination 11 | Strain jl.83 |
| | Strain jl.27 |
| | Strain jl.77 |

In some embodiments, a composition described herein comprises one bacterial species or strain. In some embodiments, a composition comprises a second bacterial species or strain. In some embodiments, a composition comprises *Bacillus velezensis*. In some cases, a composition comprises Strain jl.83. In some embodiments, a composition comprises *Bacillus wiedmannii*. In some cases, a composition comprises Strain jl.27. In some embodiments, a composition comprises *Lysinibacillus macroides*. In some cases, a composition comprises Strain jl.77. In some embodiments, a composition comprises *Bacillus tropicus*. In some cases, a composition comprises Strain jl.21. In some embodiments, a composition comprises *Bacillus amyloliquefaciens*. In some cases, a composition comprises Strain jl.68. In some embodiments, a composition comprises *Staphylococcus caprae*. In some cases, a composition comprises Strain jl.121. In some embodiments, a composition comprises *Staphylococcus cohnii*. In some cases, a composition comprises Strain jl. 19. In some embodiments, a composition comprises *Staphylococcus capitis*. In some cases, a composition comprises Strain jl.39. In some embodiments, a composition comprises *Bacillus mycoides*. In some cases, a composition comprises Strain jl.26. In some embodiments, a composition comprises *Bacillus mediterraneensis*. In some cases, a composition comprises *Bacillus mediterraneensis* jl.44. In some embodiments, a composition comprises *Bacillus cereus*. In some cases, a composition comprises Strain jl.116. In some embodiments, a composition comprises *Bacillus cecembensis*. In some cases, a composition comprises Strain jl.119. In some embodiments, a composition comprises *Kocuria marina*. In some cases, a composition comprises Strain jl.45.

In some embodiments, *Bacillus velezensis* is *Bacillus velezensis* DSM 23117, which can be obtained from the DSMZ-German Collection of Microorganisms and Cell Cultures depository. In some embodiments, *Bacillus wiedmannii* is *Bacillus wiedmannii* DSM 102050, which can be obtained from the DSMZ-German Collection of Microorganisms and Cell Cultures depository. In some embodiments, *Lysinibacillus macroides* is *Lysinibacillus macroides* DSM 54, which can be obtained from the DSMZ-German Collection of Microorganisms and Cell Cultures depository. In some embodiments, *Bacillus amyloliquefaciens* is *Bacillus amyloliquefaciens* DSM 7, which can be obtained from the DSMZ-German Collection of Microorganisms and Cell Cultures depository. In some embodiments, *Staphylococcus caprae* is *Staphylococcus caprae* DSM 20608, which can be obtained from the DSMZ-German Collection of Microorganisms and Cell Cultures depository. In some embodiments, *Bacillus amyloliquefaciens* is *Bacillus amyloliquefaciens* ATCC 23350 (*Bacillus amyloliquefaciens* F IFO 15535) which can be obtained from the ATCC (American Type Culture Collection) depository. In some embodiments, *Bacillus tropicus* is *Bacillus tropicus* ATCC 4342 (*Bacillus tropicus* NRS 731), which can be obtained from the ATCC (American Type Culture Collection) depository.

In some embodiments, when administered to a subject, a bacterial species or a strain described herein can reduce or eliminate colonization of the skin of pathogenic: bacteria, fungi or viruses. In some cases, a composition described herein is used to kill a pathogenic bacteria, fungi or virus. In some cases, a composition described herein is used to suppress growth of a pathogenic bacteria, fungi or virus. In some cases, a composition described herein is used to control growth of a pathogenic bacteria, fungi or virus. In some cases, a composition described herein is used to control virulence of a pathogenic bacteria, fungi or virus. In some cases, a composition comprising one or more bacterial species or strains when administered can reduce or eliminate colonization of the skin of pathogenic: bacteria, fungi or viruses. Skin pathogenic bacteria include, without limitation, *Staphylococcus* sp., *Micrococcus* sp., *Corynebacterium* sp., *Staphylococcus aureus*, *Streptococcus pyogenes*, *Pseudomonas aeruginosa*, *Pasteurella multocida*, *Capnocytophaga canimorsus*, *Bartonella* sp., *Klebsiella rhinoscleromatis*, and *Vibrio vulnificus*. In some cases, a pathogenic bacteria comprises *Gardnerella vagina/is*. Pathogenic skin fungi include, without limitation, ascomycete dermatophytes, including the genera *Aspergillus, Trichophyton, Microsporum*, and *Epidermophyton*, and basidiomycete fungi in the genus *Malassezia*. In some cases, a skin pathogenic fungi comprises *Malassezia pachydermatis, Candida albicans, Microsporum canis*, and *Trichophyton mentagrophytes*. Exemplary skin pathogenic viruses include, without limitation, Herpes sp., Herpes zoster., Herpes simplex., Molluscum contagiosum, and Human papillomavirus. Such reduction of pathogenic bacteria, fungi or viruses may be in any location of the skin, for example the forearm, the leg, or the stomach of a subject. In some cases, a composition herein can reduce *S. aureus* toxin production, reduce fungal (e.g., *Candida*) hyphal formation, reduce *Malassezia* sebum metabolism, or reduce *Gardnerella* biofilm formation.

Provided herein are compositions comprising a bacterial species and/or a bacterial strain described herein in an amount sufficient for modulations of the expression of a gene in a pathogenic microorganism, or a modulation in the expression of a protein in a pathogenic microorganism. In some cases, the modulation is an increase of the gene expression or the protein expression. In some cases, the modulation is a decrease of the gene expression or the protein expression. In some cases, the composition provides for a reduction in the expression of a gene or protein from *S. aureus* or *S. pyogenes*. Exemplary genes for modulation and suppression include, without limitation, a virulence gene, a metabolism gene, a transcription gene, a translation gene, a protein processing gene, a protein folding gene, a secretion gene, a cell division gene, a biosynthesis gene, a cell wall gene, a cell membrane gene, an antibiotic resistance gene, and a protein coded by one of these genes. In some cases, the gene or protein is associated with growth, regulation (e.g., virulence regulation, metabolic regulation, or growth regulation), direct virulence such as a toxin, stress, or a metabolic state. In some cases, the gene is gmk, agr, psmA, sigB, saeR, and/or ccpA. In some cases, the protein is encoded by gmk, agr, psmA, sigB, saeR, and/or ccpA. In some cases, the expression of a gene is measured by a promoter-reporter strain. For example, a promoter of a gene of interest such as, gmk, agr, psmA, sigB, saeR, or ccpA can be fused to a fluorescent reporter such as GFP, or luciferase to measure the amount of gene expression. Exemplary genes for promoter-reporter *S. aureus* strains are shown in Table 5. In some cases, gene expression is used to assess constitutive metabolic function, quorum sensing, a toxin that damages host tissue, a stress response sigma factor, virulence regulation, and/or carbon catabolite repression. In some cases, gene expression is measured by a Northern blot, a Western blot, a promoter-reporter gene, a microarray, a PCR assay such as a reverse transcription polymerase chain reaction, a Serial Analysis ofGene Expression (SAGE), a next generation sequencing technique such as RNA Seq, or a combination of these methods. In some cases, the expression of a protein is measured. In some cases, protein expression is measured by a Western blot, an enzyme-linked immunoassay (ELISA), an SDS-PAGE gel, a Bicinchoninic acid (BCA) assay, or any assay that quantifies protein expression and/or amounts.

TABLE 5

Promoter-Reporter Stains

| Promoter | Protein Function | Associated with | Protein Genbank Reference for gene | Genome Genbank Reference |
|---|---|---|---|---|
| gmk | Constitutive metabolic function | Growth | WP_000368227.1 | GenBank: CP000253.1 Range: 1126551 to 1126850 |
| agr | Quorum sensing induction | Virulence (regulatory) | ADF28639.1 | GenBank ID: CP000253.1 Range: 2093636 to 2093876 |

TABLE 5-continued

Promoter-Reporter Stains

| Promoter | Protein Function | Associated with | Protein Genbank Reference for gene | Genome Genbank Reference |
| --- | --- | --- | --- | --- |
| psmA | Toxin that damages host tissue | Virulence (direct) | WP_014373781.1 | GenBank ID: CP000253.1 Range: 412992 to 413258 |
| sigB | Stress response sigma factor | Stress (regulatory) | CAC6986262.1 | GenBank ID: CP000253.1 Range: 2133482 to 2133781 |
| saeR | Broad virulence regulation | Virulence (regulatory) | WP_000149344.1 | GenBank ID: CP000253.1 Range: 700936 to 701683 |
| ccpA | Carbon catabolite repression | Metabolic state | WP_000219066.1 | GenBank ID: CP000253.1 Range: 1757336 to 1757835 |

In some embodiments, a composition comprising a bacterial species and/or a bacterial strain can further comprise one or more compounds. In some cases, a compound can be an environmental component. In some cases, a compound comprises a carbon source, a nitrogen source, a phosphorus source, a sulfur source, or a metal ion source. In some cases, a compound can produce a synergistic effect with a bacterial composition. For example, a compound can enhance the inhibition of S. aureus expression. In some cases, a compound increases the potency of a bacterial composition. In some cases, a compound comprises thiamine (vitamin B-1) or a salt thereof. In some cases, a compound comprises acetate, beta-alanine, bicarbonate, biotin, butyrate, caffeine, citrate, creatine, D-cellobiose, D-fructose, D-glucosamine, D-glucose, D-mannitol, D-raffinose, D-sorbitol, D-sucrose, D-trehalose, D-xylose, formate, GlcNAc, glycerol, glycine, L-alanine, L-arabinose, L-arginine, L-citrulline, L-glutamine, L-hydroxyproline, L-isoleucine, L-leucine, L-methionine, L-ornithine, L-proline, L-serine, L-taurine, L-threonine, L-valine, L-ascorbate, L-lactate, nicotinamine, polysorbate 20, polysorbate 80, propionate, pyruvate, succinate, thiamine, triethanolamine, or urea.

Routes of Administration, Excipients, Dosing, and Dosage Forms

In some embodiments, the terms "administer," "administering", "administration," and the like, as used herein, can refer to methods that can be used to enable delivery of compositions described herein, to the desired site of biological action. In some cases, delivery comprises topical administration. In some cases, delivery can include injection, inhalation, catheterization, gastrostomy tube administration, intravenous administration, intraosseous administration, ocular administration, otic administration, topical administration, transdermal administration, oral administration, rectal administration, nasal administration, intravaginal administration, intracavernous administration, intracerebral administration, transurethral administration, buccal administration, sublingual administration, or a combination thereof. Delivery can include direct application to the affect tissue or region of the body. Delivery can include a parenchymal injection, an intra-thecal injection, an intra-ventricular injection, or an intra-cisternal injection. A composition provided herein can be administered by any method. A method of administration can be by intraarterial injection, intracerebroventricular injection, intracisternal injection, intramuscular injection, intraorbital injection, intraparenchymal injection, intraperitoneal injection, intraspinal injection, intrathecal injection, intravenous injection, intraventricular injection, stereotactic injection, subcutaneous injection, epidural, or any combination thereof. Delivery comprises parenteral administration (e.g., intravenous, subcutaneous, intrathecal, intraperitoneal, intramuscular, intravascular or infusion administration). In some embodiments, delivery comprises a nanoparticle, a microparticle, a viral-like particle, a liposome, an exosome, an extracellular vesicle, a microneedle, an implant, or a combination thereof. In some cases, delivery is from a device. In some cases, delivery is by an enema, an eye drop, a nasal spray, a spray, an ear drop, or any combination thereof. In some cases, delivery is in the form of a solutions, a suspension, an emulsions, a tablet, a pill, a pellet, a capsule, a capsule including a liquid, a powder, a sustained-release formulation, a directed release formulation, lyophylates (freeze dried/lyophilized), an aerosols, a spray, a granules, a powder, or a syrup. In some cases, delivery comprises an inhaler, a diffuser, a nebulizer, or a combination thereof. Delivery can include topical administration (such as a lotion, a cream, a patch, a film, a gel, a spray, a drip, a liquid formulation, an ointment, a suspension, an emulsion, a tincture, a foam, a powder, a paste, or an oil) to an external surface of a surface, such as a skin. In some instances, a subject can administer the composition in the absence of supervision. In some instances, a subject can administer the composition under the supervision of a medical professional (e.g., a physician, nurse, physician's assistant, orderly, hospice worker, etc.). In some cases, a medical professional can administer the composition. In some cases, the subject can administer the composition.

To facilitate administration, pharmaceutical compositions described herein may include one or more pharmaceutically acceptable excipients. Example pharmaceutically acceptable excipients include, without limitation, diluents, adjuvants, excipients, water, oils (including petroleum, animal, vegetable, natural oils, or synthetic oils.). Further examples include saline, gum acacia, gelatin, starch paste, talc, keratin, colloidal silica, and urea. Such excipients may include binders such as ethyl cellulose, carboxymethylcellulose, microcrystalline cellulose, or gelatin; excipients such as starch, lactose or dextrins; disintegrating agents such as alginic acid, sodium alginate, Primogel, and cornstarch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of excipients include polyethylene glycol, cyclodextrin, oils, or any other similar liquid carrier that may be formulated into a capsule. Still further examples of excipients include sterile diluents such as water, saline solution, physiological saline, Ringer's solution, isotonic sodium chloride, phosphate-buffered saline, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents. In some embodiments of the invention, the pharmaceutically acceptable carrier comprises a growth medium that can support the growth and/or static existence of beneficial bacteria described herein in the context of the pharmaceutical composition prior to administration of the pharmaceutical composition to the subject.

In some embodiments, a composition described herein comprises a lyoprotectant. In some cases, a composition described herein comprises a cryoprotectant. In some embodiments, the composition can further comprise an emollient. In some cases, a composition described herein is freeze dried or lyophilized. In some cases, a lyoprotectant can comprise a milk, a sugar, sucrose, lactose, glucose, trehalose, glycerol, mannitol, sorbitol, glycine, alanine, lysine, polyethylene glycol, a dextran or polyvinylpyrrolidone (PVP).

Various other additives can be included in the compositions.

Non-limiting examples of additives include antioxidants, astringents, perfumes, preservatives, emollients, pigments, dyes, humectants, propellants, and sunscreen agents, as well as other classes of materials whose presence may be desirable pharmaceutically or otherwise. In some cases, an emollient can comprise a moisturizer.

Non-limiting examples of optional additives include preservatives, such as sorbate; solvents, such as isopropanol and propylene glycol; astringents, such as menthol and ethanol; emollients, such as polyalkylene methyl glucosides; humectants, such as glycerin; emulsifiers, such as glycerol stearate, PEG-100 stearate, polyglyceryl-3 hydroxyluryl ether, and polysorbate 60; sorbitol and other polyhydroxy alcohols, such as polyethylene glycol; sunscreen agents, such as methoxy octyl cinnamate (Parsol MCX) and butyl methoxy benzoylmethane (Parsol 1789); antioxidants, such as ascorbic acid (vitamin C), α-tocopherol (Vitamin E), β-tocopherol, γ-tocopherol, δ-tocopherol, ε-tocopherol, ζ1-tocopherol, ζ2-tocopherol, η-tocopherol, and retinol (vitamin THE); essential oils, ceramides, essential fatty acids, mineral oils, vegetable oils (eg soy oil, palm oil, shea butter liquid fraction, sunflower oil), animal oils (eg perhydrosqualene), synthetic oils, silicone oils or waxes (for example, cyclomethicone and dimethicone), fluorinated oil (usually perfluoropolyethers), fatty alcohols (for example, cetyl alcohol), and waxes (for example, beeswax, camauba wax and paraffin wax); modifiers of skin feel; and thickeners and structuring agents, such as swellable clays and cross-linked carboxypolialkylenes.

In some cases, a composition comprises a therapeutic agent. In some instances, a therapeutic agent is a drug or a compound. In some cases, a therapeutic agent can comprise a salt of a therapeutic agent. As used herein, a therapeutic agent, can also refer to the free-base, acid, salts, esters, and mixtures of a therapeutic agent. In some cases, a salt can comprise a pharmaceutically acceptable salt. In some cases, a salt comprises an HCl salt, an ascorbic acid salt, a mandelic acid salt, an aspartic acid salt, a carbonic acid salt, a citric acid salt, a formic acid salt, a glutamic acid salt, a lactic acid salt, a lauric acid salt, a maleic acid salt, a palmitic acid salt, or a phosphoric acid salt.

In some embodiments, administering comprises administering one or more additional therapeutics. In some cases, a second therapeutic is administered. In some instances, a second therapy is administered concurrently or consecutively with a first therapy. In some instances, a second therapy is administered in parallel with the first therapy. In some instances, a second therapy can enhance the efficacy of a first therapy. In some instances, a second therapy is comprised in a single dose with a first therapy. For example, an additional therapeutic can be added to a bacterial mixture described herein. In some instances, a second therapy may be comprised in a separate dose from the first therapy. In some cases, a second therapy comprises a cream, wet dressing, a light therapy (e.g., phototherapy), or behavior modification. In some cases, a second therapy comprises an antibody, such as a human monoclonal antibody. In some cases, a second therapy comprises an antibiotic. In some cases, a second therapy comprises a corticosteroid, a calcineurin inhibitor, pimecrolimus, tacrolimus, crisaborole, doxepin, narrowband ultraviolet B (NBUVB) phototherapy, ultraviolet A1 (UVA1) phototherapy, an antihistamine, diphenhydramine, hydroxyzine, cyproheptadine, fexofenadine, cetirizine, loratadine, cyclosporine, dupilumab, tralokinumab, nemolizumab, an anti-OX40 antibody, a JAK1/JAK2 inhibitor, a PDE4 inhibitor, upadacitinib, abrocitinib, azathioprine, an emollient, a moisturizer, an interleukin inhibitor, methotrexate, mycophenolate mofetil, or interferon gamma. In some cases, a second therapy comprises a ephalosporin (e.g., cefazolin, cephalothin and cephalexin), clindamycin, lincomycin, erythromycin, flucloxacillin, dicloxacillin, rifampicin, a lincosamide (e.g., clindamycin, lincomycin), cotrimoxazole, linezolid, quinupristin, dalfopristin, trimethoprim, sulfamethoxazole, fusidic acid, penicillin, methicillin, vancomycin, or a salt of any of these. In some instances, a second therapeutic or a first therapy can be administered buccally, enterally, by inhalation administration, by infusion administration, intramuscularly, intrathecally, intravenously, nasally, ophthalmically, orally, otically, by rectal administration, subcutaneously, sublingually, topically, transdermally or by any administration method.

Dosing may include single or multiple administrations of pharmaceutical compositions described herein. Examples include: multiple times a day, daily, every other day, 1, 2, 3, 5, 6, or 7 times a week, weekly, or less often, a single administration, a course of treatment involving several treatments on a regular or irregular basis, or multiple administrations for a period of time a disease or condition is treated. In some cases, dosing can occur every day, 2 days, 3 days, 4 days, 5 days, 6 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 1 year, 2 years, or as needed. The dosing regimen, including the regularity of and mode of administration, may be dependent on factors including but not limited to the subject being treated; the severity of the condition; the manner of administration, the stage of colonization, the amount of a pathogenic organism present, the presence of one or more other conditions such as pregnancy, infancy, or the presence of one or more additional diseases. In some cases, the subject is an infant. The infant can be up to 6 months old, up to 12 months old, or up to 24 months old. In some cases, the subject is a child. The child may be 2 years to 21 years old. In some cases, the child may be up to: 5, 7, 12, 18 or 21 years old. In some cases, the subject is an adult. Adults may be 21 years old or more. In some embodiments, the adult is of advanced age, such as 65 years or older.

Administration or application of a composition disclosed herein can be performed for a treatment duration of at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, at least 3 years, at least 4 years, at about 5 years, at least 6 years, at least 7 years, at least 8 years, at least 9 years, at least 10 years, at least 15 years, at least 20 years, or for life. Administration can be performed repeatedly over a lifetime of a subject, such as once a month or once a year for the lifetime of a subject. Administration can be performed repeatedly over a substantial portion of a subject's life, such as once a month or once a year for at least about 1 year, 5 years, 10 years, 15 years, 20 years, 25 years, 30 years, or more.

Compositions, including pharmaceutical compositions, described herein may comprise a single (unit) dose of bacteria. Compositions described herein may comprise about $10^2$ to about $10^{15}$ colony forming units (cfu) of bacteria, a bacterial species, or a bacterial strain described herein. Compositions described herein may comprise about: $10^2$ to $10^{12}$ cfu, $10^3$ to $10^{12}$ cfu, $10^3$ to $10^{11}$ cfu, $10^3$ to $10^{10}$ cfu, $10^3$ to $10^9$ cfu, $10^3$ to $10^8$ cfu, $10^3$ to $10^7$ cfu, $10^3$ to $10^6$ cfu, $10^3$ to about $10^5$ cfu, $10^3$ to $10^4$ cfu, $10^4$ to $10^{12}$ cfu, $10^4$ to $10^{11}$ cfu, $10^4$ to $10^{10}$ cfu, $10^4$ to $10^9$ cfu, $10^4$ to $10^8$ cfu, $10^4$ to $10^7$ cfu, $10^4$ to $10^6$ cfu, $10^5$ to $10^{12}$ cfu, $10^5$ to $10^{11}$ cfu, about $10^5$ to about $10^{10}$ cfu, $10^6$ to $10^{12}$ cfu, $10^7$ to $10^{12}$ cfu, $10^8$ to $10^{12}$ cfu, $10^9$ to $10^{12}$ cfu, $10^{10}$ to $10^{12}$ cfu, $10^{11}$ to $10^{12}$ cfu, or $10^6$ to $10^{10}$ cfu of bacteria, a bacterial species, or a bacterial strain described herein. In some embodiments, compositions comprise about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, about $10^{12}$ cfu, or about $10^{13}$ cfu of bacteria, a bacterial species, or a bacterial strain described herein.

Compositions, such as pharmaceutical compositions, described herein may comprise $10^2$ to $10^{15}$ colony forming units (cfu) of bacteria, a bacterial species, or a bacterial strain described herein per mL. Compositions described herein may comprise about $10^2$ to $10^{12}$ cfu, $10^3$ to $10^{12}$ cfu, $10^3$ to $10^{11}$ cfu, $10^3$ to $10^{10}$ cfu, $10^3$ to $10^9$ cfu, $10^3$ to $10^8$ cfu, $10^3$ to $10^7$ cfu, $10^3$ to $10^6$ cfu, $10^3$ to about $10^5$ cfu, $10^3$ to $10^4$ cfu, $10^4$ to $10^{12}$ cfu, $10^4$ to $10^{11}$ cfu, $10^4$ to $10^{10}$ cfu, $10^4$ to $10^9$ cfu, $10^4$ to $10^8$ cfu, $10^4$ to $10^7$ cfu, $10^4$ to $10^6$ cfu, $10^5$ to $10^{12}$ cfu, $10^5$ to $10^{11}$ cfu, $10^5$ to $10^{10}$ cfu, $10^6$ to $10^{12}$ cfu, $10^7$ to $10^{12}$ cfu, $10^8$ to $10^{12}$ cfu, $10^9$ to $10^{12}$ cfu, $10^{10}$ to $10^{12}$ cfu, $10^{11}$ to $10^{12}$ cfu, or $10^6$ to $10^{10}$ cfu of bacteria, a bacterial species, or a bacterial strain described herein per mL.

Compositions, such as pharmaceutical compositions, described herein may comprise $10^2$ to $10^{15}$ colony forming units (cfu) of bacteria, a bacterial species, or a bacterial strain described herein per gram. Compositions described herein may comprise about $10^2$ to $10^{12}$ cfu, $10^3$ to $10^{12}$ cfu, $10^3$ to $10^{11}$ cfu, $10^3$ to $10^{10}$ cfu, $10^3$ to $10^9$ cfu, $10^3$ to $10^8$ cfu, $10^3$ to $10^7$ cfu, $10^3$ to $10^6$ cfu, $10^3$ to about $10^5$ cfu, $10^3$ to $10^4$ cfu, $10^4$ to $10^{12}$ cfu, $10^4$ to $10^{11}$ cfu, $10^4$ to $10^{10}$ cfu, $10^4$ to $10^9$ cfu, $10^4$ to $10^8$ cfu, $10^4$ to $10^7$ cfu, $10^4$ to $10^6$ cfu, $10^5$ to $10^{12}$ cfu, $10^5$ to $10^{11}$ cfu, $10^5$ to $10^{10}$ cfu, $10^6$ to $10^{12}$ cfu, $10^7$ to $10^{12}$ cfu, $10^8$ to $10^{12}$ cfu, $10^9$ to $10^{12}$ cfu, $10^{10}$ to $10^{12}$ cfu, $10^{11}$ to $10^{12}$ cfu, or $10^6$ to $10^{10}$ cfu of bacteria, a bacterial species, or a bacterial strain described herein per gram.

Compositions described herein may comprise may at least about 0.01% by weight, at least about 0.05% by weight, at least about 0.1% by weight, at least about 0.2% by weight, at least about 0.3% by weight, at least about 0.4% by weight, at least about 0.5% by weight, at least about 0.6% by weight, at least about 0.7% by weight, at least about 0.8% by weight, at least about 0.9% by weight, at least about 1.0% by weight, at least about 1.5% by weight, at least about 2.0% by weight, at least about 3.0% by weight, at least about 4.0% by weight, at least about 5.0% by weight, at least about 6.0% by weight, at least about 7.0% by weight, at least about 8.0% by weight, at least about 9.0% by weight, at least about 10.0% by weight, at least about 11.0% by weight, at least about 12.0% by weight, at least about 13.0% by weight, at least about 14.0% by weight, at least about 15.0% by weight, at least about 16.0% by weight, at least about 17.0% by weight, at least about 18.0% by weight, at least about 19.0% by weight, at least about 20.0% by weight, at least about 25.0% by weight, at least about 30.0% by weight, at least about 35.0% by weight, at least about 40.0% by weight, at least about 45.0% by weight, or at least about 50.0% by weight of bacteria, a bacterial species, or a bacterial strain described herein. In some embodiments, compositions can include from 0.01% to 30% by weight, from about 0.01% to 20% by weight, from 0.01% to 5% by weight, from 0.1% to 30% by weight, from 0.1% to 20% by weight, from 0.1% to about 15% by weight, from 0.1% to 10% by weight, from 0.1% to 5% by weight, from 0.2% to 5% by weight, from 0.3% to 5% by weight, from 0.4% to 5% by weight, from 0.5% to 5% by weight, or from 1% to 5% by weight of bacteria, a bacterial species, or a bacterial strain described herein.

Compositions, including pharmaceutical compositions, described herein may comprise a ratio (cfu to cfu) of about: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900 or about 1:1000 of a species in Table 1 to another species in Table 1, a strain in Table 2 to another strain in Table 2, or a species in Table 1 to a strain in Table 2. Compositions, including pharmaceutical compositions, described herein may comprise a ratio (cfu to cfu) of about: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900 or about 1:1000 of multiple strains of *Bacillus velezensis, Bacillus wiedmannii, Lysinibacillus macrolides, Bacillus amyloliquefaciens, Staphylococcus caprae,* and/or *Bacillus tropicus.*

In some embodiments, a composition herein comprises a formulation. In some cases, a formulation comprises freeze dried or lyophilized bacteria. In some cases, a formulation comprises reconstituted bacteria. In some cases, an individual species or strain is stored in a container such as a vial. In some instances, a formulation herein comprises a mixture of bacteria from 2, 3, 4, 5, or more reconstituted vials.

Conditions

In some embodiments, provided herein are compositions for the treatment of a condition or disease of the skin. As described in more detail herein, such conditions or diseases are conditions or disease of the epidermis, the dermis or the hypodermis (e.g., subcutaneous tissue). In some cases, a condition or a disease is a condition or a disease of the stratum corneum, the stratum germinativum, the statum *spinosum*, the stratum basale, the dermal papilla, a sebaceous gland, a hair follicle, a nerve fiber, a arrector pili muscle, the dermal papilla, a sweat gland, or a combination of any of these. The skin can include the skin of any surface of the body. For example, skin from a head, an arm, a leg, a torso, a stomach, a foot, a toe, a finger, a thumb, a forearm, a back, a groin or any region on the body. In some cases, compositions described comprises isolated bacteria present in an amount sufficient for a reduction in incidence of colonization of a pathogenic bacteria, fungi or virus. In some cases, compositions described comprises isolated bacteria present in an amount sufficient for a reduction in the gene expression of a pathogenic bacteria, fungi or virus. In some cases, compositions described comprises isolated bacteria present in an amount sufficient for a reduction in the metabolism of a pathogenic bacteria, fungi or virus. In some cases, compositions described comprises isolated bacteria present in an amount sufficient for a reduction in the virulence of a pathogenic bacteria, fungi or virus. In some cases, a disease or condition can relate to a bacterial infection. Sources for bacterial infections for treatment with pharmaceutical compositions described herein include, without limitation, *S. aureus* (methicillin-resistant *S. aureus* (MRSA) and methicillin-sensitive *S. aureus* (MS SA)), *Gardnerella* vagina/is, and *Streptococcus pyogenes*.

In some embodiments, a skin condition or disease is treated by administering a composition described herein. In some cases, treating can be used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms of an underlying disorder being treated. In some cases, a prophylactic effect can include delaying, preventing, or eliminating the appearance of a disease or condition, delaying or eliminating the onset of symptoms of a disease or condition, slowing, halting, or reversing the progression of a disease or condition. In some cases, an inflammation is treated by administering a composition described herein. Skin conditions and disease for treatment following administration of a composition described herein include, without limitation, a mycoses, a dry skin, an itchy skin, a dermatophytosis (*trichophyton*), a bacterial folliculitis, a bacterial infection, an inflammatory condition, or a genetic condition. Skin conditions and disease for treatment following administration of a composition described herein comprises a skin and soft tissue infection. In some cases, administration of a composition described herein comprises restoration of an eczema prone microbiome. For example, an eczema prone microbiome can be restored to a healthy or non-eczema prone microbiome. In some instances, a mycoses comprises *malassezia* folliculitis, tinea *versicolor*, cutaneous candidiasis, candidal paronychia. In some instances, a dermatophytosis (*trichophyton*) comprises tinea capitis (scalp ringworm), tinea barbae (beard ringworm), tinea corporis (body ringworm), tinea cruris ("jock itch"), tinea pedis ("athlete's foot"), tinea capitis (scalp ringworm), tinea barbae (beard ringworm), tinea corporis (body ringworm), tinea unguium (nails, onychomycosis), tinea manuum (hand), tinea faciei (face). In some instances, a bacterial infection comprises *S. aureus* folliculitis, folliculitis, sycosis vulgaris ("barber's itch"), staphylococcal scalded skin syndrome, impetigo, ecthyma, cellulitis, a boil, an abscess, a furuncle, a mastitis, ecthyma, erysipelas, necrotizing fasciitis, secondary skin infection (e.g., of a wound, dermatitis, scabies, diabetic ulcers etc.), tropical ulcers, blistering distal dactylitis, streptococcal perianal and/or vulval dermatitis. In some cases, a disease or condition comprises atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some instances, a genetic condition comprises Netherton syndrome. In some instances, an inflammatory condition comprises atopic dermatitis, contact dermatitis, eczema, pruritus, seborrheic dermatitis, acne (acne vulgaris), psoriasis (psoriasis vulgaris, plaque psoriasis), rosacea, hidradenitis suppurativa. In some cases, a skin condition comprises an aging condition, such as wrinkles. In some cases, a skin condition comprises dandruff, or a sunburn. In some cases, a skin disease or condition comprises eczema, diaper rash, seborrheic dermatitis, chickenpox, measles, warts, acne, fifth disease, hives, ringworm, rashes from a bacterial or a fungal infections (e.g., cutaneous candidiasis), or rashes from an allergic reaction.

In some embodiments, a composition described herein is administered to treat a vaginal condition. Vaginal conditions and diseases for treatment following administration of a composition described herein can include vulvovaginal candidiasis, recurrent vulvovaginal candidiasis, and bacterial vaginosis.

In some embodiments, provided herein are methods of preventing or reducing a skin condition in a subject, comprising topically administering to a subject a composition described herein. In some cases, compositions and methods described herein are compositions used to improve a cosmetic irregularity. In some cases, compositions and methods described herein are compositions used to treat a condition selected from the group consisting of: a pruritus, an aesthetic condition, and a body odor. In some cases, an aesthetic condition comprises wrinkles or appearance of aging. In some instances, an aesthetic condition is a cosmetic irregularity. Improvement of the cosmetic irregularity may result in reduced fine line occurrence, fine line depth, wrinkle occurrence, wrinkle depth, scaly patches, roughness, acne, scars, irregular pigmentation, sun spots, liver spots, solar lentigines, melasma, poikiloderma, actinic keratoses, lentigo maligna, periorbital hyperpigmentation, shine, sheen, oily appearance, blistering, peeling, sloughing, flaking, or pore size; improved skin tone, skin firmness, tactile smoothness, suppleness, glow, visual smoothness, or radiance. In addition, improvement of the cosmetic irregularity with a composition or method described herein may reduce a pathogenic bacteria, virus or fungi on and/or in the skin of a subject in need thereof. In some cases, compositions and methods described herein provide for enhanced barrier function of the skin as measured by trans-epidermal water loss. Administrations described herein, e.g., topical, oral, or rectal, may reduce reoccurrences, so that additional incidents of the cosmetic irregularities of the skin are reduced in number, intensity, or frequency. The administration may increase the time of remission, such as the length of time between incidents. In some embodiments, an additional incident of cosmetic irregularity does not occur for 1, 2, 3, 4, 5, 6, 7, 8, 9, 10, 11, or 12 weeks following application. In some embodiments, an additional incident of cosmetic irregularity does not occur for 1, 2, 3, 4, 5, 6, 7, 8, 9, 10, 11, or 12 months following the topical application. For example, a composition herein is administered to reduce wrinkles, decrease lesion size, decrease pore size, or decrease pore density. Further provided herein are methods of preventing or reducing a skin condition in a subject, wherein the skin condition comprises fine line occurrence, fine line depth, wrinkle occurrence, wrinkle depth, nasolabial folds, scaly patches, roughness, acne, scars, redness, irregular pigmentation, decreased tightness, decreased skin barrier, age spots, sun spots, liver spots, photo damage, sunlight exposure, damage from sunlight exposure, environmental damage, solar lentigines, melasma, poikiloderma, actinic keratoses, lentigo maligna, periorbital hyperpigmentation, shine, sheen, oily appearance, decrease of skin's ability to retain moisture, abnormal skin epidermal thickness, reduction of dermal epidermal junction, blistering, peeling, sloughing, flaking, pore size, skin tone, skin firmness, skin texture, skin elasticity, tactile smoothness, suppleness, glow, visual smoothness, radiance or a combination thereof. In some cases, efficacy assessments of skin conditions and/or cosmetic irregularity to a treatment can be clinically graded using a ten-point scale, on a subject's treatment area (e.g., a subject's face) (where 0=none, 0.5-3.5=mild, 4-6.5=moderate and 7-10=severe). In some cases, efficacy assessments can be taken over a period of time, for example, after each treatment, or every week, or every month. All grading assessments can be performed by the same investigator at each visit or by a computer implementing an algorithm to ensure grading consistency. In some cases, a measurement is taken, such as the number or wrinkles, or the depth of wrinkles, and is a factor in a clinical score.

In some embodiments, a symptom of inflammation is treated by administering a composition described herein. In some embodiments, a symptom of a skin condition or disease is treated by administering a composition described herein. For example, a composition can be administered in an amount sufficient to reduce symptoms associated with atopic dermatitis. In some cases, a symptom comprises a raised bump, a discolored bump, a rash, a pain, an itch, a scaly skin, a rough skin, a peeling skin, an ulcer, an open sore, a lesion, a dry skin, a cracked skin, a discolored patch of skin, a fleshy bump, a wart, a skin growth, a mole, a change in a mole size or color, a loss of skin pigment, or an excessive flushing. In some cases, a symptom comprises an itch, a rash, a redness, a pain, a swelling, a blistering, or a scaling. In some embodiments, a composition is administered in an amount sufficient to reduce symptoms associated with dry skin. In some cases, a composition is administered in an amount sufficient for a reduction of incidence of a condition associated with inflammation, for example an itch, a rash, a redness, a pain, a swelling, a blistering, or a scaling.

In some embodiments, a method for the treatment of inflammation comprises topically administering a composition comprising *Bacillus wiedmannii* to a subject in need thereof. In some cases, the *Bacillus wiedmannii* is purified, and the *Bacillus wiedmannii* is present in an amount sufficient for treatment of inflammation. In some embodiments, a method comprises reducing growth of *S. aureus* on the skin of a subject in need thereof. In some cases, the method comprises topically administering a pharmaceutical composition comprising *Bacillus velezensis*, *Bacillus wiedmannii*, and *Lysinibacillus macroides* to a skin of the subject in need thereof. In some cases, the *Bacillus velezensis*, the *Bacillus wiedmannii*, and the *Lysinibacillus macroides* are purified, and the *Bacillus velezensis*, the *Bacillus wiedmannii*, and the *Lysinibacillus macroides* are viable, and are present in an amount sufficient for reduction of *S. aureus* on a skin of the subject in need thereof. In some embodiments, a method for the reduction of symptoms associated with atopic dermatitis comprises topically administering a composition comprising *Bacillus amyloliquefaciens* to a subject in need thereof. In some cases, the *Bacillus amyloliquefaciens* is purified, and the *Bacillus amyloliquefaciens* is present in an amount sufficient for the reduction of symptoms associated with atopic dermatitis. In some embodiments, a method for reducing the incidence of a condition associated with inflammation comprises topically administering a composition comprising *Bacillus wiedmannii* and *Staphylococcus caprae* to a subject in need thereof. In some cases, the *Bacillus wiedmannii* and the *Staphylococcus caprae* are purified. In some cases, the *Bacillus wiedmannii* and the *Staphylococcus caprae* are present in an amount sufficient for a reduction of the incidence of a condition associated with inflammation. In some instances, the condition associated with inflammation comprises an itch, a rash, a redness, a pain, a swelling, a blistering, or a scaling.

In some embodiments, a method for the treatment of inflammation comprises topically administering a composition comprising bacterial Strain jl.27 to a subject in need thereof. In some cases, the Strain jl.27 is purified, and the Strain jl.27 is present in an amount sufficient for treatment of inflammation. In some embodiments, a method comprises reducing growth of *S. aureus* on the skin of a subject in need thereof. In some cases, the method comprises topically administering a pharmaceutical composition comprising Strain jl.83, Strain jl.27, and Strain jl.77 to a skin of the subject in need thereof. In some cases, the Strain jl.83, the Strain jl.27 and the Strain jl.77 are purified, and the Strain jl.83, the Strain jl.27, and the Strain jl.77 are viable, and are present in an amount sufficient for reduction of *S. aureus* on a skin of the subject in need thereof. In some embodiments, a method for the reduction of symptoms associated with atopic dermatitis comprises topically administering a composition comprising Strain jl.68 to a subject in need thereof. In some cases, the Strain jl.68 is purified, and the Strain jl.68 is present in an amount sufficient for the reduction of symptoms associated with atopic dermatitis. In some embodiments, a method for reducing the incidence of a condition associated with inflammation comprises topically administering a composition comprising Strain jl.27 and Strain jl.121 to a subject in need thereof. In some cases, the Strain jl.27 and the Strain jl.121 are purified. In some cases, the Strain jl.27 and the Strain jl.121 are present in an amount sufficient for a reduction of the incidence of a condition associated with inflammation. In some instances, the condition associated with inflammation comprises an itch, a rash, a redness, a pain, a swelling, a blistering, or a scaling.

Kits

Pharmaceutical compositions described herein may include kits where bacteria described herein are included in a first container (e.g., lyophilized cells), and one or more pharmaceutical acceptable excipients are included in a second container (e.g., water or a buffered solution). In some embodiments, provided herein are kits, wherein the kit comprises: a first container, wherein the first container comprises a purified, and lyophilized bacteria that comprises: *Staphylococcus cohnii*, *Staphylococcus capitis*, *Staphylococcus caprae*, *Bacillus tropicus*, *Bacillus mycoides*, *Bacillus wiedmannii*, *Bacillus mediterraneensis*, *Bacillus amyloliquefaciens*, *Bacillus velezensis*, *Bacillus cereus*, *Bacillus cecembensis*, *Kocuria marina*, *Lysinibacillus macrolides*, or a mixture thereof; and a second container, wherein the second container comprises a pharmaceutically acceptable excipient. In some embodiments, provided herein are kits, wherein the kit comprises: a first container, wherein the first container comprises a purified, and lyophilized bacteria that comprises: Strain ji.83, Strain ji.27, Strain ji.77, Strain ji.68, Strain jl.121, Strain jl.21, or a mixture thereof; and a second container, wherein the second container comprises a pharmaceutically acceptable excipient. In some embodiments, provided herein are kits, wherein the kit comprises: a first container, wherein the first container comprises a purified, and lyophilized bacteria that comprises: *Bacillus velezensis, Bacillus wiedmannii,* and *Lysinibacillus macrolides*; and a second container, wherein the second container comprises a pharmaceutically acceptable excipient. In some embodiments, provided herein are kits, wherein the kit comprises: a first container, wherein the first container comprises a purified, and lyophilized bacteria that comprises: *Bacillus amyloliquefaciens, Bacillus wiedmannii,* and *Staphylococcus caprae*; and a second container, wherein the second container comprises a pharmaceutically acceptable excipient. In some embodiments, provided herein are kits, wherein the kit comprises: a first container, wherein the first container comprises a purified, and lyophilized bacteria that comprises: *Bacillus amyloliquefaciens; Bacillus tropicus*; and *Staphylococcus caprae*; and a second container, wherein the second container comprises a pharmaceutically acceptable excipient.

In some embodiments, provided herein are kits, wherein the kit comprises: a first container, wherein the first container comprises a purified, and lyophilized bacteria that comprises: Strain jl.83, Strain jl.27, and Strain jl.77; and a second container, wherein the second container comprises a pharmaceutically acceptable excipient. In some embodiments, provided herein are kits, wherein the kit comprises: a first container, wherein the first container comprises a purified, and lyophilized bacteria that comprises: Strain jl.68, Strain jl.27, and Strain jl.121; and a second container, wherein the second container comprises a pharmaceutically acceptable excipient. In some embodiments, provided herein are kits, wherein the kit comprises: a first container, wherein the first container comprises a purified, and lyophilized bacteria that comprises: Strain jl.68; Strain jl.21; and Strain jl.121; and a second container, wherein the second container comprises a pharmaceutically acceptable excipient.

In some embodiments, provided herein are kits, wherein the kit comprises: a first container, wherein the first container comprises a purified, and lyophilized bacteria present in a total amount of at least 10^3 cfu that comprises: one or more species from Table 1 and/or one or more strains from Table 2; and a second container, wherein the second container comprises a pharmaceutically acceptable excipient. In some instances, a kit comprises 1, 2, 3, 4, 5, or more containers, such that each container comprises an individual strain or species of bacteria. Further provided herein are kits, wherein the purified, and lyophilized bacteria are present in a total amount of up to 10..cfu. Further provided herein are kits, wherein the purified, and lyophilized bacteria are present in a total amount of 10^3 to 10^12 cfu.

NUMBERED EMBODIMENTS

A number of compositions, and methods are disclosed herein. Specific exemplary embodiments of these compositions and methods are disclosed below. The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed.

Embodiment 1. A composition, wherein the composition comprises: bacterial species that are purified, wherein the bacterial species comprise: *Bacillus velezensis, Bacillus wiedmannii,* and *Lysinibacillus macroides*; and wherein (a) the bacterial species are lyophilized; or (b) the composition is formulated for delivery to a skin.

Embodiment 2. The composition of embodiment 1, wherein the composition is formulated as: a suspension, an emulsion, a cream, a lotion, a tincture, a gel, a foam, a powder, an ointment, a paste, or an oil.

Embodiment 3. The composition of embodiment 1, further comprising a fourth bacterial species.

Embodiment 4. A composition, wherein the composition comprises: bacterial species that are purified, wherein the bacterial species comprise: *Bacillus amyloliquefaciens; Bacillus wiedmannii;* and *Staphylococcus caprae*; and wherein (a) the bacterial species are lyophilized; or (b) the composition is formulated for delivery to a skin.

Embodiment 5. The composition of embodiment 4, wherein the composition is formulated as: a suspension, an emulsion, a cream, a lotion, a tincture, a gel, a foam, a powder, an ointment, a paste, or an oil.

Embodiment 6 The composition of embodiment 4, further comprising a fourth bacterial species.

Embodiment 7. A composition, wherein the composition comprises: bacterial species that are purified, wherein the bacterial species comprise: *Bacillus amyloliquefaciens; Bacillus tropicus;* and *Staphylococcus caprae*; and wherein (a) the bacterial species are lyophilized; or (b) the composition is formulated for delivery to a skin.

Embodiment 8. The composition of embodiment 7, wherein the composition is formulated as: a suspension, an emulsion, a cream, a lotion, a tincture, a gel, a foam, a powder, an ointment, a paste, or an oil.

Embodiment 9. The composition of embodiment 7, further comprising a fourth bacterial species.

Embodiment 10. A composition, wherein the composition comprises: bacterial species that are purified, wherein the bacterial species comprise at least two of the following bacterial species: *Bacillus velezensis, Bacillus wiedmannii, Lysinibacillus macrolides, Bacillus amyloliquefaciens, Staphylococcus caprae,* and *Bacillus tropicus,* and wherein (a) the at least two bacterial species are lyophilized; or (b) the composition is formulated for delivery to a skin.

Embodiment 11. The composition of embodiment 10, wherein the composition is formulated as: a suspension, an emulsion, a cream, a lotion, a tincture, a gel, a foam, a powder, an ointment, a paste, or an oil.

Embodiment 12. A composition, wherein the composition comprises: a bacterial species that is purified, wherein the bacterial species comprises: *Bacillus velezensis*; and wherein (a) the bacterial species is lyophilized; or (b) the composition is formulated for delivery to a skin.

Embodiment 13. The composition of embodiment 12, wherein the composition is formulated as: a suspension, an emulsion, a cream, a lotion, a tincture, a gel, a foam, a powder, an ointment, a paste, or an oil.

Embodiment 14. The composition of embodiment 12, further comprising a second bacterial species.

Embodiment 15. A composition, wherein the composition comprises: a bacterial species that is purified, wherein the bacterial species comprises: *Bacillus wiedmannii;* and wherein (a) the bacterial species is lyophilized; or (b) the composition is formulated for delivery to a skin.

Embodiment 16. The composition of embodiment 15, wherein the composition is formulated as: a suspension, an emulsion, a cream, a lotion, a tincture, a gel, a foam, a powder, an ointment, a paste, or an oil.

Embodiment 17. The composition of embodiment 15, further comprising a second bacterial species.

Embodiment 18. A composition, wherein the composition comprises: a bacterial species that is purified, wherein the bacterial species comprises: *Lysinibacillus macroides*; and wherein (a) the bacterial species is lyophilized; or (b) the composition is formulated for delivery to a skin.

Embodiment 19. The composition of embodiment 18, wherein the composition is formulated as: a suspension, an emulsion, a cream, a lotion, a tincture, a gel, a foam, a powder, an ointment, a paste, or an oil.

Embodiment 20. The composition of embodiment 18, further comprising a second bacterial species.

Embodiment 21. A composition, wherein the composition comprises: a bacterial species that is purified, wherein the bacterial species comprises: *Bacillus tropicus*; and wherein (a) the bacterial species is lyophilized; or (b) the composition is formulated for delivery to a skin.

Embodiment 22. The composition of embodiment 21, wherein the composition is formulated as: a suspension, an emulsion, a cream, a lotion, a tincture, a gel, a foam, a powder, an ointment, a paste, or an oil.

Embodiment 23. The composition of embodiment 21, further comprising a second bacterial species.

Embodiment 24. The composition of any one of embodiments 1-23, wherein the composition comprises at least $10^3$ colony forming units (cfu) per gram of bacteria.

Embodiment 25. The composition of any one of embodiments 1-24, wherein the composition comprises $10^3$ to $10^{12}$ colony forming units (cfu) per gram of bacteria.

Embodiment 26. The composition of any one of embodiments 1-25, wherein the bacterial species are grown in aerobic conditions.

Embodiment 27. The composition of any one of embodiments 1-26, wherein the bacterial species are grown without animal products.

Embodiment 28. The composition of any one of embodiments 1-27, wherein the bacterial species are grown in Tryptic Soy Broth (TSB).

Embodiment 29. The composition of any one of embodiments 1-28, wherein the composition when stored in a sealed container placed at 20° C. retains greater than about: $10^4$ cfu after 6 months, as measured by cfu counts.

Embodiment 30. The composition of any one of embodiments 1-29, further comprising an excipient.

Embodiment 31. The composition of any one of embodiments 1-30, further comprising a lyoprotectant.

Embodiment 32. The composition of any one of embodiments 1-31, further comprising an emollient.

Embodiment 33. The composition of any one of embodiments 1-32, further comprising thiamine or a salt thereof.

Embodiment 34. The composition of any one of embodiments 1-33, wherein the bacterial species when contacted with *S. aureus* cause a reduction in expression of at least one of the following genes: gmk, agr, psma, saeR, ccpA, and SigB in *S. aureus*, wherein the reduction in expression is measured by a fluorescence reporter assay.

Embodiment 35. The composition of any one of embodiments 1-33, wherein the bacterial species is present in an amount effective to suppress virulence of *S. aureus* as measured by a reduction in expression of at least one of the following genes: gmk, agr, psma, saeR, ccpA, and SigB in *S. aureus* wherein the reduction in expression is measured by a fluorescence reporter assay.

Embodiment 36. A method of administering the composition of any one of embodiments 1-35, comprising administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess.

Embodiment 37. A method of administering the composition of any one of embodiments 1-35, comprising administering an amount sufficient to reduce symptoms associated with atopic dermatitis.

Embodiment 38. A method of administering the composition of any one of embodiments 1-35, comprising administering the composition to a subject who has an eczema prone microbiome prior to the administration.

Embodiment 39. A method of administering the composition of any one of embodiments 1-35, comprising administering an amount sufficient to reduce symptoms associated with dry skin.

Embodiment 40. A method of administering the composition of any one of embodiments 1-35, comprising administering an amount sufficient for a reduction of incidence of a condition associated with inflammation and wherein the condition associated with inflammation comprises an itch, a rash, a redness, a pain, a swelling, a blistering, or a scaling.

Embodiment 41. A method of administering the composition of any one of embodiments 1-35, comprising administering an amount sufficient to suppress virulence of *S. aureus* as measured by a reduction in expression of at least one of the following genes: gmk, agr, psma, saeR, ccpA, and SigB in *S. aureus*, wherein the reduction in expression is measured by a fluorescence reporter assay.

Embodiment 42. A composition of any one of embodiments 1-35, for use in the treatment of a skin condition.

Embodiment 43. A composition of any one of embodiments 1-35, for use in the treatment of inflammation.

Embodiment 44. A method for treatment of inflammation, comprising: topically administering a composition comprising *Bacillus wiedmannii* to a subject in need thereof, wherein the *Bacillus wiedmannii* is purified, and wherein the *Bacillus wiedmannii* is present in an amount sufficient for treatment of inflammation.

Embodiment 45. A method for reducing growth of *Staphylococcus aureus* on skin of a subject in need thereof, comprising: topically administering a pharmaceutical composition comprising *Bacillus velezensis*, *Bacillus wiedmannii*, and *Lysinibacillus macroides* to a skin of the subject in need thereof, wherein the *Bacillus velezensis*, the *Bacillus wiedmannii*, and the *Lysinibacillus macroides* are purified, and wherein the *Bacillus velezensis*, the *Bacillus wiedmannii*, and the *Lysinibacillus macroides* are viable, and present in an amount sufficient for reduction of *S. aureus* on a skin of the subject in need thereof.

Embodiment 46. A method for reduction of symptoms associated with atopic dermatitis, comprising: topically administering a composition comprising *Bacillus amyloliquefaciens* to a subject in need thereof, wherein the *Bacillus amyloliquefaciens* is purified, and wherein the *Bacillus amyloliquefaciens* is present in an amount sufficient for the reduction of symptoms associated with atopic dermatitis.

Embodiment 47. A method for reducing an incidence of a condition associated with inflammation comprising: topically administering a composition comprising *Bacillus wiedmannii* and *Staphylococcus caprae* to a subject in need thereof, wherein the *Bacillus wiedmannii* and the *Staphylococcus caprae* are purified, wherein the *Bacillus wiedmannii* and the *Staphylococcus caprae* are present in an amount sufficient for a reduction of the incidence of a condition associated with inflammation and wherein the condition associated with inflammation comprises an itch, a rash, a redness, a pain, a swelling, a blistering, or a scaling.

Embodiment 48. A method of administering the composition of any one of embodiments 1-35, comprising administering an amount sufficient to treat a condition selected from the group consisting of: pruritis, an aesthetic condition, and body odor.

Embodiment 49. The method of embodiment 48, wherein the aesthetic condition comprises wrinkles or appearance of aging.

Summary of Embodiments

Disclosed herein are compositions. In some embodiments, a composition comprises bacterial species that are purified. In some embodiments, the bacterial species comprises: *Bacillus velezensis; Bacillus wiedmannii*; and *Lysinibacillus macroides*. In some embodiments (a) the bacterial species are lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition can further comprise a fourth bacterial species. In some embodiments, the composition comprises at least $10^3$ colony forming units (cfu) per gram of bacteria. In some embodiments, the composition comprises $10^3$ to $10^{12}$ colony forming units (cfu) per gram of bacteria. In some embodiments, the bacterial species are grown in aerobic conditions. In some embodiments, the bacterial species are grown without animal products. In some embodiments, the bacterial species are grown in Tryptic Soy Broth (TSB). In some embodiments, the composition when stored in a sealed container placed at 20° C. can retain greater than about $10^{-4}$ cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species are present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises bacterial species that are purified. In some embodiments, the bacterial species comprises: *Bacillus amyloliquefaciens, Bacillus wiedmannii*, and *Staphylococcus caprae*. In some embodiments, (a) the bacterial species are lyophilized; or (b) the composition is formulated for delivery to a skin. In some embodiments, a composition is formulated as: a suspension, an emulsion, a cream, a lotion, a tincture, a gel, a foam, a powder, an ointment, a paste, or an oil. In some embodiments, the composition can further comprise a fourth bacterial species. In some embodiments, the composition comprises at least $10^3$ colony forming units (cfu) per gram of bacteria. In some embodiments, the composition comprises $10^3$ to $10^{12}$ colony forming units (cfu) per gram of bacteria. In some embodiments, the bacterial species are grown in aerobic conditions. In some embodiments, the bacterial species are grown without animal products. In some embodiments, the bacterial species are grown in Tryptic Soy Broth (TSB). In some embodiments, the composition when stored in a sealed container placed at 20° C. can retain greater than about $10^4$ cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species are present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises bacterial species that are purified. In some embodiments, the bacterial species comprises: *Bacillus amyloliquefaciens, Bacillus tropicus*, and *Staphylococcus caprae*. In some embodiments, (a) the bacterial species are lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition can further comprise a fourth bacterial species. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial species are grown in aerobic conditions. In some embodiments, the bacterial species are grown without animal products. In some embodiments, the bacterial species are grown in Tryptic Soy Broth (TSB). In some embodiments, the composition when stored in a sealed container placed at 20° C. can retain greater than about 10^4 cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species is present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of: pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises bacterial species that are purified. In some embodiments, the bacterial species comprises at least two of the following bacterial species: *Bacillus velezensis, Bacillus wiedmannii, Lysinibacillus macrolides, Bacillus amyloliquefaciens, Staphylococcus caprae*, and *Bacillus tropicus*. In some embodiments, (a) the at least two bacterial species are lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial species are grown in aerobic conditions. In some embodiments, the bacterial species are grown without animal products. In some embodiments, the bacterial species are grown in Tryptic Soy Broth (TSB). In some embodiments, the composition when stored in a sealed container placed at 20° C. can retain greater than about 10^4 cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species are present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises a bacterial species that is purified. In some embodiments, the bacterial species comprises: *Bacillus velezensis*. In some embodiments, (a) the bacterial species is lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition can further comprise a second bacterial species. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial species is grown in aerobic conditions. In some embodiments, the bacterial species is grown without animal products. In some embodiments, the bacterial species is grown in Tryptic Soy Broth (TSB). In some embodiments, the composition when stored in a sealed container placed at 20° C. can retain greater than about 10^4 cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species is present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of: pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises a bacterial species that is purified. In some embodiments, the bacterial species comprises *Bacillus wiedmannii*. In some embodiments, (a) the bacterial species is lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition can further comprise a second bacterial species. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial species is grown in aerobic conditions. In some embodiments, the bacterial species is grown without animal products. In some embodiments, the bacterial species is grown in Tryptic Soy Broth (TSB). In some embodiments, the composition when stored in a sealed container placed at 20° C. can retain greater than about 10^4 cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species is present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises a bacterial species that is purified. In some embodiments, the bacterial species comprises: *Lysinibacillus macroides*. In some cases, (a) the bacterial species is lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition can further comprise a second bacterial species. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial species is grown in aerobic conditions. In some embodiments, the bacterial species is grown without animal products. In some embodiments, the bacterial species is grown in Tryptic Soy Broth (TSB). In some embodiments, the composition when stored in a sealed container placed at 20° C. can retain greater than about 10^4 cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species is present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

In some embodiments, a composition comprises a bacterial species that is purified. In some embodiments, the bacterial species comprises *Bacillus tropicus*. In some embodiments, (a) the bacterial species is lyophilized; or (b) the composition is formulated for delivery to a skin. In some embodiments, the composition is formulated as: a suspension, an emulsion, a cream, a lotion, a tincture, a gel, a foam, a powder, an ointment, a paste, or an oil. In some embodiments, the composition can further comprise a second bacterial species. In some embodiments, the composition comprises at least 10^3 colony forming units (cfu) per gram of bacteria. In some embodiments, the composition comprises 10^3 to 10^12 colony forming units (cfu) per gram of bacteria. In some embodiments, the bacterial species is grown in aerobic conditions. In some embodiments, the bacterial species is grown without animal products. In some embodiments, the bacterial species is grown in Tryptic Soy Broth (TSB). In some embodiments, the composition when stored in a sealed container placed at 20° C. can retain greater than about 10^4 cfu after 6 months, as measured by cfu counts. In some embodiments, the composition can further comprise an excipient. In some embodiments, the composition can further comprise a lyoprotectant. In some embodiments, the composition can further comprise an emollient. In some embodiments, the composition can further comprise thiamine or a salt thereof. In some embodiments, the bacterial species when contacted with *S. aureus* can cause a reduction in expression of at least one of the following genes: gmk, agr, psma, saeR, ccpA, and SigB in *S. aureus*. In some embodiments, the reduction in expression is measured by a fluorescence reporter assay. In some embodiments, the bacterial species is present in an amount effective to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. Also disclosed herein are methods of administering the composition. In some embodiments, the method comprises administering an amount sufficient to treat a disease selected from the group consisting of: atopic dermatitis, seborrheic dermatitis, inflammation, eczema, psoriasis, rosacea, mycoses, dermatophytosis, folliculitis, acne, alopecia, vitiligo, dandruff, chronic wound, skin ulcer, Netherton syndrome, hidradenitis suppurativa, sycosis vulgaris, staphylococcal scalded skin syndrome, impetigo, ecthyma, cellulitis, carbuncle, furuncle, and abscess. In some embodiments, the method comprises administering an amount sufficient to treat a condition selected from the group consisting of: pruritis, an aesthetic condition, and body odor. In some embodiments, the aesthetic condition comprises wrinkles or appearance of aging. In some embodiments, the method comprises administering an amount sufficient to reduce symptoms associated with atopic dermatitis. In some embodiments, the method comprises administering the composition to a subject who has an eczema prone microbiome prior to the administration. In some embodiments, the method comprises administering an amount sufficient to reduce symptoms associated with dry skin. In some embodiments, the method comprises administering an amount sufficient for a reduction of incidence of a condition associated with inflammation and wherein the condition associated with inflammation comprises an itch, a rash, a redness, a pain, a swelling, a blistering, or a scaling. In some embodiments, the method comprises administering an amount sufficient to suppress virulence of *S. aureus* as measured by a reduction in expression of at least one of the following genes: gmk, agr, psma, saeR, ccpA, and SigB in *S. aureus*. In some embodiments, the reduction in expression is measured by a fluorescence reporter assay. In some embodiments, the composition is for use in the treatment of a skin condition. In some embodiments, the composition is for use in the treatment of inflammation.

Also disclosed herein are methods for the treatment of inflammation, comprising topically administering a composition comprising *Bacillus wiedmannii* to a subject in need thereof. In some embodiments, the *Bacillus wiedmannii* is purified. In some embodiments, the *Bacillus wiedmannii* is present in an amount sufficient for treatment of inflammation.

Also disclosed herein are methods for reducing growth of *Staphylococcus aureus* on skin of a subject in need thereof, comprising topically administering a pharmaceutical composition comprising *Bacillus velezensis*, *Bacillus wiedmannii*, and *Lysinibacillus macroides* to a skin of the subject in need thereof. In some embodiments, the *Bacillus velezensis*, the *Bacillus wiedmannii*, and the *Lysinibacillus macroides* are purified. In some embodiments, the *Bacillus velezensis*, the *Bacillus wiedmannii*, and the *Lysinibacillus macroides* are viable, and present in an amount sufficient for reduction of *S. aureus* on a skin of the subject in need thereof.

Also disclosed herein are methods for reducing of symptoms associated with atopic dermatitis comprising topically administering a composition comprising *Bacillus amyloliquefaciens* to a subject in need thereof. In some embodiments, the *Bacillus amyloliquefaciens* is purified. In some embodiments, the *Bacillus amyloliquefaciens* is present in an amount sufficient for the reduction of symptoms associated with atopic dermatitis.

Also disclosed herein are methods for reducing an incidence of a condition associated with inflammation comprising topically administering a composition comprising *Bacillus wiedmannii* and *Staphylococcus caprae* to a subject in need thereof. In some embodiments, the *Bacillus wiedmannii* and the *Staphylococcus caprae* are purified. In some embodiments, the *Bacillus wiedmannii* and the *Staphylococcus caprae* are present in an amount sufficient for a reduction of the incidence of a condition associated with inflammation. In some embodiments, the condition associated with inflammation comprises an itch, a rash, a redness, a pain, a swelling, a blistering, or a scaling.

EXAMPLES

Example 1: Bacterial Strains and Screening 1750 bacterial isolates were picked from different sites on the skin of 20 healthy donors. Of the 1750 strains, 609 strains were frozen, and 180 strains were selected for an initial screen. The 180 strains were identified by 16S full length sequencing using Sanger sequencing. The reads were trimmed and concatenated. The 16S sequence was compared by a BLAST algorithm to the NCBI 16S database and species were identified as the top hit from the database. A minimal threshold was applied to the sequence for quality control. The top 28 strains from the 180 strains in the initial screen were further selected for several experiments. Table 1 shows the species from the top 28 strains selected.

Strains were screened in an array assay as a comprehensive approach to determine isolate(s) interaction with strains of *S. aureus*. Briefly, isolates and *S. aureus* strains were added to an array assay that contains thousands of microwells. Strains were mixed with molecules of different wavelengths for identification and when mixed create a unique wavelength code that is read by an imaging device to determine input. The *S. aureus* strains were promoter/reporter strains that were used to screen for inhibition of gene expression. Decreased expression of the promoter/reporter strains when grown with skin isolate(s) was indicated as a decreased fluoresce as compared to the promoter/reporter strain grown alone.

The *S. aureus* promoter/reporter strains contained a fluorescent reporter under the control of a promoter of a gene of interest. The promoter/reporter strains generated were as follows: Strain 1-agr promoter for quorum sensing induction, Strain 2-psmA promoter for a toxin that damages host tissue, Strain 3-saeR promoter for virulence regulation, Strain 4-sigB promoter for the stress response sigma factor, Strain 5-ccpA promoter for metabolism (e.g., carbon catabolite repression), and strain 6-GMK promoter for constitutive metabolic function.

Besides an array assay, strains could be tested for gene expression inhibition in a wide variety of assays such as in a microtiter plate growth assay, or another liquid culture growth assay. In another example, strains could be screened for gene inhibition on an agar plate.

Example 2: Pairwise Assays of Bacterial Isolates for *S. aureus* Gene Expression Inhibition 180 diverse bacterial isolates from the skin of healthy individuals were screened in a pairwise combinatorial screening assay against 4 *S. aureus* behavior reporters. *S. aureus* behaviors were measured via a set of plasmid-mediated "promoter-reporter" strains, whose fluorescence report on one specific activity. Combinations of strains were screened in an array assay for 10 days. The controls were: 1) no-isolate, which was a *S. aureus* monoculture, 2) wild-type *S. aureus*, and 3) streptomycin for a negative control, for *S. aureus* eradication. The screen analyzed the reporters GMK for constitutive metabolic function, agr for quorum sensing induction, psmA for toxin that damages host tissue, and sigB for the stress response sigma factor. Referring to FIG. 1, FIG. 1 on the left shows out of the 180 bacterial isolates that were screened only 3.8% of the pairwise combinations inhibited agr and psmA to 3 folds or 12.5% of monoculture levels. Similarly, FIG. 1 on the right shows out of the 180 bacterial isolates that were screened, only 1.10% of the pairwise combinations inhibited agr, psmA, and sigB to 3 folds or 12.5% of monoculture levels. These data show combinations that possess multiple functions are rare.

Example 3: Three-Wise Assays of Bacterial Isolates for *S. aureus* Gene Expression Inhibition Bacterial isolates from the skin of healthy individuals were screened in a three-wise combinatorial screening assay against 6 *S. aureus* behavior reporters. *S. aureus* behaviors were measured via a set of plasmid-mediated "promoter-reporter" strains, whose fluorescence report on one specific activity. Combinations of strains were screened in an array assay for 4 days. The strain mixture conditions were: 1) no-isolate, which was a *S. aureus* monoculture, 2) wild-type *S. aureus* with isolated strains, and 3) streptomycin for a negative control, for *S. aureus* eradication. The screen analyzed the expression of the reporters agr for quorum sensing induction, psmA for toxin that damages host tissue, saeR for virulence regulation, sigB for the stress response sigma factor, ccpA for metabolism (e.g., carbon catabolite repression), and GMK for constitutive metabolic function.

Figure 2:
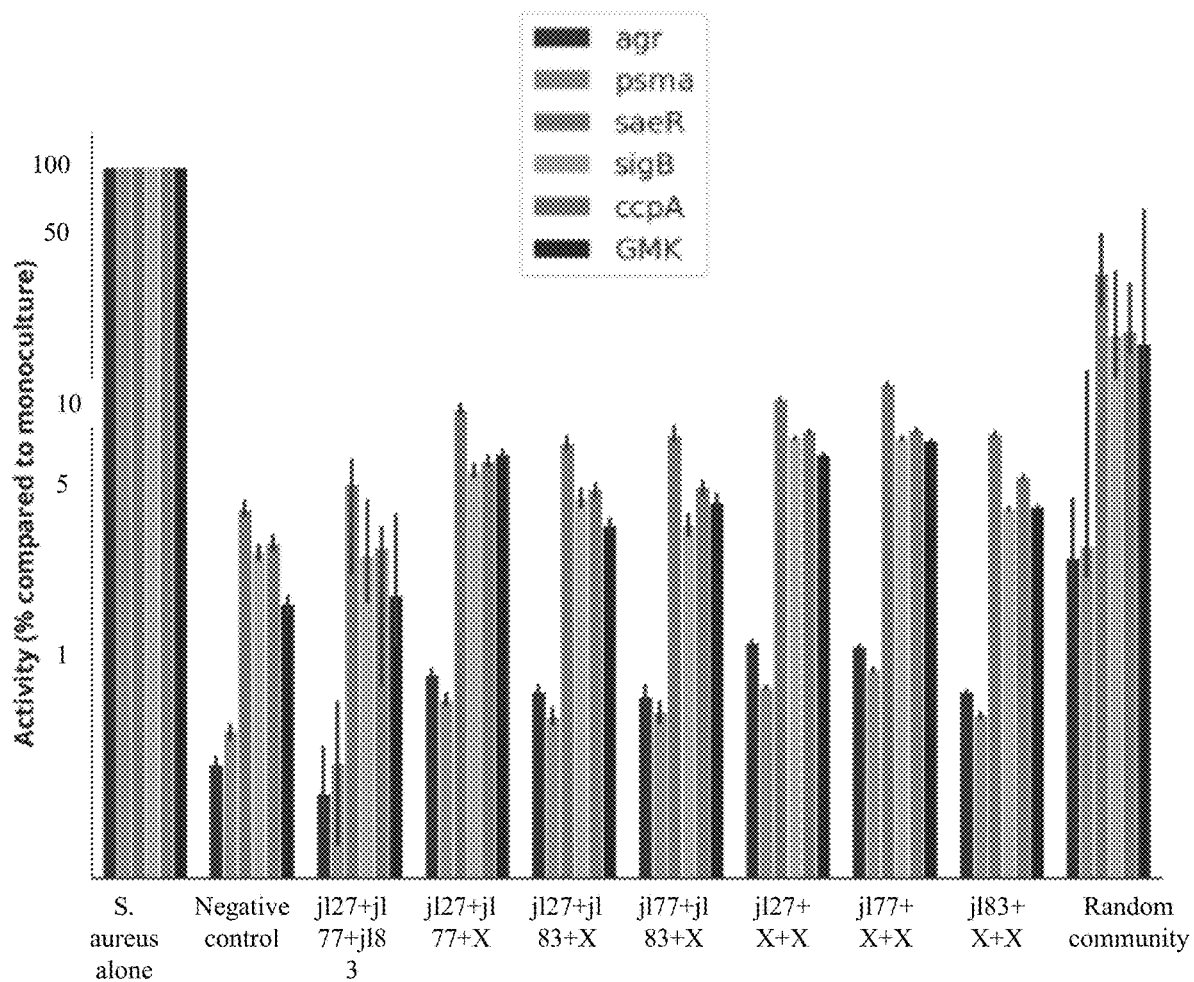
FIG. 2, is a bar graph that plots percent activity of *S. aureus* gene expression by a fluorescent reporter. The X-axis shows the strains in the combinatorial screening assay. The Y-axis shows the percent activity (from 0-100%) as compared to the *S. aureus* monoculture.

Referring to FIG. 2, the Y-axis shows the percent activity as compared to the *S. aureus* monoculture. The X-axis shows the strains in the combinatorial screening assay. "X" with one or more strains indicates all individual strains from the top 28 isolates were added to the mixture and the average is shown from the mixtures. For example, the jl27+jl77+X data is an average of 26 different 3-wise compositions. In another example, the jl27+X+X is an average of 351 different compositions. The random community is a 3 isolate community randomly selected from the top 28 isolates. The reporters are shown from left to right and are as follows: agr, psmA, saeR, sigB, ccpA and GMK. Three-wise combinations containing Strain jl.83, Strain jl.27 and Strain jl.77 were effective at suppressing *S. aureus* agr (quorum sensing) and psmA (toxin production); pairs of these were stronger still; and all three together produced the strongest effect. In some conditions, three-wise combinations containing Strain jl.83, Strain jl.27 and Strain jl.77 were effective at suppressing *S. aureus* saeR, sigB, ccpA and GMK All three together decreased activity of all reporters to less than 10% activity compared to monoculture. The decrease was unexpected as compared to a random community which only decreased expression levels to about 20% to 40% in saeR, sigB, ccpA and GMK as compared to the monoculture. The data shows strain combinations can be effective at inhibiting *S. aureus* gene expression.

Figure 3:
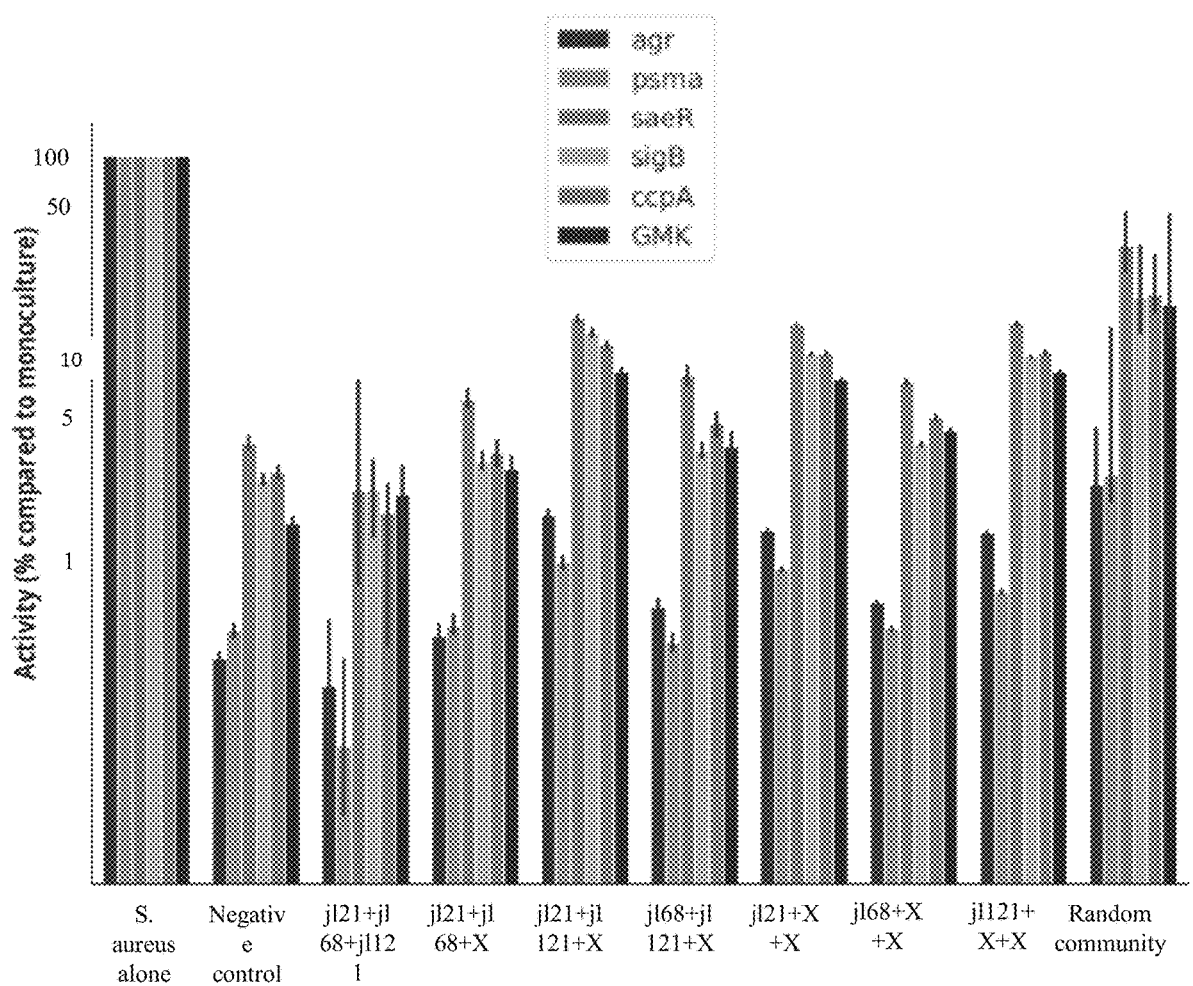
FIG. 3, is a bar graph that plots percent activity of *S. aureus* gene expression by a fluorescent reporter. The X-axis shows the strains in the combinatorial screening assay. The Y-axis shows the percent activity (from 0-100%) as compared to the *S. aureus* monoculture.

Referring to FIG. 3, the Y-axis shows the percent activity as compared to the *S. aureus* monoculture. The X-axis shows the strains in the combinatorial screening assay. "X" with one or more strains indicates all individual strains from the top 28 isolates were added to the mixture and the average is shown from the mixtures. For example, the jl21+jl68+X data is an average of 26 different 3-wise compositions. In another example, the jl21+X+X is an average of 351 different compositions. The random community is a 3 isolate community randomly selected from the top 28 isolates. The reporters are shown from left to right and are as follows: agr, psmA, saeR, sigB, ccpA and GMK. Three-wise combinations containing Strain jl.21, Strain jl.68, and Strain jl.121 were effective at suppressing *S. aureus* agr (quorum sensing) and psmA (toxin production); pairs of these were stronger still; and all three together produced the strongest effect. In some conditions, three-wise combinations containing Strain jl.21, Strain jl.68, and Strain jl.121 were effective at suppressing *S. aureus* saeR, sigB, ccpA and GMK. All three together decreased activity of all reporters to less than 10% activity compared to monoculture. The decrease was unexpected as compared to a random community which only decreased expression levels to about 20% to 40% in saeR, sigB, ccpA and GMK as compared to the monoculture. The data shows strain combinations can be effective at inhibiting *S. aureus* gene expression.

Figure 4:
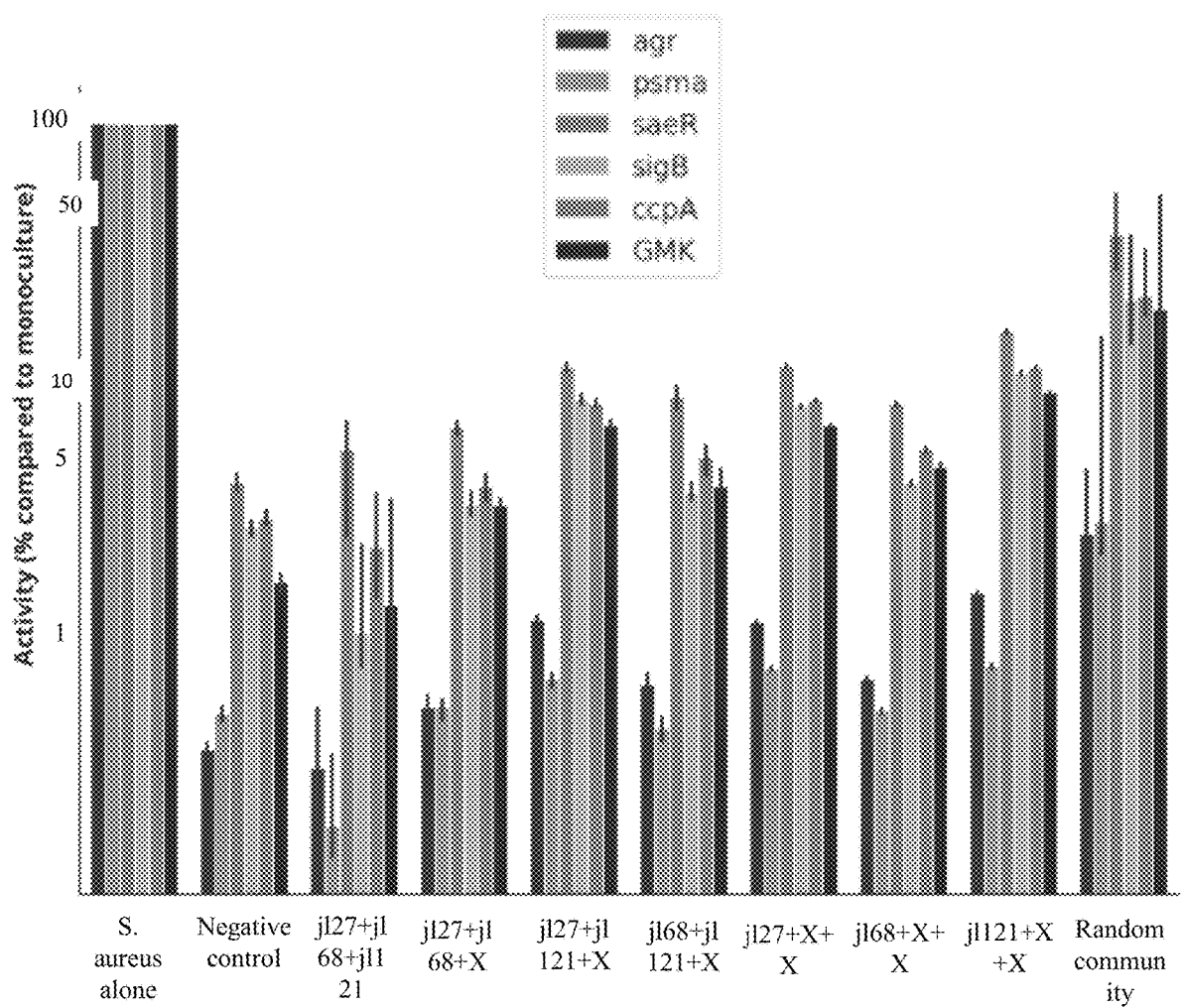
FIG. 4, is a bar graph that plots percent activity of *S. aureus* gene expression by a fluorescent reporter. The X-axis shows the strains in the combinatorial screening assay. The Y-axis shows the percent activity (from 0-100%) as compared to the *S. aureus* monoculture.

Referring to FIG. 4, the Y-axis shows the percent activity as compared to the *S. aureus* monoculture. The X-axis shows the strains in the combinatorial screening assay. "X" with one or more strains indicates all individual strains from the top 28 isolates were added to the mixture and the average is shown from the mixtures. For example, the jl27+jl68+X data is an average of 26 different 3-wise compositions. In another example, the jl27+X+X is an average of 351 different compositions. The random community is a 3 isolate community randomly selected from the top 28 isolates. The reporters are shown from left to right and are as follows: agr, psmA, saeR, sigB, ccpA and GMK. Three-wise combinations containing Strain jl.27, Strain jl.68, and Strain jl.121 were effective at suppressing *S. aureus* agr (quorum sensing) and psmA (toxin production); pairs of these were stronger still; and all three together produced the strongest effect. In some conditions, three-wise combinations containing Strain jl.27, Strain jl.68, and Strain jl.121 were effective at suppressing *S. aureus* saeR, sigB, ccpA and GMK All three together decreased activity of all reporters to less than 10% activity compared to monoculture. The decrease was unexpected as compared to a random community which only decreased expression levels to about 20% to 40% in saeR, sigB, ccpA and GMK as compared to the monoculture. The data shows strain combinations can be effective at inhibiting *S. aureus* gene expression.

Example 4: Assays of *S. aureus* Gene Expression Inhibition in Different Environmental Conditions Three wise combinations of Strain jl.83, Strain jl.27 Strain jl.77 Strain jl.21, Strain jl.68, and Strain jl.121 were screened in an assessment of the behavior of *S. aureus* when an additional environmental component such as a nutrient was added to the mixture. *S. aureus* behaviors were measured via a set of plasmid-mediated "promoter-reporter" strains, whose fluorescence report on one specific activity. Combinations of strains and environmental conditions were screened in an array for 1 day. The strain mixture conditions were: 1) a *S. aureus* monoculture, and 2) *S. aureus* mixed with three skin isolates. The screen analyzed the expression of the reporters agr for quorum sensing induction, psmA for toxin that damages host tissue, and GMK for constitutive metabolic function.

Figure 5:
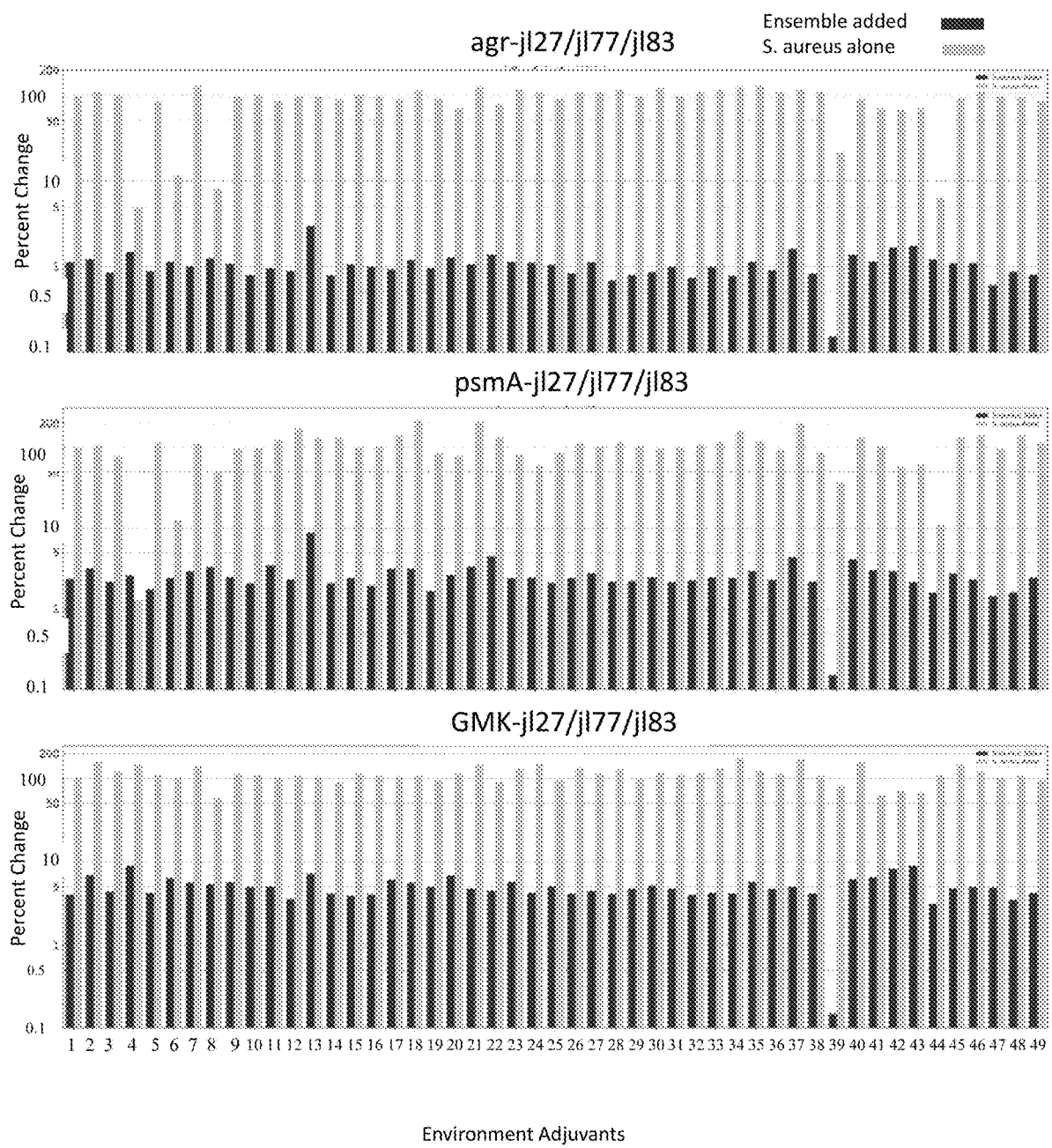
FIG. 5, is a bar graph that plots percent change of *S. aureus* gene expression by a fluorescent reporter in the three-strain mixture of Strain jl.83, Strain jl.27 and Strain jl.77 as compared to *S. aureus* monoculture in different environmental conditions. The Y-axis shows the percent change as compared to the *S. aureus* monoculture. The X-axis shows the environmental condition that was tested.

Referring to FIG. 5, the Y-axis shows the percent change as compared to the *S. aureus* monoculture. The monoculture conditions are shown with the gray bars and the black bars show the conditions in which Strain jl.83, Strain jl.27 and Strain jl.77 were added to the culture. The X-axis shows the environmental condition that was tested. The conditions are from left to right (1) base medium, then base medium supplemented with one of the following: (2) acetate, (3) beta-alanine, (4) bicarbonate, (5) biotin, (6) butyrate, (7) caffeine, (8) citrate, (9) creatine, (10) D-cellobiose, (11) D-fructose, (12) D-glucosamine, (13) D-glucose, (14) D-mannitol, (15) D-raffinose, (16) D-sorbitol, (17) D-sucrose, (18) D-trehalose, (19) D-xylose, (20) formate, (21) GlcNAc, (22) glycerol, (23) glycine, (24) L-alanine, (25) L-arabinose, (26) L-arginine, (27) L-citrulline, (28) L-glutamine, (29) L-hydroxyproline, (30) L-isoleucine, (31) L-leucine, (32) L-methionine, (33) L-ornithine, (34) L-proline, (35) L-serine, (36) L-taurine, (37) L-threonine, (38) L-valine, (39) L-ascorbate, (40) L-lactate, (41) nicotinamine, (42) polysorbate 20, (43) polysorbate 80, (44) propionate, (45) pyruvate, (46) succinate, (47) thiamine, (48) triethanolamine, or (49) urea. The data shows the strain combination containing Strain jl.83, Strain jl.27 and Strain jl.77 were effective at suppressing *S. aureus* agr (quorum sensing), psmA (toxin production), and GMK (metabolic function) in all tested environmental conditions, including conditions that aided *S. aureus* growth.

Figure 6:
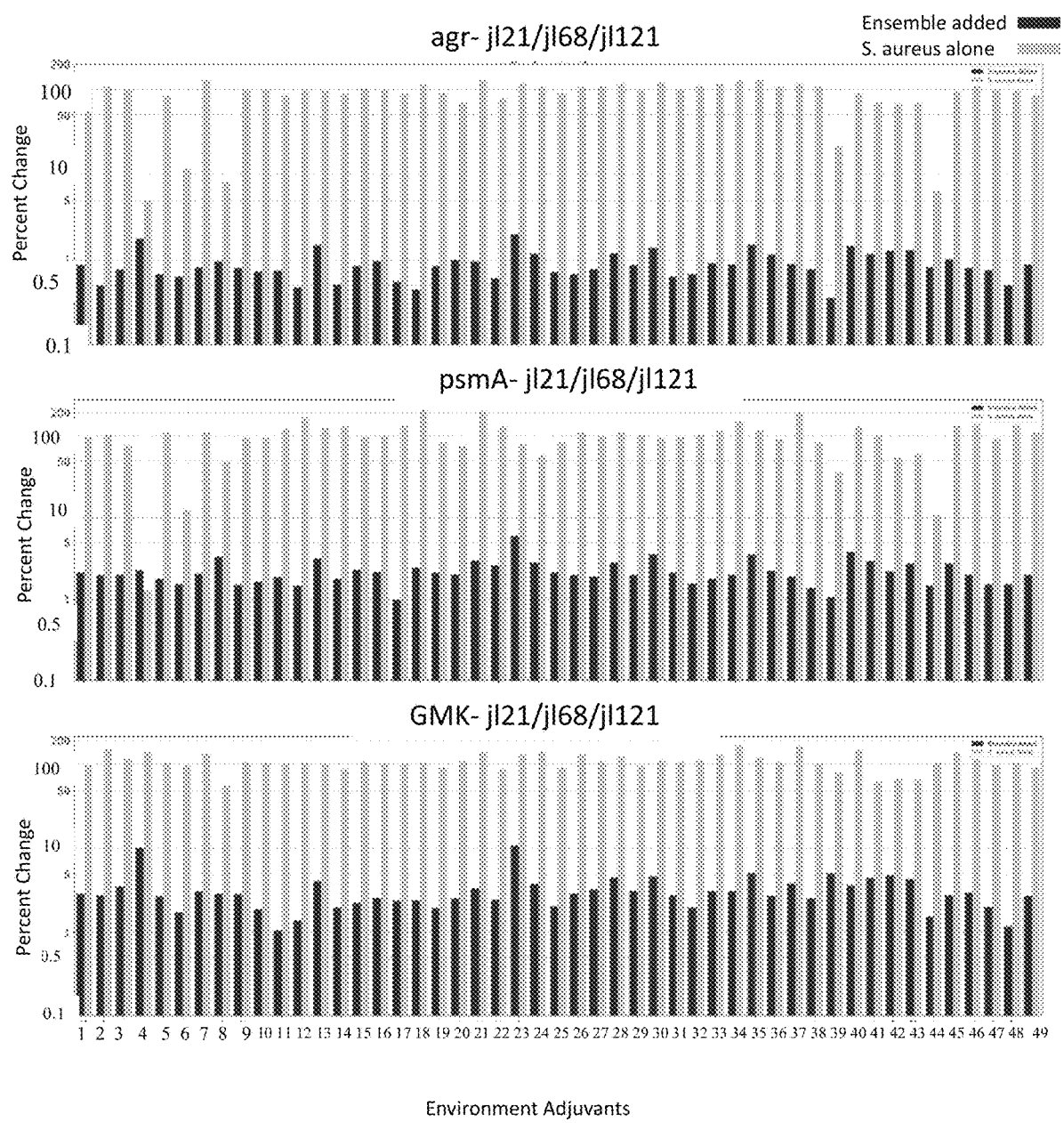
FIG. 6 is a bar graph that plots percent change of *S. aureus* gene expression by a fluorescent reporter in the three-strain mixture of Strain jl.21, Strain jl.68, and Strain jl.121 as compared to *S. aureus* monoculture in different environmental conditions. The Y-axis shows the percent change as compared to the *S. aureus* monoculture. The X-axis shows the environmental condition that was tested.

Referring to FIG. 6, the Y-axis shows the percent change as compared to the *S. aureus* monoculture. The monoculture conditions are shown with the gray bars and the black bars show the conditions in which Strain jl.21, Strain jl.68, and Strain jl.121 were added to the culture. The X-axis shows the environmental condition that was tested. The conditions are from left to right (1) base medium, then base medium supplemented with one of the following: (2) acetate, (3) beta-alanine, (4) bicarbonate, (5) biotin, (6) butyrate, (7) caffeine, (8) citrate, (9) creatine, (10) D-cellobiose, (11) D-fructose, (12) D-glucosamine, (13) D-glucose, (14) D-mannitol, (15) D-raffinose, (16) D-sorbitol, (17) D-sucrose, (18) D-trehalose, (19) D-xylose, (20) formate, (21) GlcNAc, (22) glycerol, (23) glycine, (24) L-alanine, (25) L-arabinose, (26) L-arginine, (27) L-citrulline, (28) L-glutamine, (29) L-hydroxyproline, (30) L-isoleucine, (31) L-leucine, (32) L-methionine, (33) L-orithine, (34) L-proline, (35) L-serine, (36) L-taurine, (37) L-threonine, (38) L-valine, (39) L-ascorbate, (40) L-lactate, (41) nicotinamine, (42) polysorbate 20, (43) polysorbate 80, (44) propionate, (45) pyruvate, (46) succinate, (47) thiamine, (48) triethanolamine, or (49) urea. In all cases, the strain combination was able to decrease expression of all three reporters to less than 10% monoculture levels. The data shows the strain combination containing Strain jl.21, Strain jl.68, and Strain jl.121 were effective at suppressing *S. aureus* agr (quorum sensing), psmA (toxin production), and GMK (metabolic function) in all tested environmental conditions, including conditions that aided *S. aureus* growth. In all cases, the strain combination was able to decrease expression of all three reporters to less than 10% monoculture levels.

Figure 7:
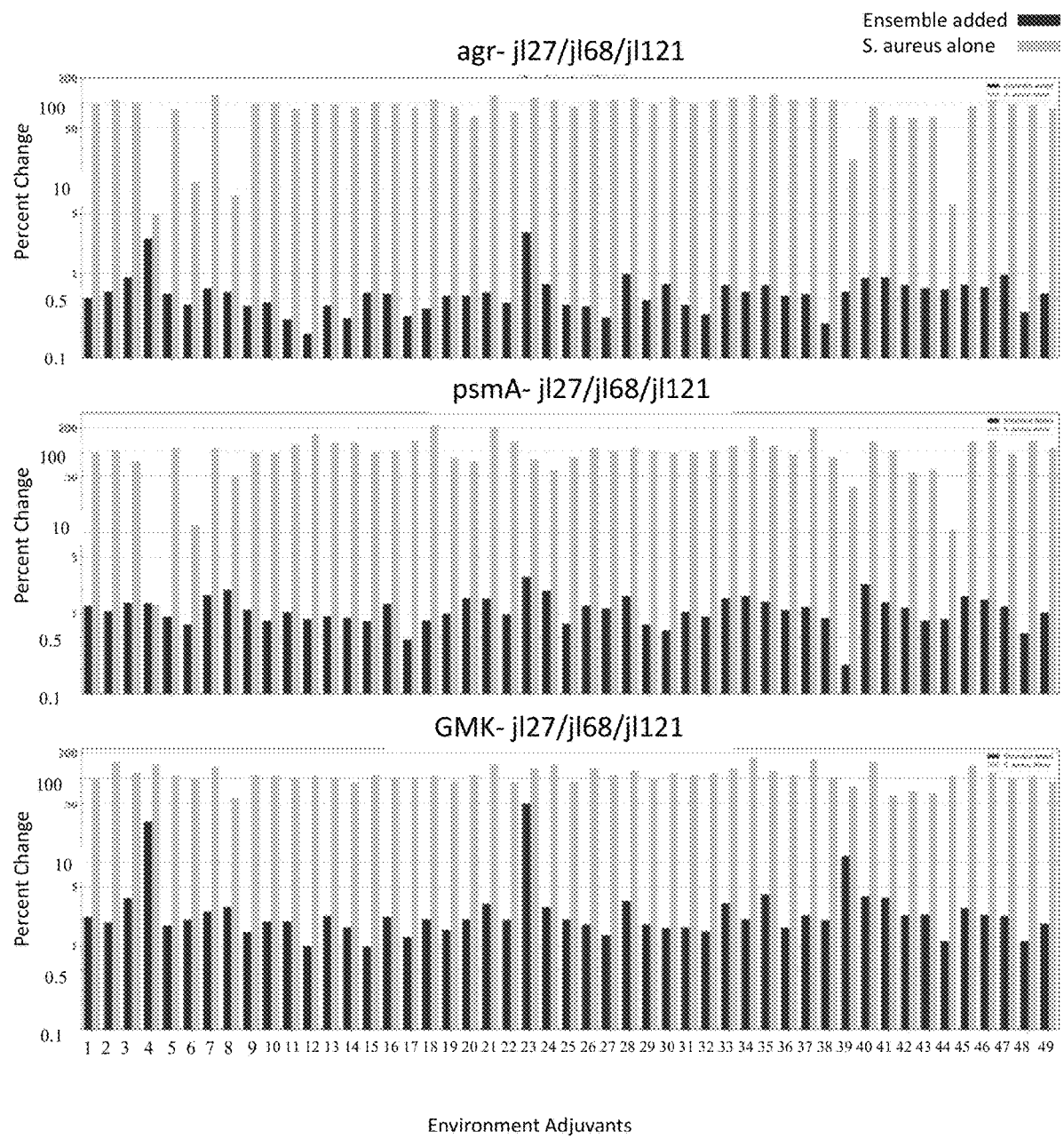
FIG. 7, is a bar graph that plots percent change of *S. aureus* gene expression by a fluorescent reporter in the three-strain mixture of Strain jl.27, Strain jl.68, and Strain jl.121 as compared to *S. aureus* monoculture in different environmental conditions. The Y-axis shows the percent change as compared to the *S. aureus* monoculture. The X-axis shows the environmental condition that was tested.

Referring to FIG. 7, the Y-axis shows the percent change as compared to the *S. aureus* monoculture. The monoculture conditions are shown with the gray bars and the black bars show the conditions in which Strain jl.27, Strain jl.68, and Strain jl.121 were added to the culture. The X-axis shows the environmental condition that was tested. The conditions are from left to right (1) base medium, then base medium supplemented with one of the following: (2) acetate, (3) beta-alanine, (4) bicarbonate, (5) biotin, (6) butyrate, (7) caffeine, (8) citrate, (9) creatine, (10) D-cellobiose, (11) D-fructose, (12) D-glucosamine, (13) D-glucose, (14) D-mannitol, (15) D-raffinose, (16) D-sorbitol, (17) D-sucrose, (18) D-trehalose, (19) D-xylose, (20) formate, (21) GlcNAc, (22) glycerol, (23) glycine, (24) L-alanine, (25) L-arabinose, (26) L-arginine, (27) L-citrulline, (28) L-glutamine, (29) L-hydroxyproline, (30) L-isoleucine, (31) L-leucine, (32) L-methionine, (33) L-ornithine, (34) L-proline, (35) L-serine, (36) L-taurine, (37) L-threonine, (38) L-valine, (39) L-ascorbate, (40) L-lactate, (41) nicotinamine, (42) polysorbate 20, (43) polysorbate 80, (44) propionate, (45) pyruvate, (46) succinate, (47) thiamine, (48) triethanolamine, or (49) urea. In all cases, the strain combination was able to decrease expression of all three reporters to less than about 50% monoculture levels. The data shows the strain combination containing Strain jl.27, Strain jl.68, and Strain jl.121 were effective at suppressing *S. aureus* agr (quorum sensing), psmA (toxin production), and GMK (metabolic function) in all tested environmental conditions, including conditions that aided *S. aureus* growth.

Figure 8:
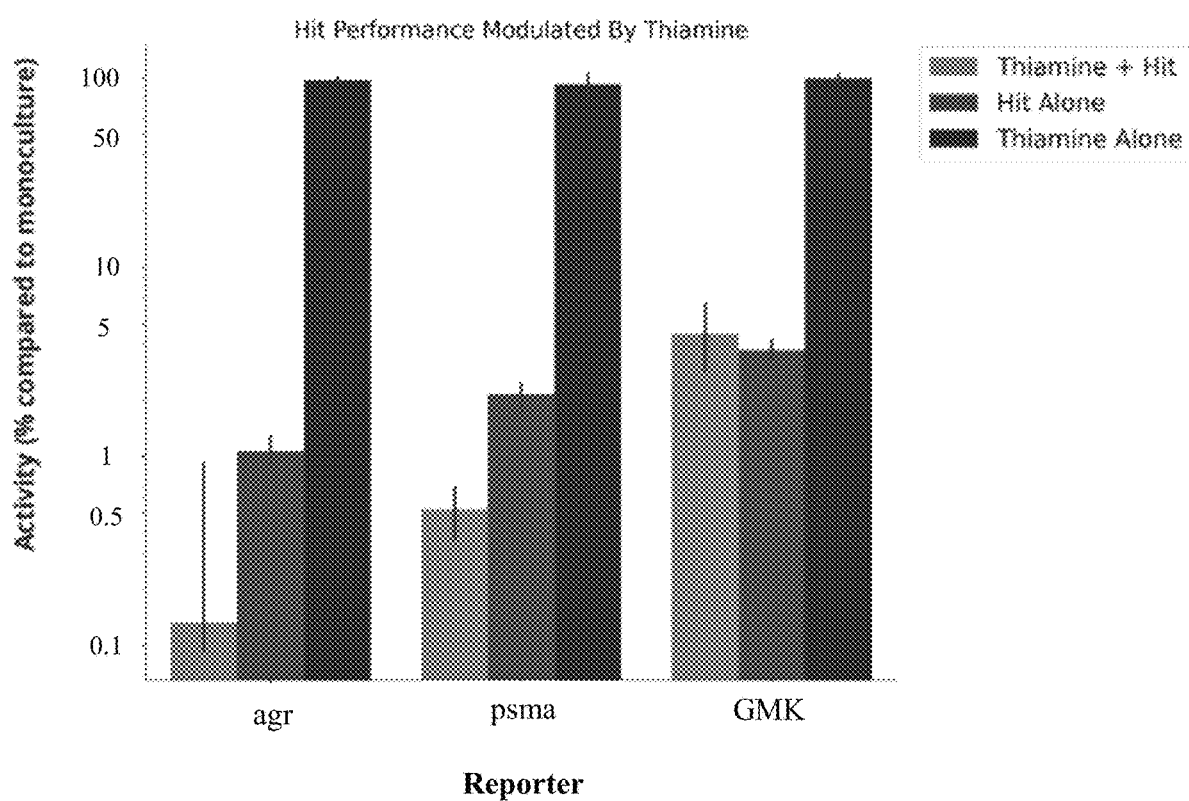
FIG. 8, is a bar graph that plots percent activity of *S. aureus* gene expression by a fluorescent reporter in different growth conditions. The Y-axis shows the percent activity as compared to the *S. aureus* monoculture. The X-axis shows the expression of *S. aureus* agr (quorum sensing), psmA (toxin production), and GMK (metabolic function).

Example 5: Assay of Thiamine Enhancement of *S. aureus* Gene Expression Inhibition Strain jl.83, Strain jl.27 and Strain jl.77 were screened in an assessment of the behavior of *S. aureus* when thiamine was added to the mixture. *S. aureus* behaviors were measured via a set of plasmid-mediated "promoter-reporter" strains, whose fluorescence report on one specific activity. Combinations of strains and environmental conditions were screened in an array assay for 1 day. The strain mixture conditions were: (1) a *S. aureus* monoculture, (2) *S. aureus* monoculture in medium with excess thiamine, (3) *S. aureus* mixed with Strain jl.83, Strain jl.27 and Strain jl.77 and (4) *S. aureus* mixed with Strain jl.83, Strain jl.27 and Strain jl.77 in medium with excess thiamine. The array assay analyzed the expression of the reporters agr for quorum sensing induction, psmA for toxin that damages host tissue, and GMK for constitutive metabolic function. Referring to FIG. 8, the Y-axis shows the percent activity as compared to the *S. aureus* monoculture. The X-axis shows the expression of *S. aureus* agr (quorum sensing), psmA (toxin production), and GMK (metabolic function). For each gene, three strain mixture conditions are shown from left to right the conditions are: condition (4), condition (3), and condition (2). The addition of thymine surprisingly showed a synergistic effect when added with Strain jl.83, Strain jl.27 and Strain jl.77 in suppressing the expression of *S. aureus* agr (quorum sensing), and psmA (toxin production). For example, agr expression and psmA expression was decreased greater than 2-fold in both cases. This data shows thymine displayed a synergistic effect with the mixture of bacteria to increase *S. aureus* gene inhibition.

Example 6: Isolated Strains Growth in Animal-Free Media

Figure 9:
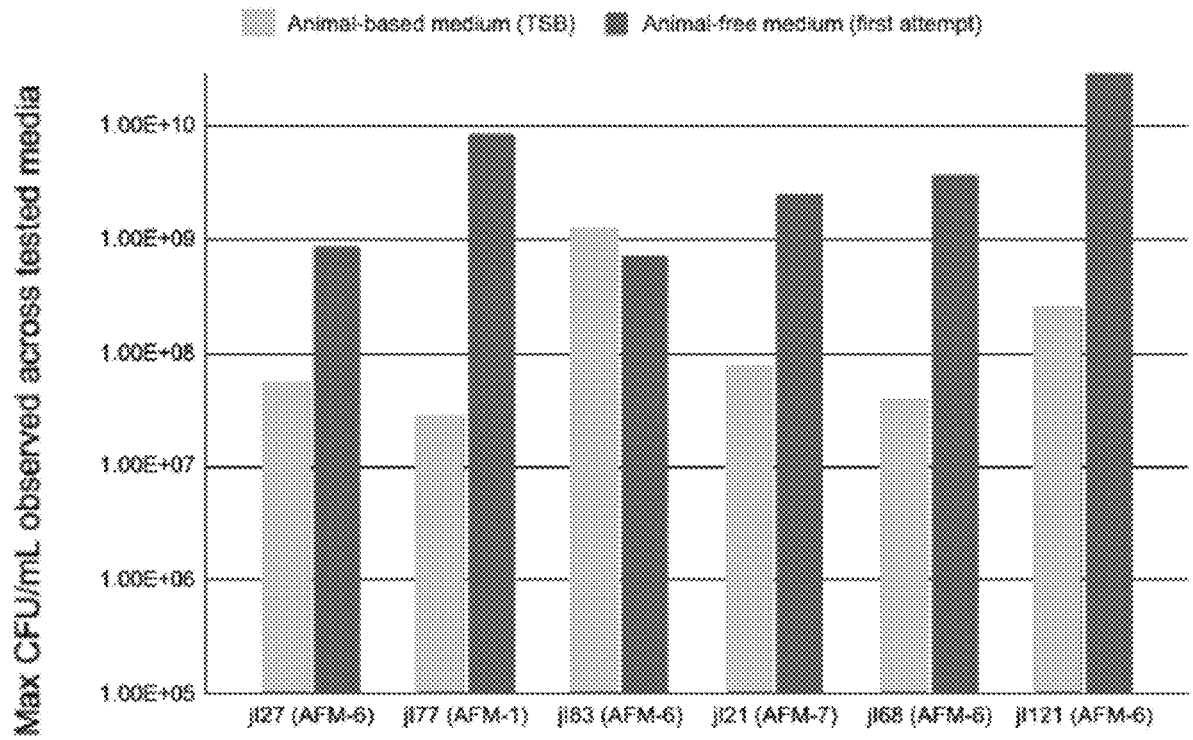
FIG. 9, is a bar graph that plots max colony-forming unit (cfu)/ml of isolated strains in different media. The Y-axis shows the cfu/mL observed across the tested media. The X-axis indicates the strain tested and the animal-free media formulation used for the strain tested.

Bacterial isolates Strain jl.27, Strain jl.77, Strain jl.83, Strain jl.21, Strain jl.68, and Strain jl.121 were grown in comparable conditions in an animal based medium tryptic soy broth (TSB) and in various animal-free media (AFM). Strains were grown for 48 hours after inoculation with the same number of bacteria. Referring to FIG. 9, the Y-axis shows the colony-forming unit (cfu)/mL observed across the tested media. The X-axis indicates the strain tested and the animal-free media formulation used for the strain tested (e.g., AFM-6 for animal-free media formulation 6). The strains tested were Strain jl.27 (jl27), Strain jl.77 (jl77), Strain jl.83 (jl83), Strain jl.21 (jl21), Strain jl.68 (jl68), and Strain jl.121 (jl121). For most of the strains grown in animal-free media there was a 10-100× improvement in cultivation cfu/ml after 48 hours. The data shows the strains can be cultivated in a variety of media and can be manufactured in animal free media for production of a composition, such as a pharmaceutical composition.

Figure 10:
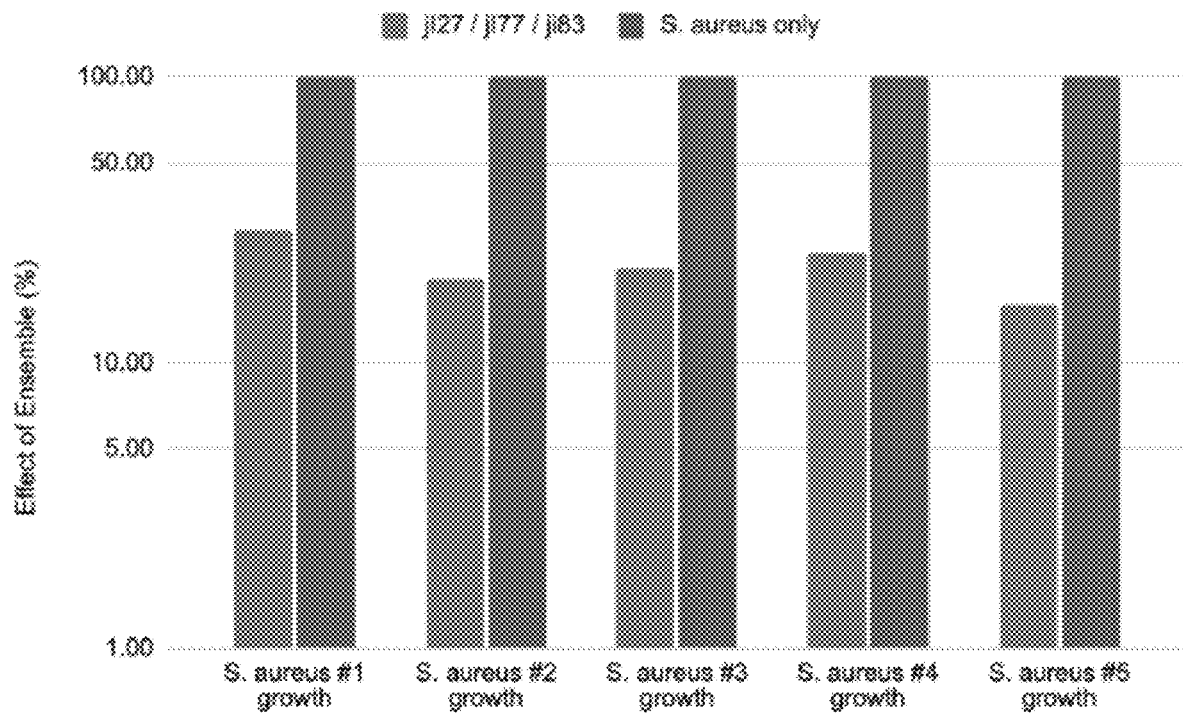
FIG. 10, is a bar graph that plots percent of growth of mixed cultures as compared to *S. aureus* monoculture. The Y-axis shows the effect of growth inhibition (%) by the strain combination. The X-axis shows the growth of different *S. aureus* strains in the presence of an ensemble (e.g., the three-strain combination) or the *S. aureus* strain alone.
Figure 11:
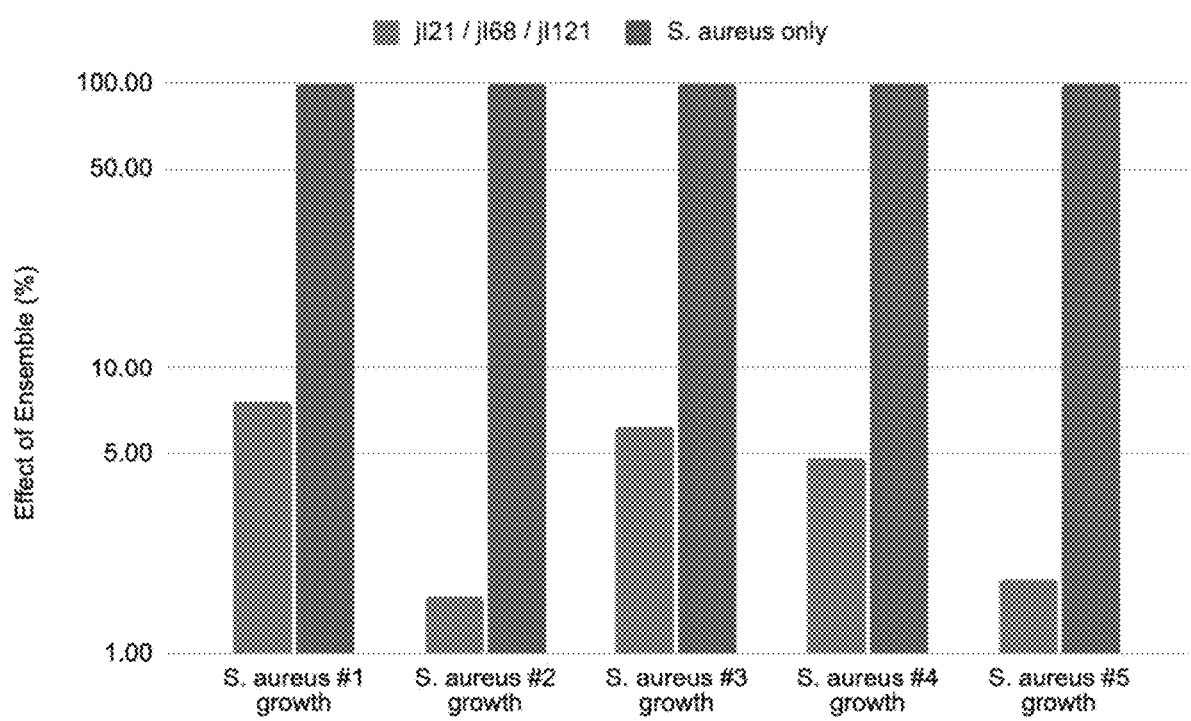
FIG. 11, is a bar graph that plots percent growth of mixed cultures as compared to *S. aureus* monoculture. The Y-axis shows the effect of growth inhibition (%) by the strain combination. The X-axis shows the growth of different *S. aureus* strains in the presence of an ensemble (e.g., the three-strain combination) or the *S. aureus* strain alone.
Figure 12:
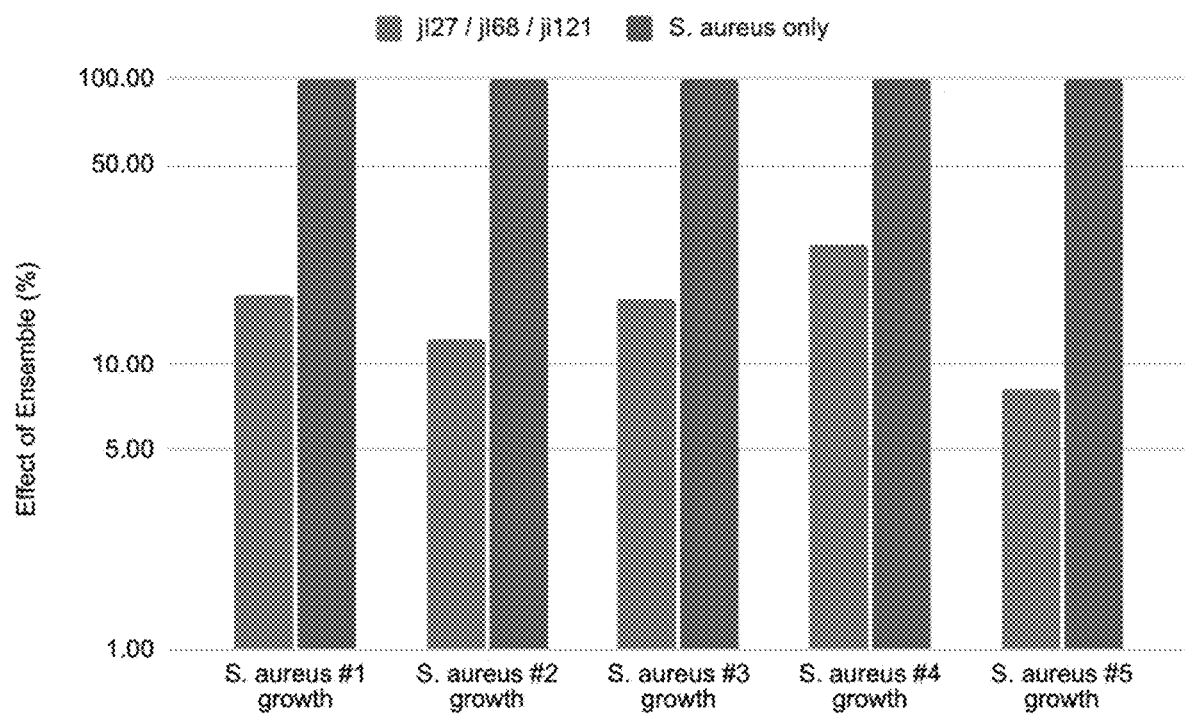
FIG. 12, is a bar graph that plots percent growth of mixed cultures as compared to *S. aureus* monoculture. The Y-axis shows the effect of growth inhibition (%) by the strain combination. The X-axis shows the growth of different *S. aureus* strains in the presence of an ensemble (e.g., the three-strain combination) or the *S. aureus* strain alone.

Example 7: Assays of S. aureus Growth Inhibition with Combinations of Bacterial Isolates Bacterial isolates from the skin of healthy individuals were tested for their ability to inhibit the growth of several S. aureus strains. Strains were grown for 48 hours after inoculation with the same number of bacteria. Referring to FIG. 10, FIG. 11 and FIG. 12, the Y-axis shows the effect of growth inhibition by the strain combination. The X-axis shows the growth of different S. aureus strains in the presence of an ensemble (e.g., the three-strain combination) or the S. aureus strain alone. For the S. aureus strain tested, the ensemble is the left bar graph and the S. aureus strain alone is the right bar graph. FIG. 10 tested the ensemble jl27/jl77/jl83 (Strain jl.27, Strain jl.77 and Strain jl.83), FIG. 11 tested the ensemble jl21/jl68/jl121 (Strain jl.21, Strain jl.68, and Strain jl.121), FIG. 12 tested the ensemble jl27/jl68/jl121 (Strain jl.27, Strain jl.68, and Strain jl.121). All three tested strain combinations were able to inhibit growth of different S. aureus strains. This suggests the strain combinations are effective against a wide variety of S. aureus strains.

Figure 13:
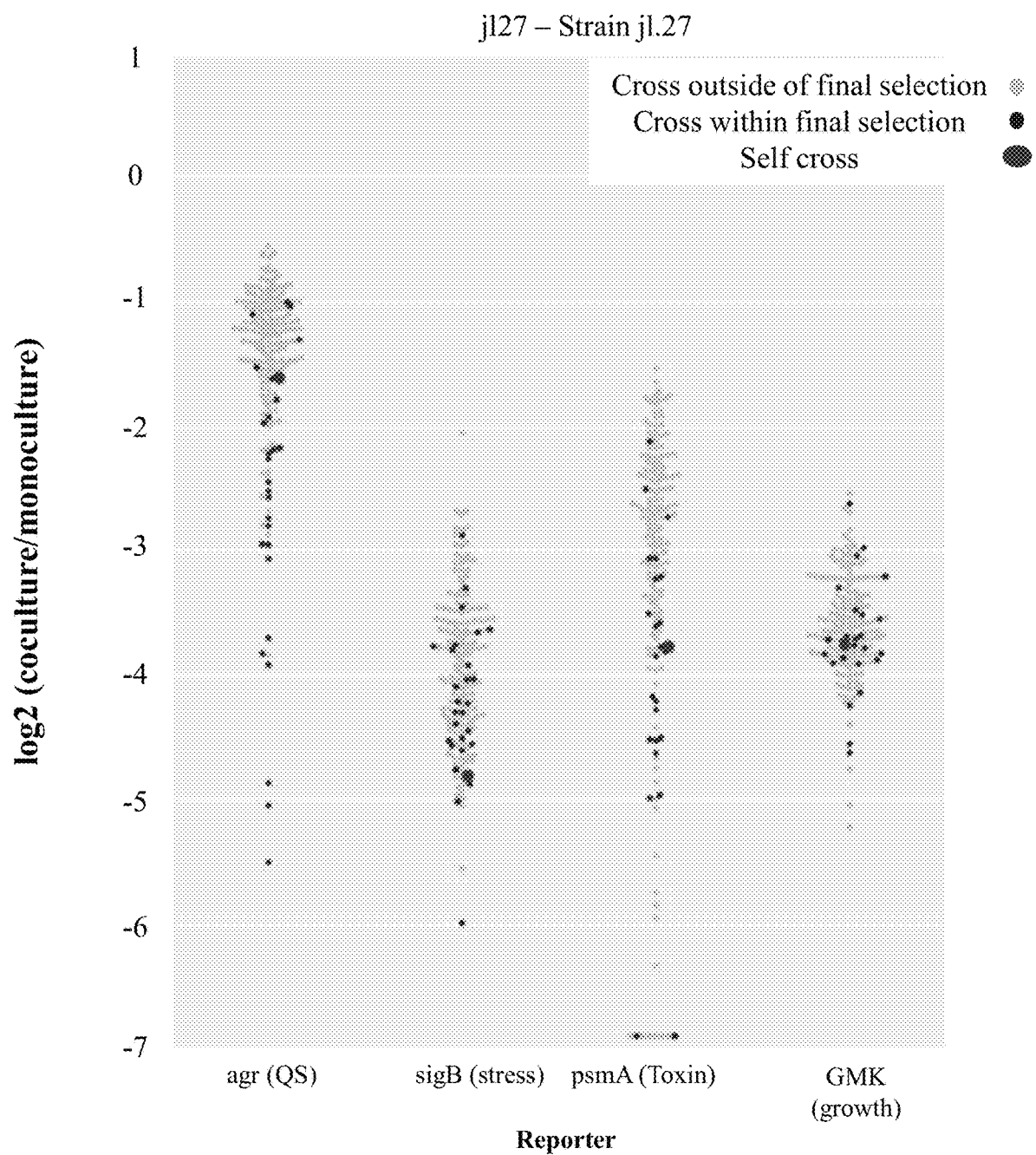
FIG. 13, is a data plot that plots the log 2 (coculture/monoculture) change of *S. aureus* gene expression by a fluorescent reporter in different mixtures with Strain jl.27. The Y-axis shows the log 2 expression change of the coculture/a *S. aureus* promoter-reporter monoculture. The X-axis shows the gene promoters tested.

Example 8: Assays of S. aureus Gene Expression Inhibition with Bacillus Wiedmannii Alone and in Combination with Additional Strains Strain jl.27 was isolated from the skin of a healthy individual and was screened in a pair-wise combinatorial screening assay against 4 S. aureus behavior reporters. S. aureus behaviors were measured via a set of plasmid-mediated "promoter-reporter" S. aureus strains, whose fluorescence report on one specific activity. Combinations of strains were screened in an array assay. The strain mixture conditions were: 1) Strain jl.27 self-cross, 2) Strain jl.27 with random skin isolate, and 3) Strain jl.27 with another isolate that showed inhibition of S. aureus gene expression. The screen analyzed the expression of the reporters agr for quorum sensing induction, sigB for the stress response sigma factor, psmA for toxin that damages host tissue, and GMK for constitutive metabolic function. Referring to FIG. 13, the Y-axis shows the log 2 expression change of the coculture/a S. aureus promoter-reporter monoculture. The X-axis shows the gene promoters tested. The big circles indicate the data points for the self-cross (Strain jl.27 and Strain jl.27). The small black circles indicate Strain jl.27 crossed with another isolate that showed inhibition of S. aureus gene expression. The small light gray circles indicate Strain jl.27 with random skin isolate. The data shows Strain jl.27 had a strong suppressive effect on growth, stress, and toxin production of S. aureus. It also appeared in many combinations where quorum sensing was strongly suppressed in S. aureus. This data shows Strain jl.27 is effective alone or in combination at inhibiting S. aureus gene expression.

Example 9: Inhibition of S. aureus Gene Expression in the Presence of Additional Microbes Three wise combination, two wise combinations and individual strains of Strain jl.83, Strain jl.27 Strain jl.77 Strain jl.21, Strain jl.68, and Strain jl.121 were screened in an assessment of the behavior of S. aureus when in the presence of different microbes. The bacterial strains added to the mixture were randomly selected from 92 strains selected from the original 609 frozen strain collection. S. aureus behaviors were measured via a set of plasmid-mediated "promoter-reporter" strains, whose fluorescence report on one specific activity. The screen analyzed the expression of the reporters: agr for quorum sensing induction, psmA for toxin that damages host tissue, and GMK for constitutive metabolic function. Combinations of strains were screened in an array after 1 day of growth. The strain mixture conditions were: 1) three-wise combination with an additional set of 4 strains, 2) two-wise combination with an additional set of 5 strains, and 3) one individual strain with an additional set up 6 strains. For example, jl121/jl21/jl68+4X shows tested communities where jl.121, jl.21 and jl.68 and up to 4 additional microbes (chosen among 89 strains) were present. In another example, jl121/jl21+5X shows tested communities where jl.121 and jl.21 and up to 5 additional microbes (chosen among 90 strains) were present. In another example, jl121+6X shows tested communities where jl.121 and up to 6 additional microbes (chosen among 91 strains) were present.

Figure 14:
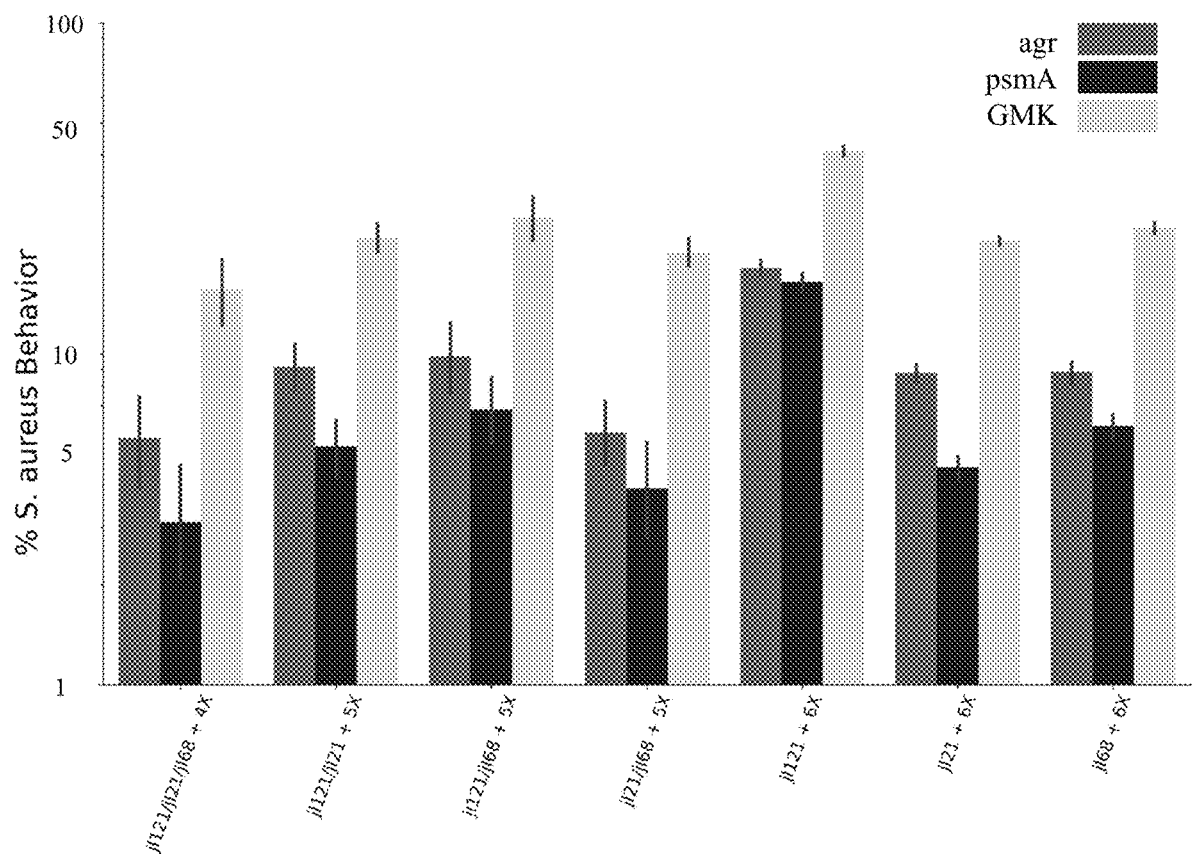
FIG. 14, is a bar graph that plots the percent *S. aureus* behavior (i.e. expression) of *S. aureus* genes by fluorescent reporters of agr, psmA, and GMK. The expression plotted is shown as compared to *S. aureus* monoculture expression of the reporters. Different strain combinations of Strain jl.121, Strain jl.21, and Strain jl.68 were tested in the presence of up to 7 microbe communities for their ability to reduce *S. aureus* gene expression. The Y-axis shows the percent expression of the reporter as compared to the *S. aureus* monoculture. The X-axis shows the strain combinations that were tested. The data shows the 3-species combination of Strain jl.121, Strain jl.21, and Strain jl.68 was typically more robust at reducing gene expression than their subsets (e.g., a single strain or two strain combination), and were able to reduce *S. aureus* gene expression in the presence of additional microbes.

Referring to FIG. 14, the Y-axis shows the percent expression of the reporter as compared to the S. aureus monoculture (i.e., the monoculture is 100%). The X-axis shows the strain combinations that were tested. The tested strains were Strain jl.121, Strain jl.21, and Strain jl.68. These strains were tested in different combinations with a random selection of strains to form 7-strain communities. The data shows the strain combination containing Strain jl.121, Strain jl.21, and Strain jl.68 were (1) effective at suppressing S. aureus agr (quorum sensing), psmA (toxin production), and GMK (metabolic function); (2) strong performance of the strain combination (ensemble) still occurs even with other microbes present, suggesting the combination will perform well in a native microbiome; and (3) that performance is stronger than when any subset of the 3-species combination is present. For example, a 3-species combination of Strain jl.121, Strain jl.21, and Strain jl.68 are robust to the larger community and more robust than their subsets as agr expression was reduced to less than about 5%, psmA expression was reduced to less than about 2%, and GMK expression was reduced to less than about 20%.

Figure 15:
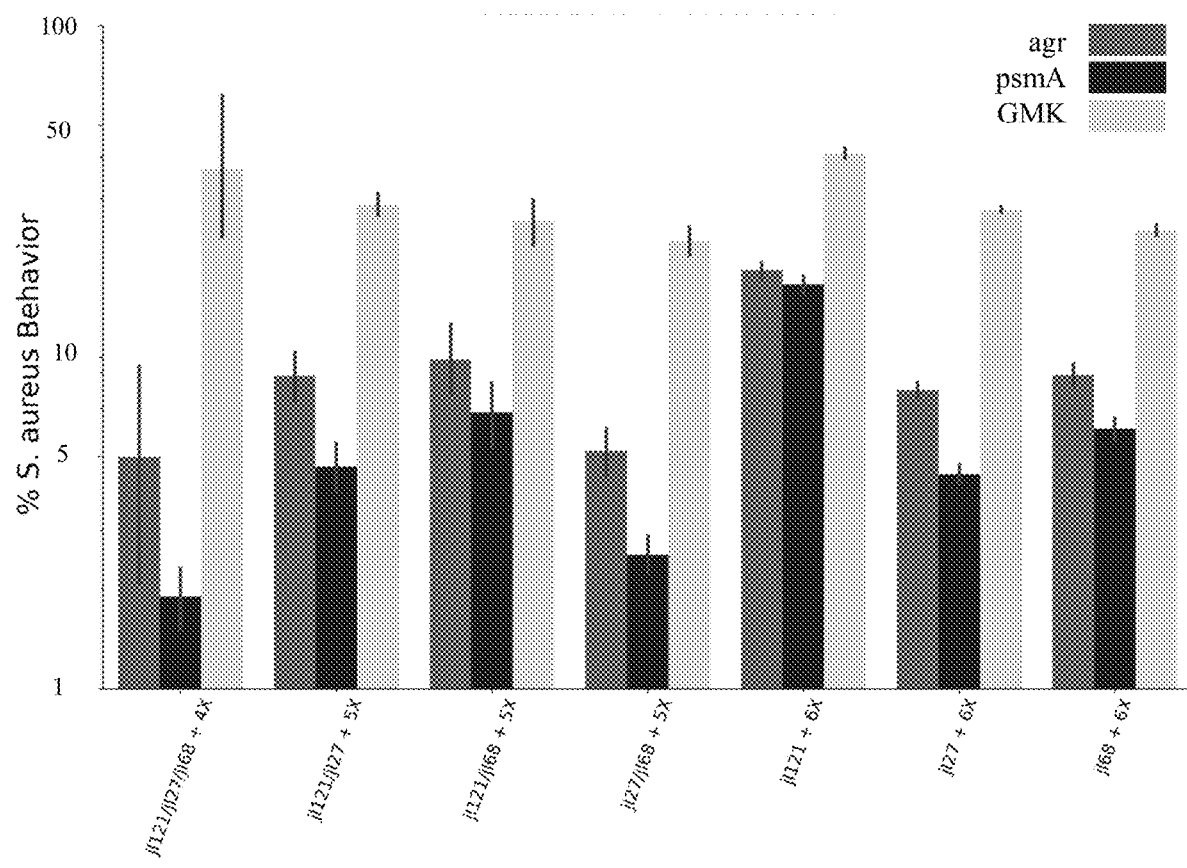
FIG. 15, is a bar graph that plots the percent *S. aureus* behavior (i.e. expression) of *S. aureus* genes by fluorescent reporters of agr, psmA, and GMK. The expression plotted is shown as compared to *S. aureus* monoculture expression of the reporters. Different strain combinations of Strain jl.121, Strain jl.27, and Strain jl.68 were tested in the presence of up to 7 microbe communities for their ability to reduce *S. aureus* gene expression. The Y-axis shows the percent expression of the reporter as compared to the *S. aureus* monoculture. The X-axis shows the strain combinations that were tested. The data shows the 3-species combination of Strain jl.121, Strain jl.27, and Strain jl.68 was typically more robust at reducing gene expression than their subsets (e.g., a single strain or two strain combination), and were able to reduce *S. aureus* gene expression in the presence of additional microbes.

Referring to FIG. 15, shows the percent expression of the reporter as compared to the S. aureus monoculture (i.e., the monoculture is 100%). The X-axis shows the strain combinations that were tested. The tested strains were Strain jl.121, Strain jl.27, and Strain jl.68. These strains were tested in different combinations with a random selection of strains to form 7-strain communities. The data shows the strain combination containing Strain jl.121, Strain jl.27, and Strain jl.68 were (1) effective at suppressing *S. aureus* agr (quorum sensing), psmA (toxin production), and GMK (metabolic function); (2) strong performance of the strain combination (ensemble) still occurs even with other microbes are present, suggesting the combination will perform well in a native microbiome; and (3) that performance is stronger than when any subset of the 3-species combination is present. For example, a 3-species combination of Strain jl.121, Strain jl.27, and Strain jl.68 are robust to the larger community and more robust than their subsets as agr expression was reduced to less than about 5%, psmA expression was reduced to less than about 2%, and GMK expression was reduced to less than about 40%.

Figure 16:
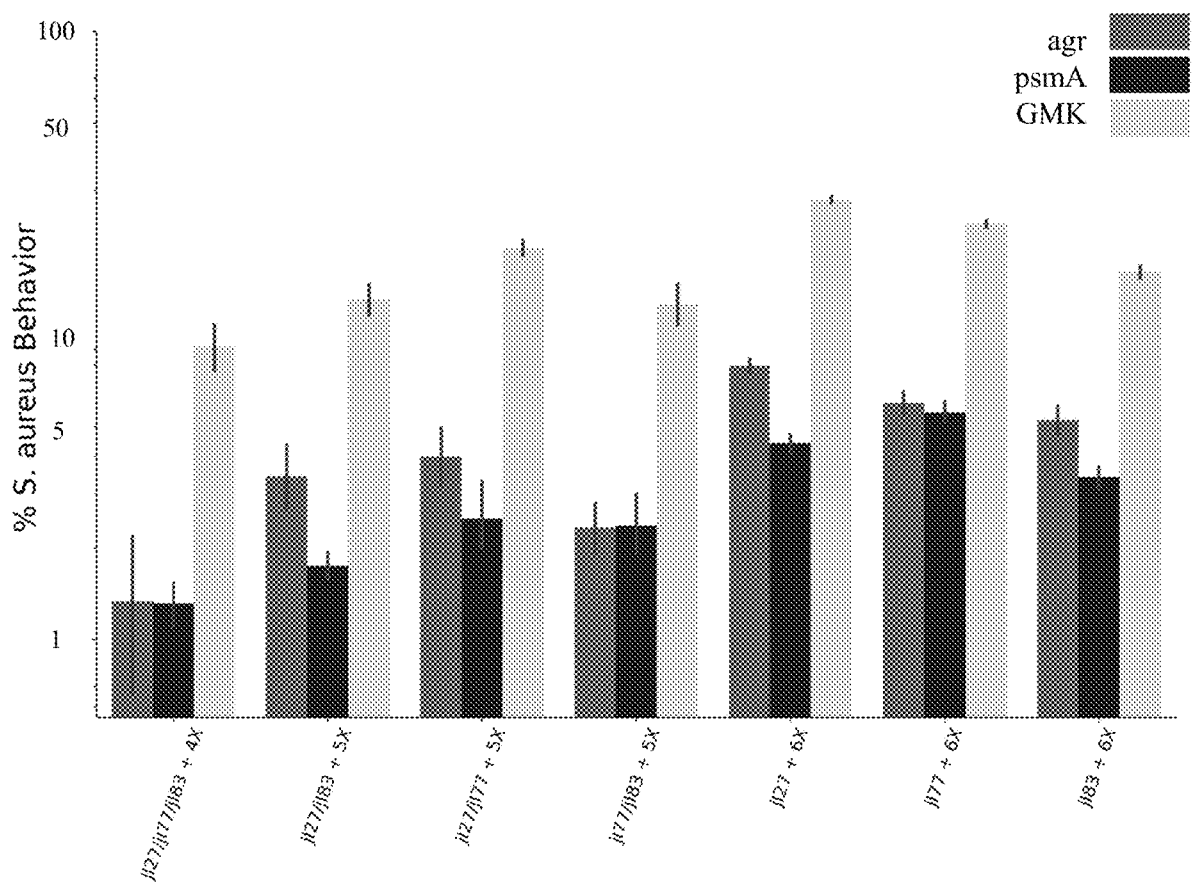
FIG. 16, is a bar graph that plots the percent *S. aureus* behavior (i.e. expression) of *S. aureus* genes by fluorescent reporters of agr, psmA, and GMK. The expression plotted is shown as compared to *S. aureus* monoculture expression of the reporters. Different strain combinations of Strain jl.27, Strain jl.77, and Strain jl.83 were tested in the presence of up to 7 microbe communities for their ability to reduce *S. aureus* gene expression. The Y-axis shows the percent expression of the reporter as compared to the *S. aureus* monoculture. The X-axis shows the strain combinations that were tested. The data shows the 3-species combination of Strain jl.27, Strain jl.77, and Strain jl.83 was typically more robust at reducing gene expression than their subsets (e.g., a single strain or two strain combination), and were able to reduce *S. aureus* gene expression in the presence of additional microbes.

Referring to FIG. 16, shows the percent expression of the reporter as compared to the *S. aureus* monoculture (i.e., the monoculture is 100%). The X-axis shows the strain combinations that were tested. The tested strains were Strain jl.27, Strain jl.77, and Strain jl.83. These strains were tested in different combinations with a random selection of strains to form 7-strain communities. The data shows the strain combination containing Strain jl.27, Strain jl.77, and Strain jl.83 were (1) effective at suppressing *S. aureus* agr (quorum sensing), psmA (toxin production), and GMK (metabolic function); (2) strong performance of the strain combination (ensemble) still occurs even with other microbes are present, suggesting the combination will perform well in a native microbiome; and (3) that performance is stronger than when any subset of the 3-species combination is present. For example, a 3-species combination of Strain jl.27, Strain jl.77, and Strain jl.83 are robust to the larger community and more robust than their subsets as agr expression was reduced to less than about 2%, psmA expression was reduced to less than about 2%, and GMK expression was reduced to less than about 10%.

Example 10: Clinical Study of Skin Inflammation

A human female subject diagnosed with inflammation of the skin is treated with a pharmaceutical composition comprising Strain jl.21, Strain jl.68, and Strain jl.121. After administration of the pharmaceutical composition for 2 weeks, the following is observed: an amount of pain, an amount of redness, an amount of swelling, and an amount of itching.

Example 11: Clinical Study of Atopic Dermatitis

A human male subject diagnosed with atopic dermatitis is treated with a pharmaceutical composition comprising Strain jl.83, Strain jl.27 and Strain jl.77. After administration of the pharmaceutical composition for 3 weeks, the following is observed: an amount of flakiness, an amount of redness, an amount of dryness, and an amount of peeling.

Example 12: Sequences of Isolated Strains

Isolated strains were subjected to whole genome sequencing and assembly of generated contigs. Additionally, 16s rRNA gene sequences were sequenced by Sanger sequencing and manually trimmed. The 16s rRNA sequences from the isolated strains are presented in Table 6. Additionally, several identifier sequences were pulled from the assembly for each isolated strain for identification. The identifier sequences from the isolated strains are presented in Table 7. To identify the identifier sequences, the genome assemblies were assessed for strain identifying sequences. The assemblies were preprocessed by: removing 1000 bp from each side of each assembly sequence to minimize edge effects and if the resulting sequence length after cropping was <10 kbp, it was dropped from consideration. A series of new subsequences was created by applying a sliding window of some length, with a 10% overlap across windows; a 5000 bp window with a 500 bp overlap was used and a 1200 bp window with a 120 bp overlap was used. The sequences were searched by BLAST from a nucleotide collection database (the Nucleotide Collection (nt) database) provided by The National Center for Biotechnology Information (NCBI) downloaded on Sep. 17, 2022. Identifier sequences that had BLAST sequences search results with greater than or equal to 99% query coverage and less than 98% sequence percent identity are included in Table 7.

TABLE 6

16s rRNA sequences of Isolated Strains

| Strain Name | 16s rRNA Sequence |
|---|---|
| Strain jl.27 SEQ ID NO: 1 | TCTTATGAAGTTAGCGGCGGACGGGTGAGTAACACGTGGGTAACCTGCCCATAAGA<br>CTGGGATAACTCCGGGAAACCGGGGCTAATACCGGATAACATTTTGAACCGCATGG<br>TTCGAAATTGAAAGGCGGCTTCGGCTGTCACTTATGGATGGACCCGCGTCGCATTA<br>GCTAGTTGGTGAGGTAACGGCTCACCAAGGCAACGATGCGTAGCCGACCTGAGAG<br>GGTGATCGGCCACACTGGGACTGAGACACGGCCCAGACTCCTACGGGAGGCAGCA<br>GTAGGGAATCTTCCGCAATGGACGAAAGTCTGACGGAGCAACGCCGCGTGAGTGAT<br>GAAGGCTTTCGGGTCGTAAAACTCTGTTGTTAGGGAAGAACAAGTGCTAGTTGAATA<br>AGCTGGCACCTTGACGGTACCTAACCAGAAAGCCACGGCTAACTACGTGCCAGCAG<br>CCGCGGTAATACGTAGGTGGCAAGCGTTATCCGGAATTATTGGGCGTAAAGCGCGC<br>GCAGGTGGTTTCTTAAGTCTGATGTGAAAGCCCACGGCTCAACCGTGGAGGGTCAT<br>TGGAAACTGGGAGACTTGAGTGCAGAAGAGGAAAGTGGAATTCCATGTGTAGCGGT<br>GAAATGCGTAGAGATATGGAGGAACACCAGTGGCGAAGGCGACTTTCTGGTCTGTA<br>ACTGACACTGAGGCGCGAAAGCGTGGGGAGCAAACAGGATTAGATACCCTGGTAGT<br>CCACGCCGTAAACGATGAGTGCTAAGTGTTAGAGGGTTTCCGCCCTTTAGTGCTGA<br>AGTTAACGCATTAAGCACTCCGCCTGGGGAGTACGGCCGCAAGGCTGAAACTCAAA<br>GGAATTGACGGGGCCCGCACAAGCGGTGGAGCATGTGGTTTAATTCGAAGCAAC<br>GCGAAGAACCTTACCAGGTCTTGACATCCTCTGAAAACCCTAGAGATAGGGCTTCTC<br>CTTCGGGAGCAGAGTGACAGGTGGTGCATGGTTGTCGTCAGCTCGTGTCGTGAGAT<br>GTTGGGTTAAGTCCCGCAACGAGCGCAACCCTTGATCTTAGTTGCCATCATTAAGTT<br>GGGCACTCTAAGGTGACTGCCGGTGACAAACCGGAGGAAGGTGGGGATGACGTCA<br>AATCATCATGCCCCTTATGACCTGGGCTACACACGTGCTACAATGGACGGTACAAAG<br>AGCTGCAAGACCGCGAGGTG |

TABLE 6-continued 16s rRNA sequences of Isolated Strains

| Strain Name | 16s rRNA Sequence |
|---|---|
| Strain j1.77 SEQ ID NO: 2 | CGAGCGAACAGAAAAGGAAGNTGCTCCTTTGACGTTAGCGGCGGACGGGTGAGTA ACACGTGGGCAACCTACCCCTANTAGTTTGGGATAACTCCGGGAANCCGGGGCTAA TACCGAATAATCTCTTTTGCTTCATGGTNAAAGACTGAAAGACGGTTTCGGCTGTCG CTATAGGATGGGCCCGCGGCGCATTAGCTAGTTGGTGAGGTAACGGCTCACCAAG GCGACGATGCGTAGCCGACCTGAGAGGGTGATCGGCCACACTGGGACTGAGACAC CGGCCCAGACTCCTACGGGAGGCAGCAGTAGGGAATCTTCCACAATGGGCGAAAG CCTGATGGAGCAACGCCGCGTGAGTGAAGAAGGTTTTCGGATCGTAAAACTCTGTT GTAAGGGAAGAACAAGTACAGTAGTAACTGGCTGTACCTTGACGGTACCTTATTAGA AAGCCACGGCTAACTACGTGCCAGCAGCCGCGGTAATACGTAGGTGGCAAGCGTT GTCCGGAATTATTGGGCGTAAAGCGCGCGCAGGCGGTCCTTTAAGTCTGATGTGAA AGCCCACGGCTCAACCGTGGAGGGTCATTGGAAACTGGGGGACTTGAGTGCAGAA GAGGAAAGTGGAATTCCAAGTGTAGCGGTGAAATGCGTAGAGATTTGGAGGAACAC CAGTGGCGAAGGCGACTTTCTGGTCTGTAACTGACGCTGAGGCGCGAAAGCGTGG GGAGCAAACAGGATTAGATACCCTGGTAGTCCACGCCGTAAACGATGAGTGCTAAG TGTTAGGGGGTTTCCGCCCCTTAGTGCTGCAGCTAACGCATTAAGCACTCCGCCTG GGGAGTACGGTCGCAAGACTGAAACTCAAAGGAATTGACGGGGGCCCGCACAAGC GGTGGAGCATGTGGTTTAATTCGAAGCAACGCGAAGAACCTTACCAGGTCTTGACAT CCCGTTGACCACTGTAGAGATATAGTTTCCCCTTCGGGGGCAACGGTGACAGGTGG NGGCATGGTTGTCGTCAGCTCGTGTCGTGAGATGNTGGGGTTAAGTCCCGCAACGA GCGCAACCCTTGATCTTAGTTGCCATCATTTAGTTGGGCACTCTAAGGTGACTGCCG GTGACAAACCGGAGGAGG |
| Strain j1.21 SEQ ID NO: 3 | AATACATGCAAGTCGAGCGAATGGATTAAGAGCTTGCTCTTATGAAGTTAGCGGCGG ACGGGTGAGTAACACGTGGGTAACCTGCCCATAAGACTGGGATAACTCCGGGAAAC CGGGGCTAATACCGGATAACATTTTGAACCGCATGGTTCGAAATTGAAAGGCGGCTT CGGCTGTCACTTATGGATGGACCCGCGTCGCATTAGCTAGTTGGTGAGGTAACGGC TCACCAAGGCAACGATGCGTAGCCGACCTGAGAGGGTGATCGGCCACACTGGGAC TGAGACACGGCCCAGACTCCTACGGGAGGCAGCAGTAGGGAATCTTCCGCAATGG ACGAAAGTCTGACGGAGCAACGCCGCGTGAGTGATGAAGGCTTTCGGGTCGTAAAA CTCTGTTGTTAGGGAAGAACAAGTGCTAGTTGAATAAGCTGGCACCTTGACGGTACC TAACCAGAAAGCCACGGCTAACTACGTGCCAGCAGCCGCGGTAATACGTAGGTGGC AAGCGTTATCCGGAATTATTGGGCGTAAAGCGCGCGCAGGTGGTTTCTTAAGTCTG ATGTGAAAGCCCACGGCTCAACCGTGGAGGGTCATTGGAAACTGGGAGACTTGAGT GCAGAAGAGGAAAGTGGAATTCCATGTGTAGCGGTGAAATGCGTAGAGATATGGAG GAACACCAGTGGCGAAGGCGACTTTCTGGTCTGTAACTGACACTGAGGCGCGAAAG CGTGGGGAGCAAACAGGATTAGATACCCTGGTAGTCCACGCCGTAAACGATGAGTG CTAAGTGTTAGAGGGTTTCCGCCCTTTAGTGCTGAAGTTAACGCATTAAGCACTCCG CCTGGGGAGTACGGCCGCAAGGCTGAAACTCAAAGGAATTGACGGGGGCCCGCAC AAGCGGTGGAGCATGTGGTTTAATTCGAAGCAACGCGAAGAACCTTACCAGGTCTT GACATCCTCTGACAACCCTAGAGATAGGGCTTCTCCTTCGGGAGCAGAGTGACAGG TGGTGCATGGTTGTCGTCAGCTCGTGTCGTGAGATGTTGGGTTAAGTCCCGCAACG AGCGCAACCCTTGATCTTAGTTGCCATCATTAAGTTGGGCACTCTAAGGTGACTGCC GGTGACAAACCGGAGGAAGGTGGGGATGACGTCAAATCATCATGCCCCTTATGACC TGGGCTACACACGTGCTACAATGGACGGTACAAAGAGCTGCAAGACCGCGAG |
| Strain j1.83 SEQ ID NO: 4 | GGATGGTTGTTTGAACCGCATGGTTCAGACATAAAAGGTGGCTTCGGCTACCACTTA CAGATGGACCCGCGGCGCATTAGCTAGTTGGTGAGGTAACGGCTCACCAAGGCAA CGATGCGTAGCCGACCTGAGAGGGTGATCGGCCACACTGGGACTGAGACACGGCC CAGACTCCTACGGGAGGCAGCAGTAGGGAATCTTCCGCAATGGACGAAAGTCTGAC GGAGCAACGCCGCGTGAGTGATGAAGGTTTTCGGATCGTAAAGCTCTGTTGTTAGG GAAGAACAAGTGCCGTTCAAATAGGGCGGCACCTTGACGGTACCTAACCAGAAAGC CACGGCTAACTACGTGCCAGCAGCCGCGGTAATACGTAGGTGGCAAGCGTTGTCC GGAATTATTGGGCGTAAAGGGCTCGCAGGCGGTTTCTTAAGTCTGATGTGAAAGCC CCCGGCTCAACCGGGGAGGGTCATTGGAAACTGGGGAACTTGAGTGCAGAAGAGG AGAGTGGAATTCCACGTGTAGCGGTGAAATGCGTAGAGATGTGGAGGAACACCAGT GGCGAAGGCGACTCTCTGGTCTGTAACTGACGCTGAGGAGCGAAAGCGTGGGGAG CGAACAGGATTAGATACCCTGGTAGTCCACGCCGTAAACGATGAGTGCTAAGTGTTA GGGGGTTTCCGCCCCTTAGTGCTGCAGCTAACGCATTAAGCACTCCGCCTGGGGAG TACGGTCGCAAGACTGAAACTCAAAGGAATTGACGGGGGCCCGCACAAGCGGTGG AGCATGTGGTTTAATTCGAAGCAACGCGAAGAACCTTACCAGGTCTTGACATCCTCT GACAATCCTAGAGATAGGACGTCCCCTTCGGGGGCAGAGTGACAGGTGGTGCATG GTTGTCGTCAGCTCGTGTCGTGAGATGTTGGGGTTAAGTCCCGCAACGAGCGCAAC CCTTGATCTTAGTTGCCAGCATTCAGTTGGGCACTCTAAGGTGACTGCCGGTGACAA ACCGGAGGAAGGTGGGGATGACGTCAAATCATCATGCCCCTTATGACCTGGGCT ACACACGTGCTACAATGGACAGAACAAAGGGCAGCGAAACCGCGAGGTTAAGCCAA TCCCACAAATCTGTTCTCAGTTCGGATCGCAGTCTGCAACTCGACTGCGTGAAGCTG GAATCGCTAGTAATCGCGGATCA |
| Strain j1.68 SEQ ID NO: 5 | CGTGGGTAACCTGCCTGTAAGACTGGGATAACTCCGGGAAACCGGGGCTAATACCG GATGGTTGTTTGAACCGCATGGTTCAGACATAAAAGGTGGCTTCGGCTACCACTTAC AGATGGACCCGCGGCGCATTAGCTAGTTGGTGAGGTAACGGCTCACCAAGGCAAC GATGCGTAGCCGACCTGAGAGGGTGATCGGCCACACTGGGACTGAGACACGGCCC AGACTCCTACGGGAGGCAGCAGTAGGGAATCTTCCGCAATGGACGAAAGTCTGACG GAGCAACGCCGCGTGAGTGATGAAGGTTTTCGGATCGTAAAGCTCTGTTGTTAGGG |

TABLE 6-continued

16s rRNA sequences of Isolated Strains

| Strain Name | 16s rRNA Sequence |
|---|---|
| | AAGAACAAGTGCCGTTCAAATAGGGGGGCACCTTGACGGTACCTAACCAGAAAGCC<br>ACGGCTAACTACGTGCCAGCAGCCGCGGTAATACGTAGGTGGCAAGCGTTGTCCG<br>GAATTATTGGGCGTAAAGGGCTCGCAGGCGGTTTCTTAAGTCTGATGTGAAAGCCC<br>CCGGCTCAACCGGGGAGGGTCATTGGAAACTGGGGAACTTGAGTGCAGAAGAGGA<br>GAGTGGAATTCCACGTGTAGCGGTGAAATGCGTAGAGATGTGGAGGAACACCAGTG<br>GCGAAGGCGACTCTCTGGTCTGTAACTGACGCTGAGGAGCGAAAGCGTGGGGAGC<br>GAACAGGATTAGATACCCTGGTAGTCCACGCCGTAAACGATGAGTGCTAAGTGTTA<br>GGGGGTTTCCGCCCCTTAGTGCTGCAGCTAACGCATTAAGCACTCCGCCTGGGGAG<br>TACGGTCGCAAGACTGAAACTCAAAGGAATTGACGGGGGCCCGCACAAGCGGTGG<br>AGCATGTGGTTTAATTCGAAGCAACGCGAAGAACCTTACCAGGTCTTGACATCCTCT<br>GACAATCCTAGAGATAGGACGTCCCCTTCGGGGGCAGAGTGACAGGTGGTGCATG<br>GTTGTCGTCAGCTCGTGTCGTGAGATGTTGGGGTTAAGTCCCGCAACGAGCGCAAC<br>CCTTGATCTTAGTTGCCAGCATTCAGTTGGGCACTCTAAGGTGACTGCCGGTGACAA<br>ACCGGAGGAAGGGTGGGGGATGACGTCAAATCATCATGCCCCTTATGACCTGGG<br>CTACACACGTGCTACAATGGACAGAACAAAGGGCAGCGAAACCGCGAGGTTAAGCC<br>AATCCCACAAATCTGTTCTCAGTTCGGATCGCAGTCTGCAACTCGACTGCGTGAAGC<br>TGGAATCGCTAGTAATCGCGGATCA |
| Strain j1.121 SEQ ID NO: 6 | TAACCTACCTATAAGACTGGGATAACTTCGGGAAACCGGAGNTAATACCGGATAACA<br>TGTTGAACCGCATGGTTCAACAGTGAAAGACGGTCTTGCTGTCACTTATAGATGGAT<br>CCGCGCCGCATTAGCTAGTTGGTAAGGTAACGGCTTACCAAGGCAACGATGCGTAG<br>CCGACCTGAGAGGGTGATCGGCCACACTGGAACTGAGACACGGTCCAGACTCCTA<br>CGGGAGGCAGCAGTAGGGAATCTTCCGCAATGGGCGAAAGCCTGACGGAGCAACG<br>CCGCGTGAGTGAAGAAGGTCTTCGGATCGTAAAACTCTGTTATTAGGGAAGAACAAA<br>TGTGTAAGTAACTATGCACGTCTTGACGGTACCTAATCAGAAAGCCACGGCTAACTA<br>CGTGCCAGCAGCCGCGGTAATACGTAGGTGGCAAGCGTTATCCGGAATTATTGGGC<br>GTAAAGCGCGCGTAGGCGGTTTTTTAAGTGTGATGTGAAAGCCCACGGCTCAACCG<br>TGGAGGGTCATTGGAAACTGGAAAACTTGAGTGCAGAAGAGGAAAGTGGAATTCCA<br>TGTGTAGCGGTGAAATGCGCAGAGATATGGAGGAACACCAGTGGCGAAGGCGACTT<br>TCTGGTCTGTAACTGACGCTGATGTGCGAAAGCGTGGGGATCAAACAGGATTAGAT<br>ACCCTGGTAGTCCACGCCGTAAACGATGAGTGCTAAGTGTTAGGGGGTTTCCGCCC<br>CTTAGTGCTGCAGCTAACGCATTAAGCACTCCGCCTGGGGAGTACGACCGCAAGGT<br>TGAAACTCAAAGGAATTGACGGGGACCCGCACAAGCGGTGGAGCATGTGGTTTAAT<br>TCGAAGCAACGCGAAGAACCTTACCAAATCTTGACATCCTCTGACCCCTCTAGAGAT<br>AGAGTTTTCCCCTTCGGGGGACAGAGTGACAGGTGGTGCATGGTTGTCGTCAGCTC<br>GTGTCGTGAGATGTTGGGTTAAGTCCCGCAACGAGCGCAACCCTTAAGCTTAGTTG<br>CCATCATTAAGTTGGGCACTCTAAGTTGACTGCCGGTGACAAACCGGAGGAAGGTG<br>GGGATGACGTCNAATCATCNTGCCNCTTATGATTNGGGCTACACACGTGCTACAATG<br>GACAATA |
| Strain j1.19 SEQ ID NO: 16 | AATACATGCAAGTCGAGCGAACAGATAAGGAGCTTGCTCCTTTGACGTTAGCGGCG<br>GACGGGTGAGTAACACGTGGGTAACCTACNTATAAGACTGGAATAACTCCGGGAAA<br>CCGGGGCTAATGCCGGATAACATTTAGAACCGCATGGTTCTAAAGTGAAAGATGGTT<br>TTGCTATCACTTATAGATGGACCCGCGCCGTATTAGCTAGTTGGTAAGGTAACGGCT<br>TACCAAGGCAACGATACGTAGCCGACCTGAGAGGGTGATCGGCCACACTGGAACTG<br>AGACACGGTCCAGACTCCTACGGGAGGCAGCAGTAGGGAATCTTCCGCAATGGGC<br>GAAAGCCTGACGGAGCAACGCCGCGTGAGTGATGAAGGTCTTCGGATCGTAAAACT<br>CTGTTATTAGGGAAGAACAAATGTGTAAGTAACTATGCACGTCTTGACGGTACCTAA<br>TCAGAAAGCCACGGCTAACTACGTGCCAGCAGCCGCGGTAATACGTAGGTGGCAAG<br>CGTTATCCGGAATTATTGGGCGTAAAGCGCGCGTAGGCGGTTTCTTAAGTCTGATGT<br>GAAAGCCCACGGCTCNNCCGTGGAGGGTCATTGGAAACTGGGAAACTTGAGTGCA<br>GAAGAGGAAAGTGGAATTCCATGTGTAGCGGTGAAATGCGCAGAGATATGGAGGAA<br>CACCAGTGGCGAAGGCGACTTTCTGGTCTGTAACTGACGCTGATGTGCGAAAGCGT<br>GGGGATCAAACAGGATTAGATACCCTGGTAGTCCACGCCGTAAACGATGAGTGCTA<br>AGTGTTAGGGGGTTTCCGCCCCTTAGTGCTGCAGCTAACGCATTAAGCACTCCGCC<br>TGGGGAGTACGACCGCAAGGTTGAAACTCAAAGGAATTGACGGGGACCCGCACAA<br>GCGGTGGAGCATGTGGTTTAATTCGAAGCAACGCGAAGAACCTTACCAAATCTTGAC<br>ATCCTTTGACAACTCTAGAGATAGAGCCTTCCCCTTCGGGGGACAAAGTGACAGGT<br>GGTGCATGGTTGTCGTCAGCTCGTGTCGTGAGATGTTGGGTAAGTCCCGCAACGA<br>GCGCAACCCTTAAACTTAGTTGCCAGCATTTAGTTGGGCACTCTAAGTTGACTGCCG<br>GTGACAAACCGGAGGAAGGTGGGGATGACGTCAAATCATCATGCCCCTTATGATTT<br>GGGCTACACACGTGCTACAATGGACAATACAAA |
| Strain j1.39 SEQ ID NO: 17 | CGCATTAGCTAGTTGGTAAGGTAACGGCTTACCAAGGCAACGATGCGTAGCCGACC<br>TGAGAGGGTGATCGGCCACACTGGAACTGAGACACGGTCCAGACTCCTACGGGAG<br>GCAGCAGTAGGGAATCTTCCGCAATGGGCGAAAGCCTGACGGAGCAACGCCGCGT<br>GAGTGAAGAAGGTCTTCGGATCGTAAAACTCTGTTATTAGGGAAGAACAAATGTGTA<br>AGTAACTATGCACGTCTTGACGGTACCTAATCAGAAAGCCACGGCTAACTACGTGCC<br>AGCAGCCGCGGTAATACGTAGGTGGCAAGCGTTATCCGGAATTATTGGGCGTAAAG<br>CGCGCGTAGGCGGTTTTTAAGTCTGATGTGAAAGCCCACGGCTCAACCGTGGAGG<br>GTCATTGGAAACTGGAAAACTTGAGTGCAGAAGAGGAAAGTGGAATTCCATGTGTAG<br>CGGTGAAATGCGCAGAGATATGGAGGAACACCAGTGGCGAAGGCGACTTTCTGGTC<br>TGTAACTGACGCTGATGTGCGAAAGCGTGGGGATCAAACAGGATTAGATACCCTGG<br>TAGTCCACGCCGTAAACGATGAGTGCTAAGTGTTAGGGGGTTTCCGCCCCTTAGTG<br>CTGCAGCTAACGCATTAAGCACTCCGCCTGGGGAGTACGACCGCAAGGTTGAAACT |

TABLE 6-continued 16s rRNA sequences of Isolated Strains

| Strain Name | 16s rRNA Sequence |
|---|---|
| | CAAAGGAATTGACGGGGACCCGCACAAGCGGTGGAGCATGTGGTTTAATTCGAAGC<br>AACGCGAAGAACCTTACCAAATCTTGACATCCTCTGATCCCTCTAGAGATAGAGTTTT<br>CCCCTTCGGGGGACAGAGTGACAGGTGGTGCATGGTTGTCGTCAGCTCGTGTCGT<br>GAGATGTTGGGTTAAGTCCCGCAACGAGCGCAACCCTTAAGCTTAGTTGCCATCATT<br>AAGTTGGGCACTCTAAGTTGACTGCCGGTGACAAACCGGAGGAAGGTGGGGATGA<br>CGTCAAATCATCATGCCCCTTATGATTTGGGCTACACACGTGCTACAATGGACAATA<br>CAAAGGGTAGCAAAACCGCGAGGTCAAGCAAATCCCATAAAGTTGTTCTCAGTTCG<br>GATTGTAGTCTGCAACTCGACTACATGAAGCTGGAATCGCTAGTAATCG |
| Strain j1.26 SEQ ID NO: 18 | CTGAGAGGGTGATCGGCCACACTGGGACTGAGACACGGCCCAGACTCCTACGGGA<br>GGCAGCAGTAGGGAATCTTCCGCAATGGACGAAAGTCTGACGGAGCAACGCCGCG<br>TGAGTGATGAAGGCTTTCGGGTCGTAAAACTCTGTTGTTAGGGAAGAACAAGTGCTA<br>GTTGAATAAGCTGGCACCTTGACGGTACCTAACCAGAAAGCCACGGCTAACTACGT<br>GCCAGCAGCCGCGGTAATACGTAGGTGGCAAGCGTTATCCGGAATTATTGGGCGTA<br>AAGCGCGCGCAGGTGGTTTCTTAAGTCTGATGTGAAAGCCCACGGCTCAACCGTGG<br>AGGGTCATTGGAAACTGGGGAGACTTGAGTGCAGAAGAGGAAAGTGGAATTCCATGT<br>GTAGCGGTGAAATGCGTAGAGATATGGAGGAACACCAGTGGCGAAGGCGACTTTCT<br>GGTCTGTAACTGACACTGAGGCGCGAAAGCGTGGGGAGCAAACAGGATTAGATACC<br>CTGGTAGTCCACGCCGTAAACGATGAGTGCTAAGTGTTAGAGGGTTTCCGCCCTTTA<br>GTGCTGAAGTTAACGCATTAAGCACTCCGCCTGGGGAGTACGGCCGCAAGGCTGAA<br>ACTCAAAGGAATTGACGGGGCCCGCACAAGCGGTGGAGCATGTGGTTTAATTC |
| Strain j1.116 SEQ ID NO: 19 | CATGGTTCGAAATTGAAAGGCGGCTTCGGCTGTCACTTATGGATGGACCCGCGTCG<br>CATTAGCTAGTTGGTGAGGTAACGGCTCACCAAGGCAACGATGCTAGCCGACCTG<br>AGAGGGTGATCGGCCACACTGGGACTGAGACACGGCCCAGACTCCTACGGGAGGC<br>AGCAGTAGGGAATCTTCCGCAATGGACGAAAGTCTGACGGAGCAACGCCGCGTGA<br>GTGATGAAGGCTTTCGGGTCGTAAAACTCTGTTGTTAGGGAAGAACAAGTGCTAGTT<br>GAATAAGCTGGCACCTTGACGGTACCTAACCAGAAAGCCACGGCTAACTACGTGCC<br>AGCAGCCGCGGTAATACGTAGGTGGCAAGCGTTATCCGGAATTATTGGGCGTAAAG<br>CGCGCGCAGGTGGTTTCTTAAGTCTGATGTGAAAGCCCACGGCTCAACCGTGGAGG<br>GTCATTGGAAACTGGGAGACTTGAGTGCAGAAGAGGAAAGTGGAATTCCATGTGTA<br>GCGGTGAAATGCGTAGAGATATGGAGGAACACCAGTGGCGAAGGCGACTTTCTGGT<br>CTGTAACTGACACTGAGGCGCGAAAGCGTGGGGAGCAAACAGGATTAGATACCCTG<br>GTAGTCCACGCCGTAAACGATGAGTGCTAAGTGTTAGAGGGTTTCCGCCCTTTAGT<br>GCTGAAGTTAACGCATTAAGCACTCCGCCTGGGGAGTACGGCCGCAAGGCTGAAAC<br>TCAAAGGAATTGACGGGGCCCGCACAAGCGGTGGAGCATGTGGTTTAATTCGAAG<br>CAACGCGAAGAACCTTACCAGGTCTTGACATCCTCTGAAAACCCTAGAGATAGGCT<br>TCTCCTTCGGGAGCAGAGTGACAGGTGGTGCATGGTTGTCGTCAGCTCGTGTCGTG<br>AGATGTTGGGTTAAGTCCCGCAACGAGCGCAACCCTTGATCTTAGTTGCCATCATTA<br>AGTTGGGCACTCTAAGGTGACTGCCGGTGACAAACCGGAGGAAGGTGGGGATGAC<br>GTCAAATCATCATGCCCCTTATGACCTGGGCTACACACGTGCTACAATGGACGGTAC<br>AAA |
| Strain j1.119 SEQ ID NO: 20 | AACCGGGGCTAATACCGAATAACACTTTTGACCTCATGGTCGAATGTTAAAAGACGG<br>TTTCGGCTGTCACTACAGGATGGGCCCGCGGCGCATTAGCTAGTTGGTGAGGTAAC<br>GGCTCACCAAGGCAACGATGCGTAGCCGACCTGAGAGGGTGATCGGCCACACTGG<br>GACTGAGACACGGCCCAGACTCCTACGGGAGGCAGCAGTAGGGAATCTTCCACAAT<br>GGACGAAAGTCTGATGGAGCAACGCCGCGTGAGTGAAGAAGGATTTCGGTTCGTAA<br>AACTCTGTTGCAAGGGAAGAACAAGTAGCGTAGTAACTGGCGCTACCTTGACGGTA<br>CCTTGTTAGAAAGCCACGGCTAACTACGTGCCAGCAGCCGCGGTAATACGTAGGTG<br>GCAAGCGTTGTCCGGAATTATTGGGCGTAAAGCGCGCGCAGGTGGTTTCTTAAGTC<br>TGATGTGAAAGCCCACGGCTCAACCGTGGAGGGTCATTGGAAACTGGGAAACTTGA<br>GTGCAGAAGAGGATAGTGGAATTCCAAGTGTAGCGGTGAAATGCGTAGAGATTTGG<br>AGGAACACCAGTGGCGAAGGCGACTATCTGGTCTGTAACTGACACTGAGGCGCGAA<br>AGCGTGGGGAGCAAACAGGATTAGATACCCTGGTAGTCCACGCCGTAAACGATGAG<br>TGCTAAGTGTTGGGGGGTTTCCGCCCCTCAGTGCTGCAGCTAACGCATTAAGCACT<br>CCGCCTGGGGAGTACGGTCGCAAGACTGAAACTCAAAGGAATTGACGGGGGCCCG<br>CACAAGCGGTGGAGCATGTGGTTTAATTCGAAGCAACGCGAAGAACCTTACCAGGT<br>CTTGACATCCCATTGACCACTGTAGAGATACAGTTTTCCCTTCGGGGACAACGGTGA<br>CAGGTGGTGCATGGTTGTCGTCAGCTCGTGTCGTGAGATGTTGGGTTAAGTCCCGC<br>AACGAGCGCAACCCTTATTCTTAGTTGCCATCATTTAGTTGGGCACTCTAAGGAGAC<br>TGCCGGTGACAAACCGGAGGAAGGTGGGGATGACGTCAAATCATCATGCCCCTTAT<br>GACCTGGGCTACACACGTGCTACAATGGACGGTACAAACGGTTGCCAACCCGCGAG<br>GGGGAGCTAATCCGATAAAACCG |
| Strain j1.45 SEQ ID NO: 21 | TGTGGATGGGCTCACGGCCTATCAGCTTGTTGGTGGGGTAATGGCCTACCAAGGCG<br>ACGACGGGTAGCCGGCCTGAGAGGGTGACCGGCCACACTGGGACTGAGACACGG<br>CCCAGACTCCTACGGGAGGCAGCAGTGGGGAATATTGCACAATGGGCGCAAGCCT<br>GATGCAGCGACGCCGCGTGAGGGATGACGGCCTTCGGGTTGTAAACCTCTTTCAGC<br>ACGGAAGAAGCGAAAGTGACGGTACGTGCAGAAGAAGCGCCGGCTAACTACGTCC<br>CAGCAGCCGCGGTAATACGTAGGGCGCAAGCGTTGTCCGGAATTATTGGGCGTAAA<br>GAGCTCGTAGGCGGTTTGTCGCGTCTGCTGTGAAAGCCCGGGGCTTAACCCCGGG<br>TGTGCAGTGGGTACGGGCAGACTTGAGTGCAGTAGGGGAGACTGGAACTCCTGGT<br>GTAGCGGTGAAATGCGCAGATATCAGGAAGAACACCGATGGCGAAGGCAGGTCTCT<br>GGGCTGTTACTGACGCTGAGGAGCGAAAGCATGGGGAGCGAACAGGATTAGATAC |

TABLE 6-continued 16s rRNA sequences of Isolated Strains

| Strain Name | 16s rRNA Sequence |
|---|---|
| | CCTGGTAGTCCATGCCGTAAACGTTGGGCACTAGGTGTGGGGGACATTCCACGTTT<br>TCCGCGCCGTAGCTAACGCATTAAGTGCCCCGCCTGGGGAGTACGGCCGCAAGGC<br>TAAAACTCAAAGGAATTGACGGGGGCCCGCACAAGCGGCGGAGCATGCGGATTAAT<br>TCGATGCAACGCGAAGAACCTTACCAAGGCTTGACATACACCGGATCGGCTCAGAG<br>ATGAGTTTTCCTCCTTGTGGGGCTGGTGTACAGGTGGTGCATGGTTGTCGTCAGCT<br>CGTGTCGTGAGATGTTGGGTTAAGTCCCGCAACGAGCGCAACCCTCGTTCTATGTT<br>GCCAGCACGTGATGGTGGGGACTCATAGGAGACTGCCGGGGTCAACTCGGAGGAA<br>GGTGGGGATGACGTCAAATCATCATGCCCCTTAT |

TABLE 7

Identifier Sequences of Isolated Strains Sequence

| | Query Coverage to closest database match | Percent Identity to closest database match | Sequence |
|---|---|---|---|
| Strain j1.77 | | | |
| Identifier Sequence 1 (SEQ ID NO: 7) | 99 | 77.759 | TTCTATCACCAAAAACAGGTCAATTAACAGTAGGGG<br>ATACACAAGACTTCCAGTTGGTAGAAAACCTGTCGG<br>ATGGGAGCAATCAAGACCAAACAGGAAATACAACAT<br>TTACTGTTAGCGATTCATCCATTGCCACAATACAAA<br>CAACAAACTAACAGCGGTTGCTCCAGGGACCGTGA<br>CGGTAACGGCAACCTATGGTAGCTCATCCGACACA<br>GCAACAATTACGGTGAAAAAGCCTACACCAGTTCCG<br>CCATCGGTACCACAGCCTGTAAATCCAGTGGAACC<br>AAAGCCTTCAGGTGCAATAGACATTATTCGTACTGT<br>TGAACAAGGTATCGTGAAGTATCGAGCAGACGTATC<br>ATTGAATCATGTCCAAATGCTAGTACAACAAATGAC<br>TAATCAAGATGCACGAACAATTCGTCTCGTGTACCC<br>AGCAGAAACAGCAACTGCAAAGGCTTATTTGAATCT<br>TTTTAGAAACGCAGGATTGTTTTTATACAATCAAAAT<br>ACGGATCTTTTCATACAAACAGAGTTAGCACAAATG<br>AGGATTCCTTTTAAATCATTCGATGGCGTGACAGAG<br>GATGTGTACTTCCATCTAGCTCCTGTCAAGGGACCA<br>CAACAGGATATGATTCATACGAATGCCCTAAACAAT<br>GAACAAATCCAGAAAGCAATGCCAGATAGAGCGAT<br>AATTTCATTACTAGGTACACCCGTAAGAATCGAAAC<br>GAATCTACAAAATCGCCCAGTAATGATTACGTTACC<br>GATTTCGTCTGAGTTAACAGAAGATCAAATTGCCTC<br>ACTACTTATCTATGTTGAGCATAGTGACGAAACAAC<br>GGAAGTAAAACATGGGCGTATAGTGGAGTTTGTAC<br>CTGGGGTGAAAGGTTTCCAGTTTGAAGTTGATCACT<br>TCTCAACATATAGCTTAGTATATACTTCAGAAGTTCA<br>AGAAGCTGAGGAAGAAGTAGAGCAAATAGCACCAT<br>ATATTCAAGGTTTCCCAGATGGCACATTTAAACCAA<br>ATGCTTCGGTTACACGTGCACAAATGGCAACAATGT<br>TAGCACGTTTTTTAACGAATGGTGACATACCAACGG<br>CAAGTGCAACTTTTAAAGATACAAAGAATCATCCTTC<br>TAAAGATGCGATTGAATTAGTGAAAGAAATTGGTTT<br>ATTTAACGGTATAACGGATACAACATTTAATCCAAAT<br>GGGACGATTACAA |
| Identifier Sequence 2 (SEQ ID NO: 8) | 99 | 77.188 | CGCTACTGGCGTTACCGGGGCTACTGGTGTTACTG<br>GCGCTACCGGCGCTACCGGCGCTACCGGCGTTACT<br>GGCGTTACTGGTTCTACGGGTGTAACCGGCGCTAC<br>TGGTTCTACCGGCGCTACCGGCGTTACTGGAGTAA<br>CTGGGGCTACTGGTGTTGCTGGTTCTACGGGCGCT<br>ACTGGCGCAATCGGACCTACTGGCGCTACTGGCGT<br>TACTGGCGCTACCGGGGCTACTGGGGTAACTGGG<br>GCTACCGGCGTTACTGGGGTAACCGGCGCTACTGG<br>CGCTACTGGTGTAACCGGGGCTACCGGGGCTACTG<br>GCTTGACTGGCGCAATCGGACCTACTGGCACCACT<br>GGGATAACTGGGGCTACCGGCGTTACTGGCGTTAC<br>TGGCGCTACCGGCGTTGCTGGGGCTACGGGTGAG<br>ACTGGCGCTACTGGGGTAACTGGGGCTACCGGTGT<br>TGCTGGGGCTACGGGCGCTACGGGCGTTACTGGC<br>GCAATCGGACCTACTGGCGCTACTGGTGTAACCGG<br>GGCTACCGGCGTTACTGGCGTTACTGGGGCTACCG |

TABLE 7-continued

Identifier Sequences of Isolated Strains Sequence

| | Query Coverage to closest database match | Percent Identity to closest database match | Sequence |
|---|---|---|---|
| | | | GCGTTACTGGGGTAACCGGCGCTACTGGCTTGACT<br>GGTGCAATCGGACCTACTGGCGCTACTGGAGTAAC<br>CGGGGCTACCGGCGTTACTGGGGCTACTGGCGTTA<br>CTGGGGTAACTGGGGCTACCGGCGTTACTGGCGTT<br>ACTGGCGCTACCGGCGTTGCTGGCGTTACCGGCGT<br>TACTGGCGCTACTGGCGTTACTGGTTCTACGGGAG<br>TGACCGGCGCTACTGGTATTACTGGTTCTACGGGT<br>GTAACCGGGGCTACTGGCGCTACTGGTTCTACTGG<br>GGTAACCGGCGTTACTGGTTCTACGGGTGAGACTG<br>GGGTAACTGGGGCTACCGGCATTACTGGAGTAACC<br>GGCGCTACTGGCATTACTGGAGTAACCGGCGCTAC<br>TGGCACTACTGGAGTAACTGGCGCTACCGGCGTTA<br>CTGGCGCTACCGGCGTTGCTGGGGCTACGGGTGA<br>GACCGGCGCTACTGGCACTACTGGAGTAACTGGGG<br>CTACCGGTGTTGCTGGTTCTACGGGCGCGACTGGC<br>GCAATCGGACCTACTGGCGTTACTGGTGTAACTGG<br>GGCTACCGGCGCAATCGGACCTACTGGCGTTACTG<br>GAGCTACCGGCGTTGCTGGGGTAACTGGGGCTACT<br>GGCGTTACTGGTGC |

Strain j1.21

| Identifier Sequence 1 (SEQ ID NO: 9) | 99 | 81.925 | TATAAATCCGTAATGCTTTTTTCTTTTGTTCGTTTAC<br>ATTCATAAAATCGTGTAACCTTTTAAGCTTTTTCCCT<br>TTCTGCTCTTCTACATTGCTTTGAAGTTTTAATGTAA<br>CATACTGCCCTTTTTTCACGAGTAAATCAATAATAAA<br>TCTACGAAAATCATGATATTGAATAGGTACATGATTT<br>ACACAACCATACTTTCCTGCTCTTCTATACTGTGAG<br>CACTTTAAATATTTCCATTCAGTCCGTTCACCATTCT<br>TCTTTCGAAGATAGGATTGTACGATAACCATATTTGA<br>ACCACAAATCGCGCATTTTGCTAAATTACGAAATTC<br>ATTCCAAGCTGTGATTTTTGTTTTACTCATAATAATG<br>TCTTTTTGATTTGCTCGATTCCATATCTCTTCATCTA<br>CAATTTTGGGATGGTGATTAGGAAAAACAAACCACT<br>TTTCTCTCGGATTGCGAATTTGTTTTTTCCTACCGTT<br>CACCTTGACCGAGGTATATTGATTTAAAATAAACGT<br>CCCTTTGTAAATTGGATTTTGAAGAATACGCTGAAC<br>GGATGTTATTTGCCAATTTTTTTTAGTTTTAGATTTTA<br>TCCCCATTTTATTTAACTCATTTGAAATTTTTTTATAT<br>CCCCACCCATTGATATACCAACTATATATCCTTCGA<br>ACAACATTAGATTCCTCTTCATTAATAATCAACTTTT<br>GATTAATACGGTCATACCCATACGGTACTTTACCAA<br>TATGCTCACCTCTTCTTACTTTCACCGCCAAAGCAG<br>CAGTAATACTCGAAGATAATGTCCGACTATACTGCG<br>CCGAAAATAAAGACCATAACTCAAATGCCATATCAT<br>TTTTCCCAGCTTTTACAGAATCATAGCCTTCTTCCAC<br>AGAAACAATTCTAACATTATGAGCTAAAAGCACTTCT<br>CTTATCTCTAATGAGTCCTTTAAATCACGCGCTAAAC<br>GAGAAATAGACTTAAAGACAACCATATCAATTTCTTT<br>CGCCTTCGCCTTTTGTAATAATAATTGAATAGCAGG<br>ACGATCCATAAATAAAGTACCACTCATCCCCTCATC<br>TTTAAAAACACATTTTTCATTCCACATAAATCCATTA<br>CGCTCCAACCAATTCCTACAAATATCTATTTGGTTTT<br>CAATCGAGGAAACTTGTTCATCACGATCTGTTGATA<br>CGCGAACATAAACAGCATAAGATTCC |
| Identifier Sequence 2 (SEQ ID NO: 10) | 99 | 74.631 | CTGTTTTAGTCCTCCTAAGTAATATTTCATAACTTCA<br>TATTTTGCATGTGTATCATCAGATAGTAGAATGTCAA<br>TTTCATATTCTAAAATCGGCAACTTATGATATATGAA<br>GTCGAAAAAATCTGTTTCGGTTGTGAATTCAAATTGT<br>TTTAAAGTATCTTTGAAAAATCTTTCTCGATTGAGTA<br>ATAATTGCAACAAATGATTTTCTAAATGCTTTATTTCT<br>CGCATTTTTTTATGTATGGCTTTTTGTTTAGCTATTT<br>CTTTTTGCATGTTTTTATTATTTAGATTTACATCTAAA<br>TTCAATTCTTTTAAAAGAAAAGATTCTGCTTGTTTGT<br>GCGTCCATCCATGCAATATCATCAGACCTGAAAATT<br>GGTCTATTGGTCTTCTATTCCCGCACCCTGCGAAAC<br>AATAACAGTTGTTGTCTGATACGTTCACAACCATGC<br>TATCTTTGTTATCTGCATGGAAGGGACACTTGCACA<br>TGTAATTTTTTCCCCGCTTTCTAACAGTTACCCCGCA<br>ATAGCTTTCTAAGAAATTTATAATAGGAAGTTTACTT<br>TTAATTAGATCGCTTTTTTGCATATCATCACACTTCT |

TABLE 7-continued

Identifier Sequences of Isolated Strains Sequence

| | Query Coverage to closest database match | Percent Identity to closest database match | Sequence |
|---|---|---|---|
| | | | TTATCTTTGAAAATAATTTTGATATGTTTAGCTTGGTT<br>TTTTCCTCGTTGATAGAAAACATCTGTAAGACCTTTT<br>TCCTCCAAACCTTTGAAGGCTCGTCCAACGCTAGAG<br>CGTGATAAATTGCAATGTTCTATTACATCTTCAATCT<br>TAATTTTTTCGTGTTGTTCTGCACAACCTTGCTGATG<br>TAGATAGAGCAATACAAGTTTTTCAGTAGGTGTTGT<br>TTCTTGGACTTCGAAAATGTCTTTTATCGTCAATATT<br>CTGCTCCTCCTGTCAAATTTCTTTATGAATTTAACTT<br>TAACAGATATTTTCTTATGCGTCAATATGACACATAA<br>GAATTATATAACGAAAATAATTAAATCCTTTAATATAA<br>ACGATTTCTAGCGAGTAATAAAAACGATTCCTTGATT<br>CATTTTCGGAAACACCTGACGTCTTCCCTACGATTC<br>CTTATATTTTTTGCGGGGATTATTCATGTTTCTTTGT<br>CAATCAGCAAGGACAAACAATCCTCGCTATTTTGAG<br>AGTGTATTTTCATATTCCTTCATGATTTTGTAGAATG<br>ATGTTTTTTTGAGATTTAGCATTTGACTGAATTCTAC<br>ACCTTTGATTTCTTTGCTTT |

Strain j1.83

| | | | |
|---|---|---|---|
| Identifier Sequence 1 (SEQ ID NO: 11) | 100 | 88.353 | GTTTCTCCCGTTGCTCCGGTTACTCCTGTTGCCCCA<br>GTTGGGCCGGTTGCTCCGATTGAACCTGTTGCTCC<br>GGTTGGACCGGTCTCTCCCGTTGGGCCGATTTCTC<br>CAGTTACACCGGTTGCGCCGGTTTCTCCCGTTGAA<br>CCAATTGAGCCGGTTACTCCTGTTGCCCCTGTTGCT<br>CCAGTTACACCAGTCAAGCCGGTTGGGCCTGTTATT<br>CCTGTTATTCCTGTTGCTCCGGTTGAACCGGATGCA<br>CCCGTCGCCCCGGTTTCTCCTGTCGATCCCGTTGG<br>ACCAGTCTCCCCAGTTGACCCGGTTGATCCTGTCG<br>CGCCTGTTACTCCCGTTGGGCCTGTTGGGCCTGTT<br>GAGCCGGTCGTTCCCGTTGCTCCTGTCGGCCCGGT<br>TATTCCTGTCGCACCGGTTTCTCCGGTTACTCCCGT<br>CGCCCCGGTTACTCCAGTTGAACCCGTTTCTCCTGT<br>CGATCCTGTTGATCCGGTTACACCAGTTGAGCCCG<br>TGACCCCAGTCGGGCCAGTCACTCCTGTTGATCCT<br>GTTGCACCAGTTACTCCGGTTGGGCCTGTTGAACC<br>TGTCGATCCCGTTGCGCCGGTTGGGCCTGCTGCGC<br>CAGTTGAGCCGGTTGAGCCAGTTGGCCCGATTTCT<br>CCAGTTGAACCGGTCGCTCCTGTCTCCCCGGTCGC<br>TCCTGTTGGGCCGATCGGGCCAGTAGCCCCTGTGG<br>CTCCCGTTATCCCCGTTGCCCCAGTCACTCCAGTTG<br>GACCCGTTTCTCCCGTTGAGCCAGTTGCTCCTGTTT<br>CTCCTGTTGGACCAGTCTCCCCAGTTGACCCGGTT<br>GATCCGGTTTCTCCTGTCGATCCCGTTGCGCCGGT<br>TATTCCTGTTACACCGGTCTCTCCTATTGCGCCGGT<br>TGGGCCTGTTACTCCAGTCGCTCCGGTTGGACCGG<br>TTTCTCCGGTTGAACCAGTTGACCCTGCTGCTCCTG<br>TTGGTCCAGTTACTCCCGTTGAACCAGTTGATCCCG<br>TTATACCAGTTACCCCAGTCGCTCCTGTCGATCCCA<br>TTGCACCCGTTGAGCCGGTGGCTCCTGTTACTCCC<br>GTTGCTCCGGTTGAGCCGGTTGGGCCGGTTGGGC<br>CGGTTACACCCGTGACCCCAGTCGGGCCAGTAACT<br>CCTGTTGCCCCTGTTACTCCGGTCGATCCCGTTTCT<br>CCTGTTGCACCTGTTACTCCGGTCTCTCCTGTT |
| Identifier Sequence 2 (SEQ ID NO: 12) | 99 | 93.709 | AAAACTGTCAGTGTAATGGATACACCTGATTTCCCG<br>GAGATTTTATTCCAACAGCTAAAGGCCAAGGTCGT<br>AACTTGCAAGAACTAAAGGAAACTTCTGATATTAACT<br>GGACATTTATCAGTCCTTCAGCGGTATTTGACCCAG<br>ACGGGAAAAGAACTGGATTTTATCAGTCAGGAAAAG<br>ATCATCTTCTTGTGAATTCGAAAGGCGAAAGTTATAT<br>CAGCTATGCAGACTATGCAATTGCAGTATTGGATGA<br>AATTGAAAATCCAAAACATATAAATGAACGCTTTACA<br>GTTGTTGGAGAAGCTGAATAAGTGATTGAGTAGAAA<br>CAAAGGGTACCATTAGTGTCATCGCTAATGGTATCT<br>TCCTTCTAAGAATGTACGGAGACATTGAAAACTTTG<br>CAATCAGAGTAGCTGATTATTAAAAAGGGGATTTAT<br>CACGTTCCAATGAATATTATCGAGCTGATGACAGAG<br>TAGGTGCTTAGTGAGTTGGACCAAAAAAATATGTAT<br>GTGTATAAAAAGCTCTGACTAAGACCTTTTGGATTA<br>GTTAGAGCTTCTTTATTTGACTGTGTTACCCAGTGTA<br>ATCCTCCGTATTGTTTAATACACTTTAGTTTGAAAAT |

TABLE 7-continued

Identifier Sequences of Isolated Strains Sequence

| | Query Coverage to closest database match | Percent Identity to closest database match | Sequence |
|---|---|---|---|
| | | | CCGGGAAACTCTTCTACAGTTCCTATTTCGTGTTTA<br>AAGTGTGAATATTCCAGCGGGGAACTTTACTGAAAT<br>GAGGGGTATTTTCGAAAACACACCAGTATGCTCTAT<br>GACCTGCCGTCAATGACATTAAAGAAATGATTTGAT<br>GTAAAAAGGAGCGATATTCGTTAAAATTTAGGTAGT<br>AGCCATACATAGCCATATAAAACACATGATTAATTCT<br>AAATTCTTTACTGATCGTTCTTAAATTTGATATACTT<br>GAAATACGTTAGATCTAACTGTTTTGCTACTCAAATG<br>AGAATGATCGTTCTTTAATTATTTAAGAATGAGGGA<br>GGGATGAATGCATCAATGATTCTCAGGCCTTTCTCA<br>GAATAAAGAGGTAATACATTCTAAGGTGGGATTACA<br>TGGCTAGAAATAAAGAATTTGATGAAAAAAAGCAT<br>TAAGAAAAGCAATGGATCTTTTCTGGGAACAGGGTT<br>ATGAAAAACATCCATGCAAGACTTGGTGGACCATA<br>TGGGCATTCACCGCAGAAGTATTTATGATACATTTG<br>GCGACAAACATACTTTATTTATGCGAGCCTTAAGTC<br>AGTA |

Strain j1.68

| Identifier Sequence 1 (SEQ ID NO: 13) | 100 | 88.353 | GTTTCTCCCGTTGCTCCGGTTACTCCTGTTGCCCCA<br>GTTGGGCCGGTTGCTCCGATTGAACCTGTTGCTCC<br>GGTTGGACCGGTCTCTCCCGTTGGGCCGATTTCTC<br>CAGTTACACCGGTTGCGCCGGTTTCTCCCGTTGAA<br>CCAATTGAGCCGGTTACTCCTGTTGCCCCTGTTGCT<br>CCAGTTACACCAGTCAAGCCGGTTGGGCCTGTTATT<br>CCTGTTATTCCTGTTGCTCCGGTTGAACCGGATGCA<br>CCCGTCGCCCCGGTTTCTCCTGTCGATCCCGTTGG<br>ACCAGTCTCCCCAGTTGACCCGGTTGATCCTGTCG<br>CGCCTGTTACTCCCGTTGGGCCTGTTGGGCCTGTT<br>GAGCCGGTCGTTCCCGTTGCTCCTGTCGGCCCGGT<br>TATTCCTGTCGCACCGGTTTCTCCGGTTACTCCCGT<br>CGCCCCGGTTACTCCAGTTGAACCCGTTTCTCCTGT<br>CGATCCTGTTGATCCGGTTACACCAGTTGAGCCCG<br>TGACCCCAGTCGGGCCAGTCACTCCTGTTGATCCT<br>GTTGCACCAGTTACTCCGGTTGGGCCTGTTGAACC<br>TGTCGATCCCGTTGCGCCGGTTGGGCCTGCTGCGC<br>CAGTTGAGCCGGTTGAGCCAGTTGGCCCCGATTTCT<br>CCAGTTGAACCGGTCGCTCCTGTCTCCCCGGTCGC<br>TCCTGTTGGGCCGATCGGGCCAGTAGCCCCTGTGG<br>CTCCCGTTATCCCCGTTGCCCAGTCACTCCAGTTG<br>GACCCGTTTCTCCCGTTGAGCCAGTTGCTCCTGTTT<br>CTCCTGTTGGACCAGTCTCCCCAGTTGACCCGGTT<br>GATCCGGTTTCTCCTGTCGATCCCGTTGCGCCGGT<br>TATTCCTGTTACACCGGTCTCTCCTATTGCGCCGGT<br>TGGGCCTGTTACTCCAGTCGCTCCGGTTGGACCGG<br>TTTCTCCGGTTGAACCAGTTGACCCTGCTGCTCCTG<br>TTGGTCCAGTTACTCCCGTTGAACCAGTTGATCCCG<br>TTATACCAGTTACCCCAGTCGCTCCTGTCGATCCCA<br>TTGCACCCGTTGAGCCGGTGGCTCCTGTTACTCCC<br>GTTGCTCCGGTTGAGCCGGTTGGGCCGGTTGGGC<br>CGGTTACACCCGTGACCCCAGTCGGGCCAGTAACT<br>CCTGTTGCCCCTGTTACTCCGGTCGATCCCGTTTCT<br>CCTGTTGCACCTGTTACTCCGGTCTCTCCTGTT |

Strain j1.121

| Identifier Sequence 1 (SEQ ID NO: 14) | 100 | 90.884 | AATATAAACAAATTGTGCTAAATCCGCTTTATAGTAT<br>AAGTAACAAAACGATAGATAAACAAACAACACAAGT<br>TCATTCATCGTTTTAAATTAATTAACTCACGCATTAT<br>CACATTTTACTGAAGGAGTGTTTGTAATGGAAAAATT<br>ATTCGACGCAATTAGAAACACAGTCGATGCTGGAAT<br>CAACCAAGATTGGACAAAATTAGGAACTAGCATTGT<br>TGACATCGTTGACAATGGTGTAAAAGTTATTTCTAAA<br>TTTATTGGTGCATAATTCAGATTATTAATATCGTTTTA<br>ATAATAAAGGAGAGATTATAATGCAAAAATTAGCAG<br>AAGCAATCGCAAACACAGTAAAAGCAGGACAAGAC<br>CATGATTGGACAAAATTAGGTACAAGCATCGTTGAT<br>ATCGTAGAAAACGGTGTAAGTGCATTAACTAAAGTA<br>TTCGGTGGTTAATTTTCGATAAATAAGAACTTAATTA<br>TAAATAAAATAAACTAAAGGAGAGACTATAATGACTA<br>AATTAGCAGAAGCAATCGCAAACGCAGTAAAAGCA |

TABLE 7-continued

Identifier Sequences of Isolated Strains Sequence

| Query Coverage to closest database match | Percent Identity to closest database match | Sequence |
|---|---|---|
| | | GGACAAGACCAAGATTGGGCAAAATTAGGTACAAG<br>CATCGTAGGTATCGCAGAAAACGGAATCGGTTTATT<br>AGGTAAAGTATTCGGATTCTAATATATGATTAGATG<br>GACCAGGGCAAGCGCTCTGGTCTTTTTTTATTTGCA<br>GATTATTTGTTATTATTAAAAAGAATAAGAAGTTTGT<br>TCATTAAAATTTGAAACGGGGATAAATTGTGACATAT<br>AAACATATCTTATTAGATTTCGATGATACAATAGTTG<br>ATTTTTACGATGCAGAGGAAAAGGCATTTTATAATAT<br>GGCAAAACATTACGGTCATTTTCCGACTAAACAAGA<br>TTTCCAACATTTTAGAAAGGTCAATCAAGCACACTG<br>GGAAGCTTTTCAACAAAATGAATTGACGAAAGAACA<br>AGTTTTATCTCATCGATTTATTAATTATTTCAATGATT<br>ATTACATAGAAGTAGATGGTAAAGAAGCGGATGAGA<br>TATTTAGAGATGAATTAGCTAAAGCGCCGCTTAAAT<br>TTTTCGATCAAACGATTGAAACTATTAACCAGCTGAA<br>AGATAAACATTCATTATATATTGTTACGAATGGTGTG<br>ACAATCACGCAACAGCGTCGTATTGCTCAGACAAAT<br>TTTAATGATATATTTAATGGAATATTTATTTCAGA |
| | | Strain j1.27 |
| Identifier Sequence 1 (SEQ ID NO: 15) | 100 | 97.087 | CACTCGTGCCAAGAGCTAATGATAGCCCAAGCCCT<br>GTAACAATTACTTCAACTAATGATGGAGTTGTCGTA<br>ATTTGCGTAATTGCTTGAATAACGATAGGTGCTCCG<br>AGTGAGATTAAACTCGATCCAGTACCTGGTACAGGT<br>ACTCCATTCACTTGGATTGTAAGACCTCCTAATAGA<br>CTTGCAGTTGCAGTGTTAGCGATAACAGTGATTTTA<br>TAGAATCCAGTTTCACTAATTACGAAAGTATCAGCAT<br>CTAATTGAGAAATTGCTGTACCAAACTGAGATCCAA<br>CAGTATTAAATGGTACTGGATCATTAATTCCTAAATC<br>TAAAGAAATCCCACCGGAGTTAAATGCGTATAGTCC<br>TGCTGGAAGTCCTAGTCCTGATGGTCCAGTCGGTC<br>CAGTCGGTCCAGTAGCCCCAGTCGGTCCAGTAGCT<br>CCAGTAGCTCCAGTGTCACCAGTCGGCCCCGTAGG<br>TCCAGTAGCTCCAGTGTCACCAGTCGGCCCCGTAG<br>GTCCAGTAGCCCCAGTGTCACCAGTCGGCCCCGTA<br>GGTCCAGTAGCCCCAGTGTCACCAGTCGGCCCCGT<br>AGGTCCAGTAGTCCCAGTGTCACCAGTCGGTCCAG<br>TCGGCCCCGTAGGTCCAGTCGGCCCAGTCGGCCC<br>CGTAGGTCCAGTCGGTCCAGTTGGCCCGGTAGGTA<br>CAGTCGGCCCCGTAGGTCCAGTCGGCCCAGTCGG<br>CCCGGTCGGCCCAGTCGGAAGGGTAAACGGTGGT<br>ATCGGTGGTAATGTAGGTCCTACAAGATTAGGGTCA<br>AATGCACTAGCTGATAAAGATTCATCGGGATTTAAT<br>CCATTTGAATAATTATTATTTGACATAAATTCACCTC<br>CATAAAGCGTTCATTATATAGTAGATGCAAAACCGA<br>AAGAAAATGACACGGACATTTGAATTATTGAAAAGA<br>AATCTTAAACTACTTGAACAATTTAAAAAAATGGAAA<br>GTTTAGTATATGTATAACATATGATTGATTTGGAAGA<br>GGGTGATTATGTTGAACAAGCAAGGAATTACAATTA<br>GTTTATGTATGATTGTTCGAGATGAGGAGGAGACAA<br>TAGCCCGTTGTTTAGACACAGTTGAAAAAATTGTGG<br>ATGAAATTATAGTGGTTGATACAGGCTCCGTCGATC<br>GAACGAAAGAAATCGTAGAGAAATACACTTCTAACA<br>TATATGATTTCCAGTGGATTGA |

Example 13: Quorum Sensing and Metabolism Expression of *S. aureus* on Agar Plates when Mixed with Strain j1.68

Figure 17A:
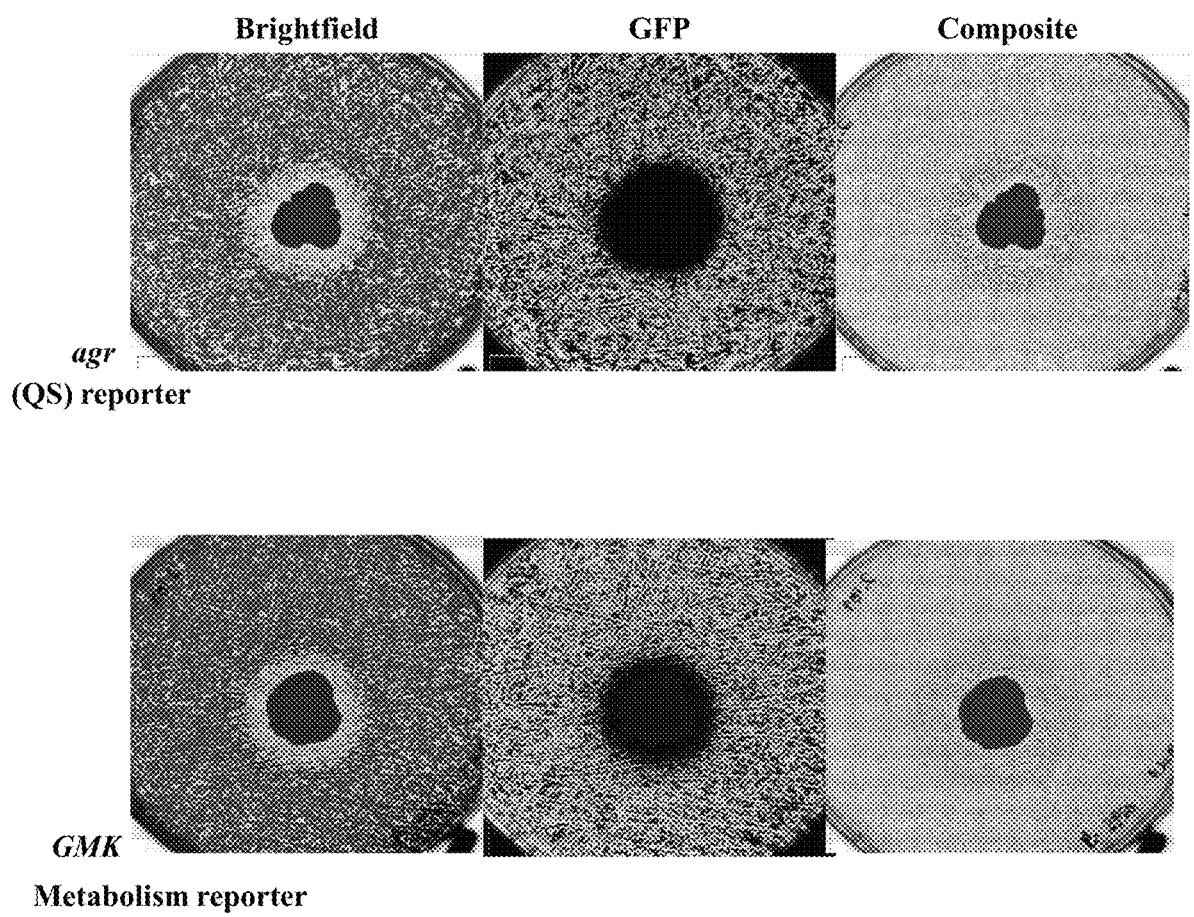
FIGS. 17A-17B, depict images of agar plates containing Strain jl.68 whole cells plated on a lawn of *S. aureus* cells. The *S. aureus* cells contained reporters for expression of agr (quorum sensing) and GMK (metabolism). The expression of agr and GMK was affected by the addition of Strain jl.68.
Figure 17B:
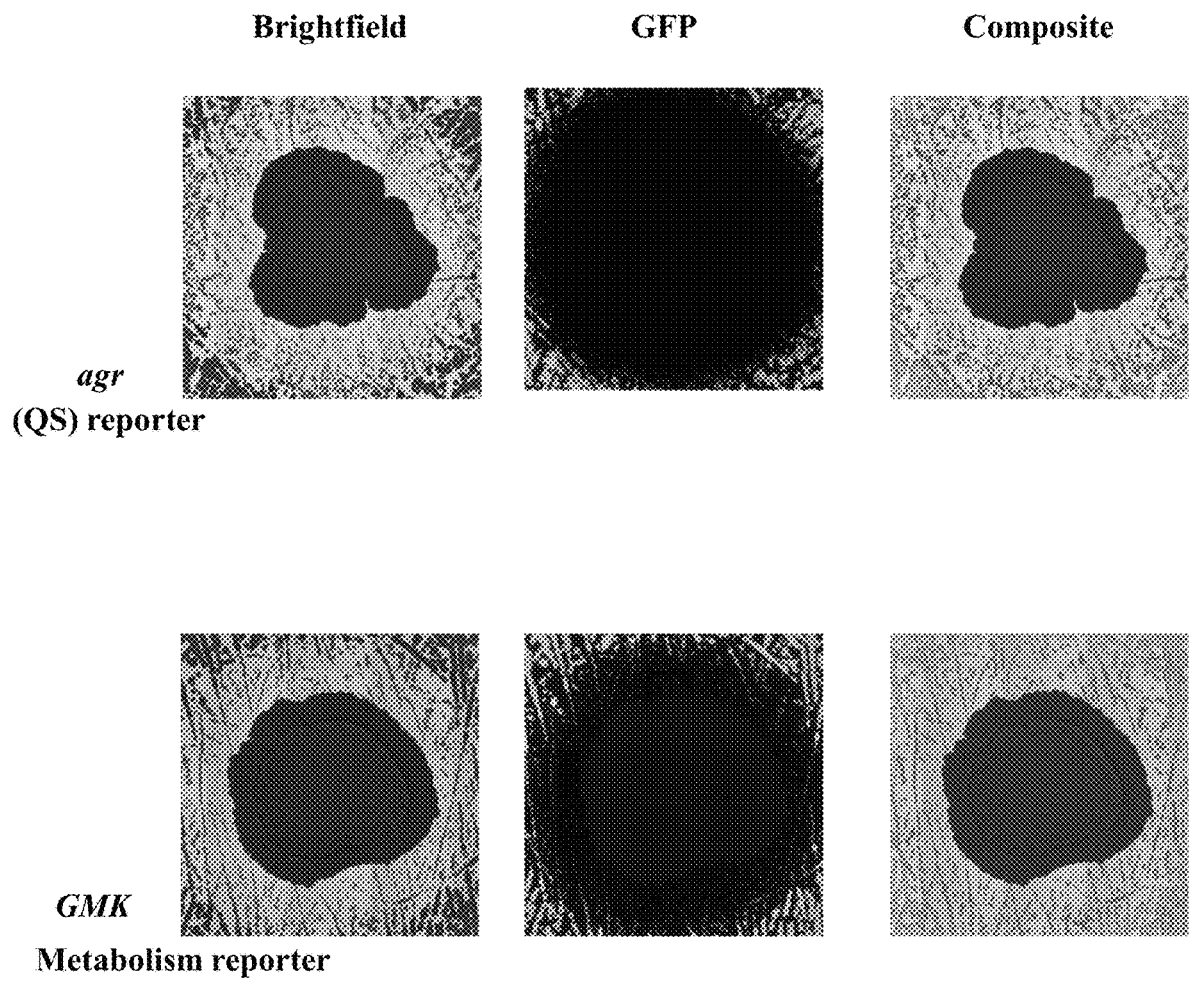

*S. aureus* reporter strains containing a GMK promoter fused GFP reporter or an agr promoter fused GFP reporter were spread on agar plates. 10 microliters of Strain j1.68 was plated in the center of the plate. Images of the plates were taken after incubation for 24 hours at 37° C. FIGS. 17A-B show the expression and growth of the *S. aureus* reporter strains. The expression of the reporters is shown in the GFP column. The growth of the *S. aureus* is shown in the brightfield column. The image suggests that cells of Strain j1.68 slow the growth of *S. aureus* and affect quorum sensing on agar plates.

Example 14: Growth of *S. aureus* and Expression of *S. aureus* Genes after Mixture with Selected Strains and Supernatant of Selected Strains

Figure 18A:
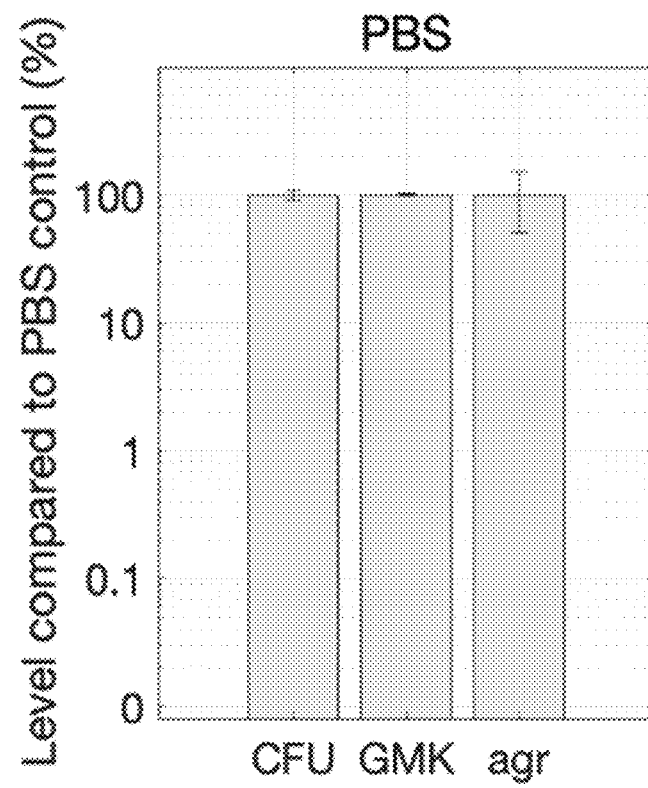
FIGS. 18A-18F, depict bar graphs that show expression of *S. aureus* agr and GMK reporters in *S. aureus* cells and the CFU of *S. aureus* cells in monoculture or after being mixed with different strains of bacteria.
Figure 18B:
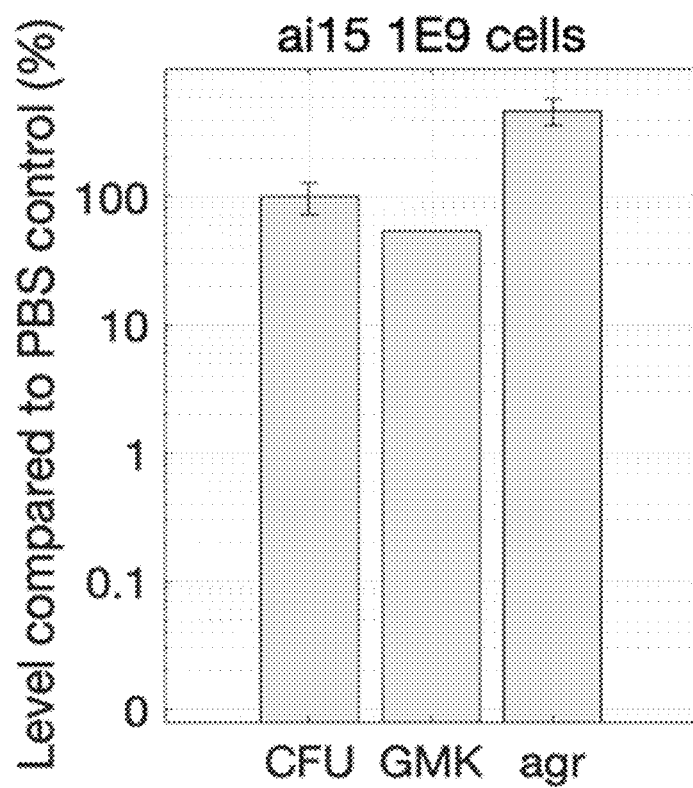
Figure 18C:
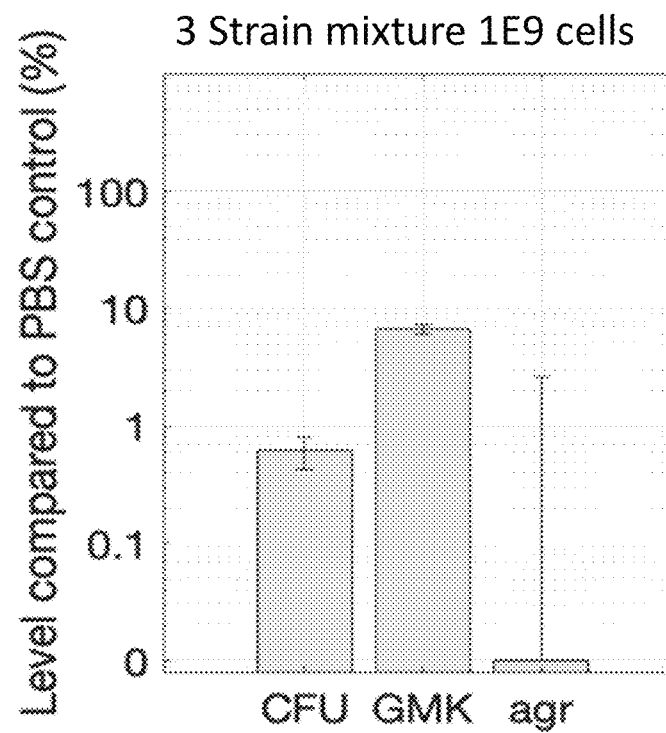
Figure 18D:
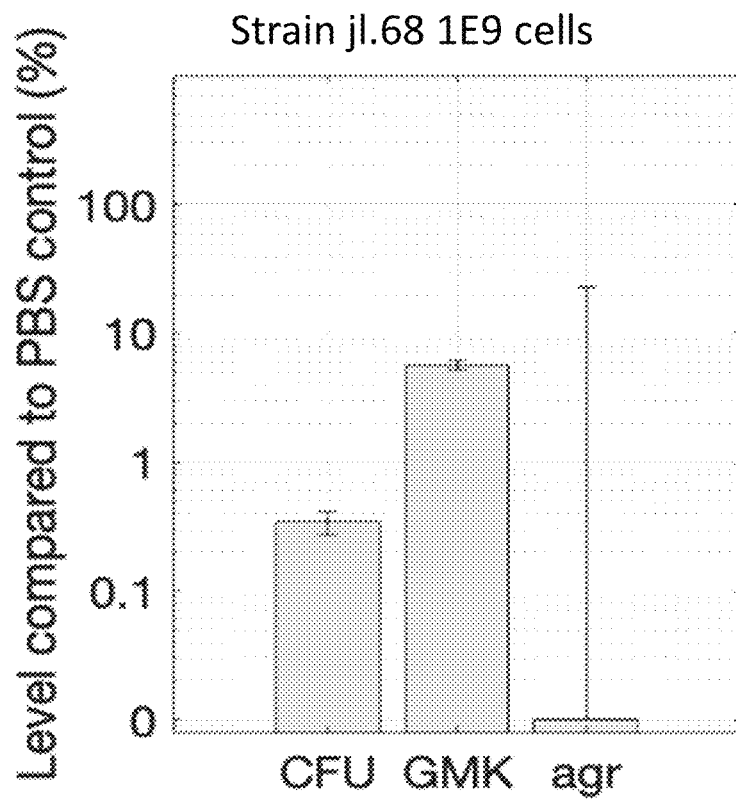
Figure 18E:
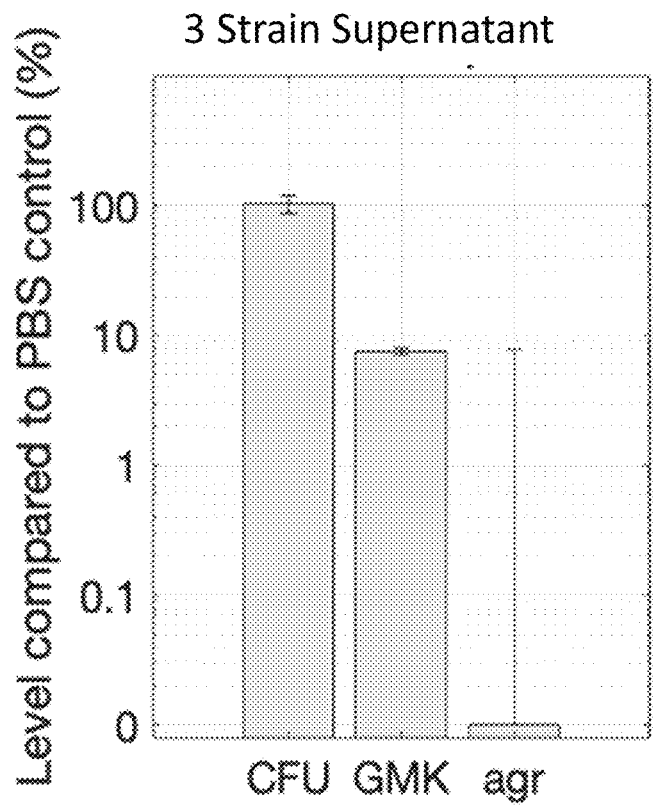
Figure 18F:
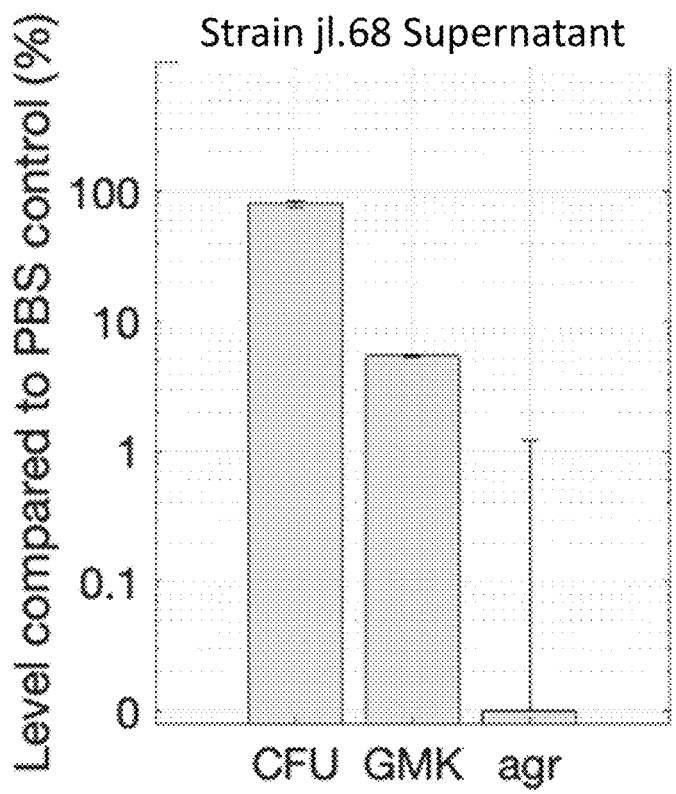

*S. aureus* reporter strains containing a GMK promoter fused GFP reporter or an agr promoter fused GFP reporter were grown in liquid cultures in the following conditions: grown in monoculture, mixed with *S. aureus* WT (control);

mixed with Strain jl.27, Strain jl.68, and Strain jl.77; mixed with Strain jl.68 alone; mixed with supernatant from Strain jl.27, Strain jl.68, and Strain jl.77; or mixed with supernatant from strain jl.68 alone. The expression of GMK and agr were determined after incubation for 24 hours. The levels of expression and CFU were compared to a PBS control and calculated by (time 24–time 0)/(time 24 PBS–time 0 PBS). FIGS. 18A-F show the level compared to PBS on the Y-axis and the CFU, GMK expression and agr expression on the X-axis in the different growth conditions. The "agr" error bars appear large because less-than-zero values were set to 0. FIG. 18A shows the CFU of S. aureus and the expression of GMK and agr in a S. aureus monoculture control. FIG. 18B shows in a 1:1 coculture with ai.15 (S. aureus WT), there were increases in quorum sensing with little or no effect on cell viability or metabolism. FIGS. 18C-D show in a 1:1 coculture with Strain jl.27, Strain jl.68, and Strain jl.77 or with Strain jl.68 there was reduced cell viability (<1% (CFU)). Similarly, quorum sensing (agr-GFP) was reduced to negligible levels (near 0%) compared to the PBS control, and metabolism (GMK-GFP) was reduced to 5-10% as compared to the PBS control. FIGS. 18E-F show Strain jl.27, Strain jl.68, and Strain jl.77, or Strain jl.68 supernatant caused quorum sensing (agr-GFP) to be reduced (near 0%). Cell viability (CFU) was unaffected and metabolism (GMK-GFP) was reduced to 5-10% as compared to the PBS control. In liquid coculture with high-density S. aureus ($10^9$ CFU/mL), the three strain combination of Strain jl.27, Strain jl.68, and Strain jl.77 and the single Strain jl.68 quenched quorum sensing (agr) and reduced viability (<1%). Similarly the supernatant maintained this effect on quorum sensing without reducing viability.

Figure 19A:
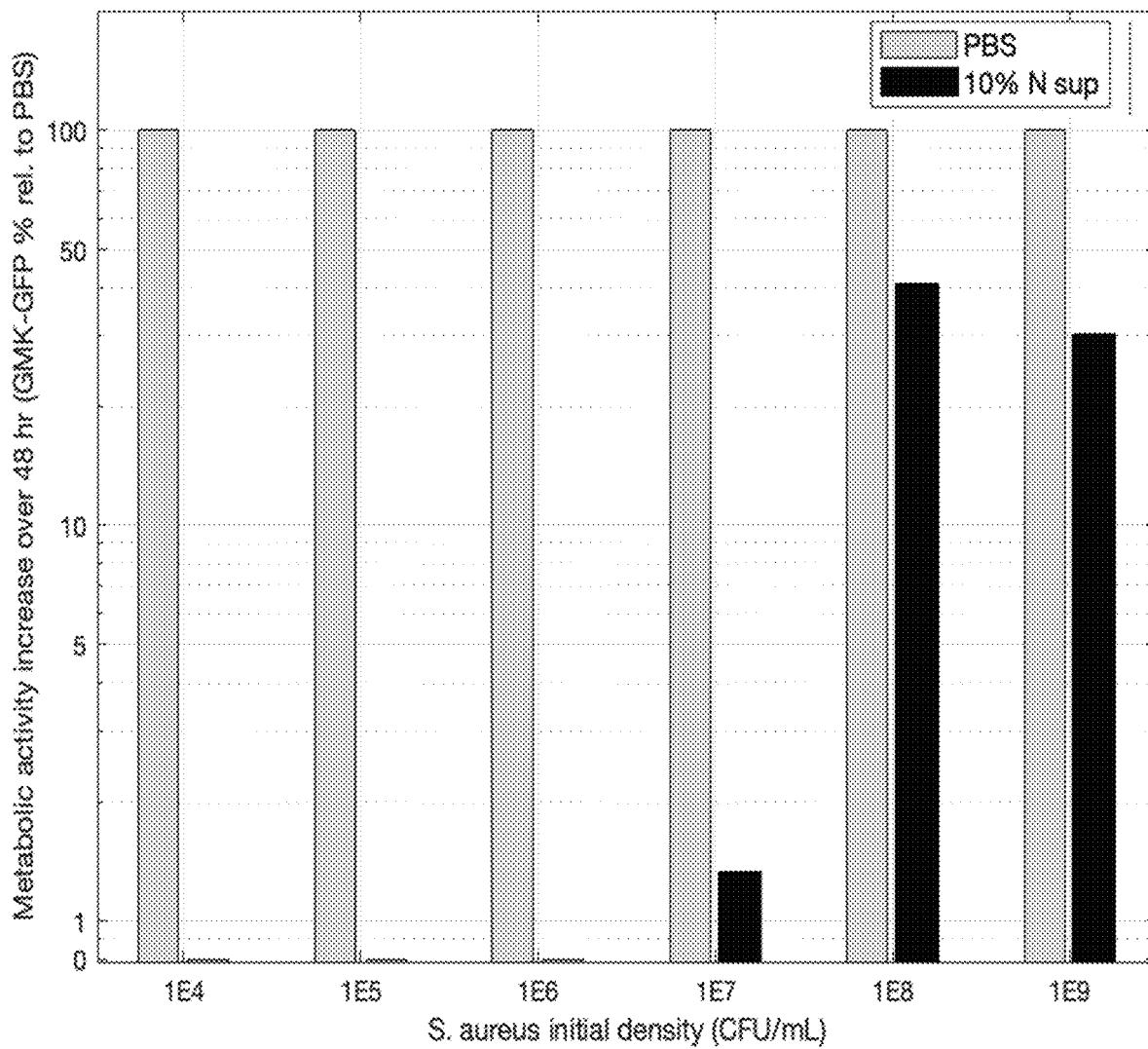
FIGS. 19A-19B, depict bar graphs that show metabolic activity and quorum sensing activity in different densities of *S. aureus* cultures. Supernatant (10%) from Strain jl.68 or PBS (control) was added to the different concentrations of *S. aureus*.
Figure 19B:
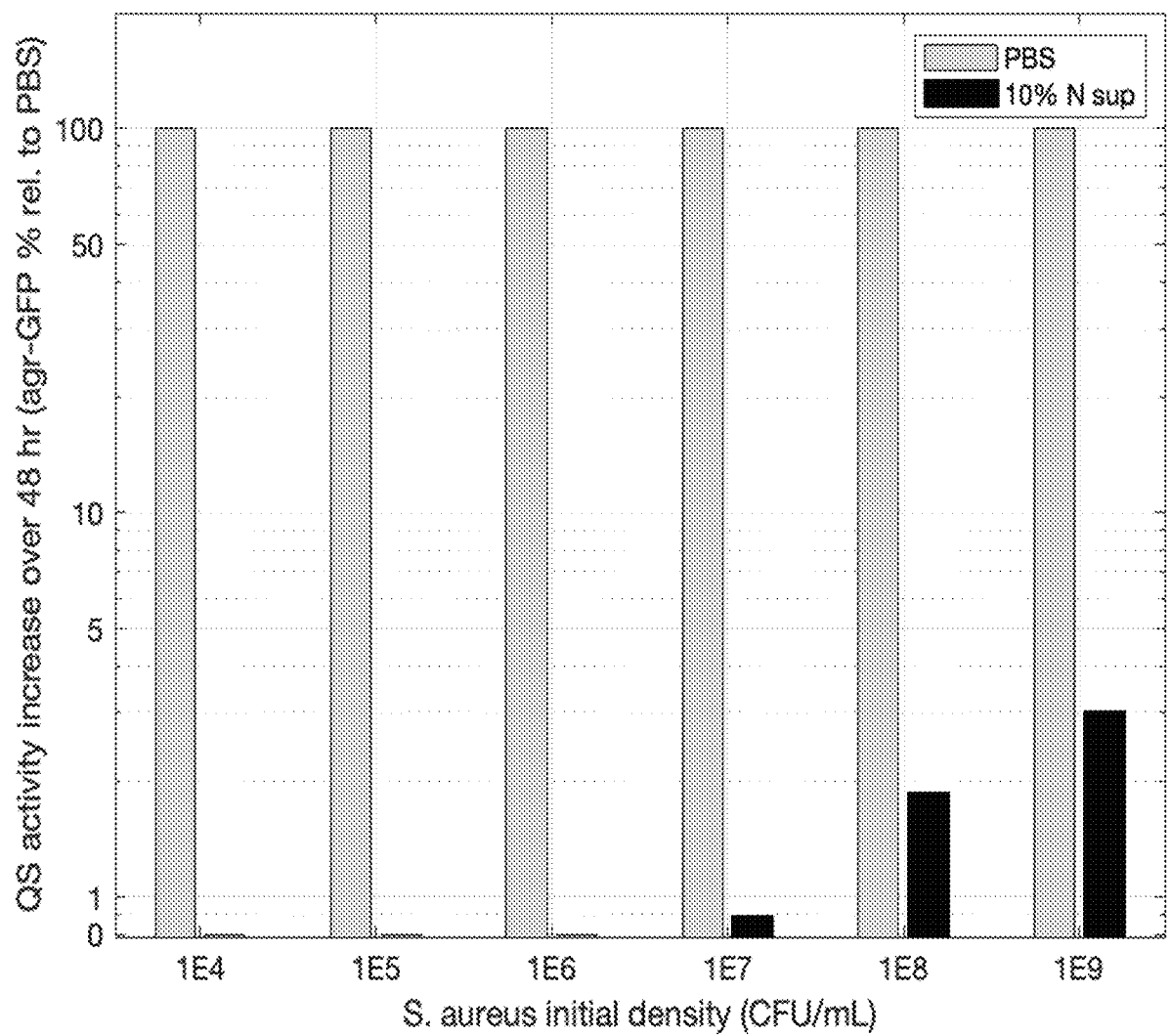

Example 15: Metabolism and Quorum Sensing Expression of S. aureus after Mixture with Supernatant of a Selected Strain S. aureus reporter strains containing a GMK promoter fused GFP reporter or an agr promoter fused GFP reporter were grown in liquid cultures at increasing starting densities of: 1E4, 1E5, 1E6, 1E7, 1E8, or 1E9 CFU/ml. The liquid cultures were mixed with PBS or 10% (v/v) of supernatant from an overnight culture of Strain jl.68. The cultures were grown for 48 hours. The levels of expression were compared to a PBS control and calculated by (time 48–time 0)/(time 48 PBS-time 0 PBS). FIG. 19A shows a graph plotting the expression of GMK, and FIG. 19B shows the expression of agr. The graphs show the GMK or agr activity over 48 hours as compared to a PBS control on the Y-axis. The X-axis shows the different concentrations of S. aureus initial densities. Metabolism (and by extension, quorum sensing) appeared to be arrested for S. aureus low-density cultures (starting at or below 1E6 CFU/mL). While metabolism appeared to be partially restored for medium- and higher-density S. aureus cultures (20-30% relative to no-supernatant), quorum sensing increased only marginally (1-3% relative to no-supernatant). The results from this experiment may indicate supernatant slows metabolism, driving S. aureus into a more slowly growing regime in which it does not quorum sense and/or supernatant acts on quorum sensing, slowing overall metabolic activity.

Figure 20:
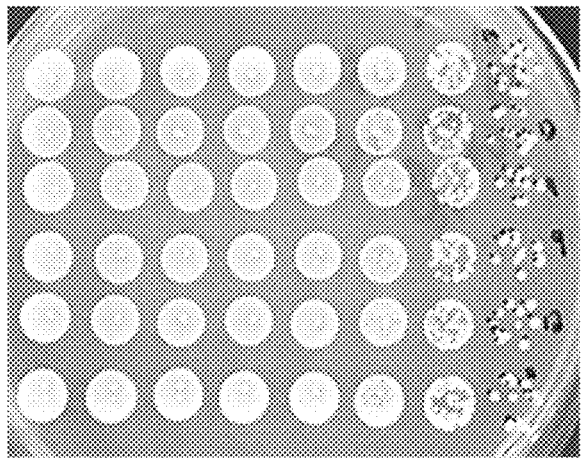
FIG. 20, depict images of agar plates that show different concentrations (0%, 5%, and 10%) of supernatant from Strain jl.68 embedded in TSB agar plates with 10-fold dilutions of *S. aureus* plated on top of the agar. The CFU/ml is the amount of *S. aureus* present on the plates after incubation.
Figure 20:
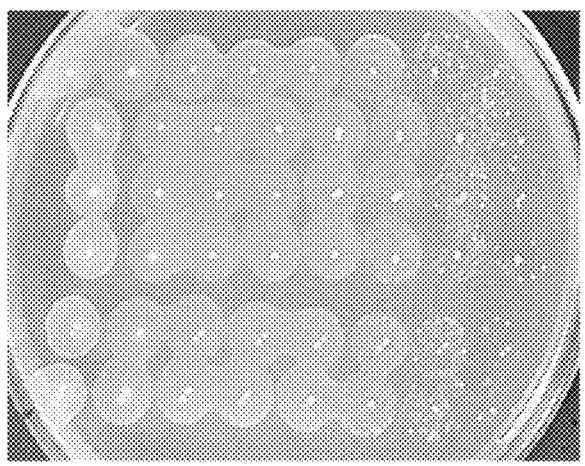
Figure 20:
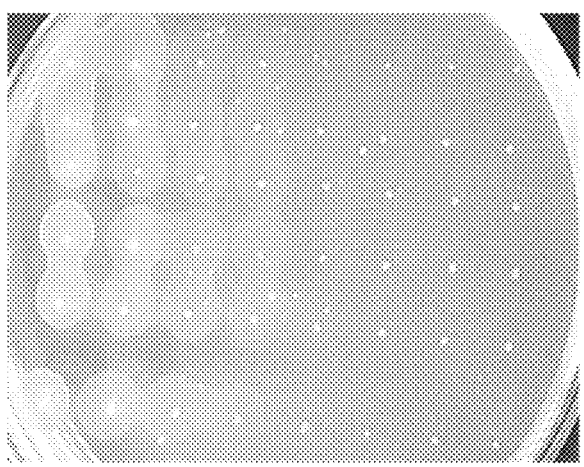

Example 16: Growth Inhibition of S. aureus after Mixture with Supernatant of a Selected Strain S. aureus containing an agr promoter fused GFP reporter was plated in 10-fold dilutions on TSB agar plates containing 0% (PBS control), 5% or 10% (v/v) supernatant from Strain jl.68. The plates were incubated for 18 hours at 37° C. and colonies were counted. FIG. 20 shows images of the plates containing the dilutions of S. aureus on the agar plates comprising the various percentages of supernatant from Strain jl.68. In the presence of unaltered TSB medium, individual colonies were countable around 6-7 10-fold dilutions of a saturated culture. They were bright and fluorescent, indicating quorum sensing was on. In the presence of 5% Strain jl.68 supernatant, colonies were visibly smaller and much less fluorescent, suggesting growth and quorum sensing were affected. Colony count did not change appreciably compared to the TSB-only control. At 18 hours, the colonies were hardly visible. In the presence of 10% Strain jl.68 supernatant, there were no countable colonies. A residue of the plated cultures was present and fluoresce was not detected. Occasionally, colonies emerged within the less-diluted cases that overcome the inhibitory effect of the supernatant. Together the data shows Strain jl.68 supernatant embedded into agar surface substantially eliminated S. aureus colony outgrowth and quorum sensing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition, wherein the composition comprises:
bacterial strains that are purified, lyophilized, and comprise:
   a first bacterial strain, which is a *Lysinibacillus* strain that comprises a 16S rRNA gene sequence with at least 98% sequence identity to SEQ ID NO: 2; and
   a second bacterial strain, which is a *Bacillus* strain that comprises a 16S rRNA gene sequence with at least 99% sequence identity to SEQ ID NO: 4, and
wherein the composition comprises an effective amount of a lyoprotectant.

2. The composition of claim 1, wherein the 16S rRNA gene sequence of the first bacterial strain comprises at least 98% sequence identity over at least 1000 bases to SEQ ID NO: 2.

3. The composition of claim 1, wherein the 16S rRNA gene sequence of the second bacterial strain comprises at least 99% sequence identity over at least 1000 bases to SEQ ID NO: 4.

4. The composition of claim 1, wherein the first bacterial strain further comprises a nucleic acid with a sequence with at least 99% sequence identity to SEQ ID NO: 7.

5. The composition of claim 1, wherein the second bacterial strain further comprises a nucleic acid with a sequence with at least 99% sequence identity to SEQ ID NO: 11.

6. The composition of claim 1, wherein the second bacterial strain further comprises a nucleic acid with a sequence with at least 99% sequence identity to SEQ ID NO: 13.

7. The composition of claim 1, wherein the 16S rRNA gene sequence of the second bacterial strain comprises SEQ ID NO: 4 or SEQ ID NO: 5.

8. The composition of claim 1, wherein the composition further comprises a third bacterial strain, which is a *Bacillus* strain.

9. The composition of claim 8, wherein the 16S rRNA gene sequence of the second bacterial strain comprises SEQ ID NO: 4 and a 16S rRNA gene sequence of the third bacterial strain comprises SEQ ID NO: 5.

10. The composition of claim 9, wherein the 16S rRNA gene sequence of the first bacterial strain comprises SEQ ID NO: 2, the 16S rRNA gene sequence of the second bacterial strain comprises SEQ ID NO: 4 and the 16S rRNA gene sequence of the third bacterial strain comprises SEQ ID NO: 5.

11. The composition of claim 1, wherein the composition comprises at least 10^3 colony forming units (CFU) of bacteria per gram of the composition.

12. The composition of claim 1, wherein the composition comprises 10^3 to 10^12 colony forming units (CFU) of bacteria per gram of the composition.

13. The composition of claim 1, wherein the bacterial strains are present in a ratio of CFU of about 1:1 relative to each other.

14. The composition of claim 1, wherein the bacterial strains are cultured prior to lyophilization in aerobic conditions.

15. The composition of claim 1, wherein the bacterial strains are cultured prior to lyophilization in media without animal products.

16. The composition of claim 1, wherein the bacterial strains are cultured prior to lyophilization in Tryptic Soy Broth (TSB).

17. The composition of claim 1, further comprising an excipient.

18. The composition of claim 17, wherein the excipient comprises growth medium components.

19. The composition of claim 1, further comprising a thiamine or a salt thereof.

20. The composition of claim 1, further comprising a sugar.

21. The composition of claim 1, wherein the composition is located within a container.

22. The composition of claim 21, wherein the container is a solid material.

23. The composition of claim 21, wherein the container is a glass, plastic, or metal.

24. The composition of claim 1, wherein the bacterial strains when present in an effective amount and contacted with *S. aureus* cause a reduction in expression of at least one of the following genes: gmk, agr, psma, saeR, ccpA, and SigB in *S. aureus*, as compared to the expression of the at least one of the following genes: gmk, agr psma, saeR, ccpA, and SigB in *S. aureus* that is not contacted with the bacterial strains in the effective amount wherein the reduction in expression is measured by a fluorescence reporter assay.

25. The composition of claim 1, wherein the bacterial strains when present in an effective amount and contacted with *S. aureus* suppress virulence of *S. aureus* as measured by a reduction in expression of at least one of the following genes: gmk, agr, psma, saeR, ccpA, and SigB in *S. aureus*, as compared to the expression of the at least one of the following genes: gmk, agr, psma, saeR, ccpA, and SigB in *S. aureus* that is not contacted with the bacterial strains in the effective amount wherein the reduction in expression is measured by a fluorescence reporter assay.

26. The composition of claim 1, wherein the composition is located within a vial.

27. The composition of claim 1, wherein the composition comprises the bacterial strains individually in an amount of at least 10^4 to 10^8 colony forming units (CFU) of bacteria per gram of the composition.

* * * * *